US010470694B2

(12) United States Patent
Darty et al.

(10) Patent No.: US 10,470,694 B2
(45) Date of Patent: *Nov. 12, 2019

(54) SYSTEMS AND METHODS FOR MEASURING TISSUE OXYGENATION

(71) Applicant: Hypermed Imaging, Inc., Memphis, TN (US)

(72) Inventors: Mark Anthony Darty, Collierville, TN (US); Dmitry Yudovsky, Los Angeles, CA (US)

(73) Assignee: Hypermed Imaging, Inc., Memphis, TN (US)

( * ) Notice: Subject to any disclaimer, the term of this patent is extended or adjusted under 35 U.S.C. 154(b) by 52 days.

This patent is subject to a terminal disclaimer.

(21) Appl. No.: 15/702,596

(22) Filed: Sep. 12, 2017

(65) Prior Publication Data

US 2018/0103883 A1 Apr. 19, 2018

Related U.S. Application Data

(63) Continuation of application No. 15/267,090, filed on Sep. 15, 2016, now Pat. No. 10,010,278, which is a
(Continued)

(51) Int. Cl.
*A61B 6/00* (2006.01)
*A61B 5/1455* (2006.01)
*A61B 5/00* (2006.01)

(52) U.S. Cl.
CPC .......... *A61B 5/14552* (2013.01); *A61B 5/443* (2013.01); *A61B 5/7203* (2013.01); *A61B 2562/0233* (2013.01); *A61B 2576/00* (2013.01)

(58) Field of Classification Search
CPC . A61B 5/14552; A61B 5/7203; A61B 5/7278; A61B 5/0077; A61B 2562/0233;
(Continued)

(56) References Cited

U.S. PATENT DOCUMENTS 5,784,162 A 7/1998 Cabib et al.
8,644,911 B1 2/2014 Panasyuk et al.
(Continued)

FOREIGN PATENT DOCUMENTS

WO WO 2017/066493 A1 4/2017

OTHER PUBLICATIONS

U.S. Appl. No. 14/664,793, 2015-0265195, U.S. Pat. No. 9,480,424, filed Mar. 20, 2015, Sep. 24, 2015, Nov. 1, 2016.
(Continued)

*Primary Examiner* — Elmer M Chao
(74) *Attorney, Agent, or Firm* — Brett A. Lovejoy; Andrew J. Antczak; Morgan, Lewis & Bockius LLP

(57) ABSTRACT

The disclosure provides methods and systems for determining tissue oxygenation. An electronic device obtains a data set including a plurality of images of a tissue of interest, each resolved at a different spectral band. Spectral analysis is performed, upon image registration, at a plurality of points in a two-dimensional area of the images of the tissue. The spectral analysis including determining approximate values of oxyhemoglobin levels and deoxyhemoglobin levels at each respective point in the plurality of points. The predetermined set of eight to twelve spectral bands includes spectral bands that provide improved methods for measuring tissue oxygenation.

11 Claims, 24 Drawing Sheets
(13 of 24 Drawing Sheet(s) Filed in Color)

Related U.S. Application Data continuation-in-part of application No. 14/664,793, filed on Mar. 20, 2015, now Pat. No. 9,480,424.

(60) Provisional application No. 62/090,324, filed on Dec. 10, 2014, provisional application No. 62/090,302, filed on Dec. 10, 2014, provisional application No. 61/969,039, filed on Mar. 21, 2014.

(58) Field of Classification Search
CPC ............ A61B 2562/04; A61B 2576/00; G06T 7/0012; G06T 2207/10024; G06T 2207/30088

See application file for complete search history.

(56) References Cited

U.S. PATENT DOCUMENTS

| | | | |
|---|---|---|---|
| 8,810,658 | B2 | 8/2014 | Skaff |
| 9,078,619 | B2 | 7/2015 | Panasyuk et al. |
| 9,619,883 | B2 | 4/2017 | Yudovsky |
| 2004/0236229 | A1 | 11/2004 | Freeman et al. |
| 2005/0273011 | A1 | 12/2005 | Hattery |
| 2009/0225277 | A1 | 9/2009 | Gil |
| 2010/0056928 | A1 | 3/2010 | Zuzak et al. |
| 2010/0069758 | A1 | 3/2010 | Barnes et al. |
| 2013/0041267 | A1 | 2/2013 | Ntziachristos et al. |
| 2015/0265150 | A1 | 9/2015 | Darty et al. |
| 2015/0265195 | A1 | 9/2015 | Darty et al. |

OTHER PUBLICATIONS

U.S. Appl. No. 15/267,090, 2017-0224260, U.S. Pat. No. 10,010,278, filed Sep. 15, 2016, Aug. 10, 2017, Jul. 3, 2018.

U.S. Appl. No. 14/372,711, 2015-0051498, U.S. Pat. No. 9,107,624, filed Jul. 16, 2014, Feb. 19, 2015, Aug. 18, 2015.

U.S. Appl. No. 14/333,406, 2015-0308896, U.S. Pat. No. 9,354,115, filed Jul. 16, 2014, Oct. 29, 2015, May 31, 2016.

U.S. Appl. No. 15/143,399, 2016-0345835, filed Apr. 29, 2016, Dec. 1, 2016.

U.S. Appl. No. 13/844,737, 2015-0177429, U.S. Pat. No. 9,766,382, filed Mar. 15, 2013, Jun. 25, 2015, Sep. 19, 2017.

U.S. Appl. No. 14/664,754, 2015-0271380, U.S. Pat. No. 9,648,254, filed Mar. 20, 2015, Sep. 24, 2015, May 9, 2017.

U.S. Appl. No. 15/352,504, 2017-0067781, U.S. Pat. No. 9,746,377, filed Nov. 15, 2016, Mar. 9, 2017, Aug. 29, 2017.

U.S. Appl. No. 14/664,791, 2015-0265150, U.S. Pat. No. 9,655,519, filed Mar. 20, 2015, Sep. 24, 2015, May 23, 2017.

U.S. Appl. No. 15/151,419, 2016-0249810, U.S. Pat. No. 9,526,427, filed May 10, 2016, Sep. 1, 2016, Dec. 27, 2016.

```
┌─────────────────────────────────────────────────────────────────┐
│  Perform spectral analysis at a plurality of points in a two-dimensional area  │──412
│  of the plurality of images of the tissue, the spectral analysis including     │
│  determining approximate values of oxyhemoglobin levels and                    │
│  deoxyhemoglobin levels at each respective point in the plurality of points    │
│                              ⓑ                                                 │
│  ┌───────────────────────────────────────────────────────────┐                 │
│  │  The predetermined set of eight to twelve spectral bands includes │──418    │
│  │  spectral bands having central wavelengths of:                    │         │
│  │  (i) 510±3 nm, 530±3 nm, 540±3 nm, 560±3 nm, 580±3 nm,            │         │
│  │      590±3 nm, 620±3 nm, and 660±3 nm;                            │         │
│  │  (ii) 520±3 nm, 540±3 nm, 560±3 nm, 580±3 nm, 590±3 nm,           │         │
│  │      610±3 nm, 620±3 nm, and 640±3 nm; or                         │         │
│  │  (iii) 500±3 nm, 530±3 nm, 545±3 nm, 570±3 nm, 585±3 nm,          │         │
│  │      600±3 nm, 615±3 nm, and 640±3 nm                             │         │
│  │  ┌─ ─ ─ ─ ─ ─ ─ ─ ─ ─ ─ ─ ─ ─ ─ ─ ─ ─ ─ ─ ─ ─ ─ ─ ─ ─ ─ ─ ┐      │         │
│  │  │ The predetermined set of eight to twelve spectral bands consists │──420 │
│  │  │ of eight spectral bands having central wavelengths of:            │      │
│  │  │ (i) 510 nm, 530 nm, 540 nm, 560 nm, 580 nm, 590 nm,               │      │
│  │  │     620 nm, and 660 nm;                                           │      │
│  │  │ (ii) 520 nm, 540 nm, 560 nm, 580 nm, 590 nm, 610 nm,              │      │
│  │  │     620 nm, and 640 nm; or                                        │      │
│  │  │ (iii) 500 nm, 530 nm, 545 nm, 570 nm, 585 nm, 600 nm,             │      │
│  │  │     615 nm, and 640 nm                                            │      │
│  │  └─ ─ ─ ─ ─ ─ ─ ─ ─ ─ ─ ─ ─ ─ ─ ─ ─ ─ ─ ─ ─ ─ ─ ─ ─ ─ ─ ─ ┘      │         │
│  └───────────────────────────────────────────────────────────┘                 │
│  ┌───────────────────────────────────────────────────────────┐                 │
│  │  Each respective spectral band in the eight to twelve spectral bands │──422 │
│  │  has a full width at half maximum of less than 15 nm                 │      │
│  │  ┌─ ─ ─ ─ ─ ─ ─ ─ ─ ─ ─ ─ ─ ─ ─ ─ ─ ─ ─ ─ ─ ─ ─ ─ ─ ─ ┐           │──424  │
│  │  │ Each respective spectral band in the eight to twelve spectral │           │
│  │  │ bands has a full width at half maximum of less than 5 nm      │           │
│  │  └─ ─ ─ ─ ─ ─ ─ ─ ─ ─ ─ ─ ─ ─ ─ ─ ─ ─ ─ ─ ─ ─ ─ ─ ─ ─ ┘           │       │
│  └───────────────────────────────────────────────────────────┘                 │
└─────────────────────────────────────────────────────────────────┘
```

Figure 4C

| 33 | 62 | 94 | 105 | 109 | 111 | 111 | 98 | 74 |
|----|----|----|-----|-----|-----|-----|----|----|
| 38 | 67 | 89 | 97  | 104 | 105 | 112 | 101| 73 |
| 45 | 61 | 79 | 79  | 89  | 93  | 101 | 98 | 72 |
| 49 | 56 | 73 | 69  | 76  | 85  | 97  | 97 | 73 |
| 48 | 54 | 67 | 62  | 69  | 81  | 96  | 95 | 77 |
| 47 | 61 | 64 | 57  | 58  | 78  | 90  | 95 | 80 |
| 52 | 70 | 61 | 56  | 64  | 79  | 92  | 95 | 83 |
| 59 | 70 | 68 | 66  | 68  | 86  | 95  | 98 | 85 |
| 69 | 84 | 80 | 77  | 87  | 97  | 105 | 110| 97 |

Figure 9

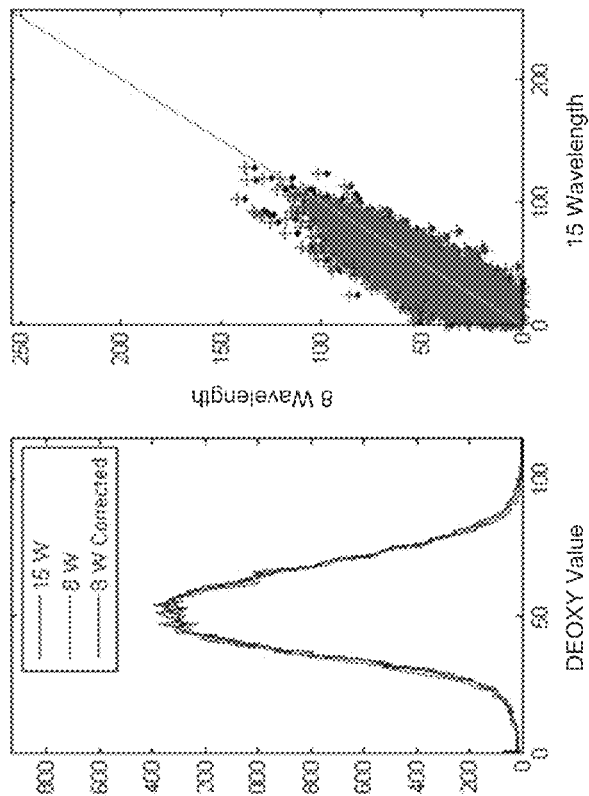
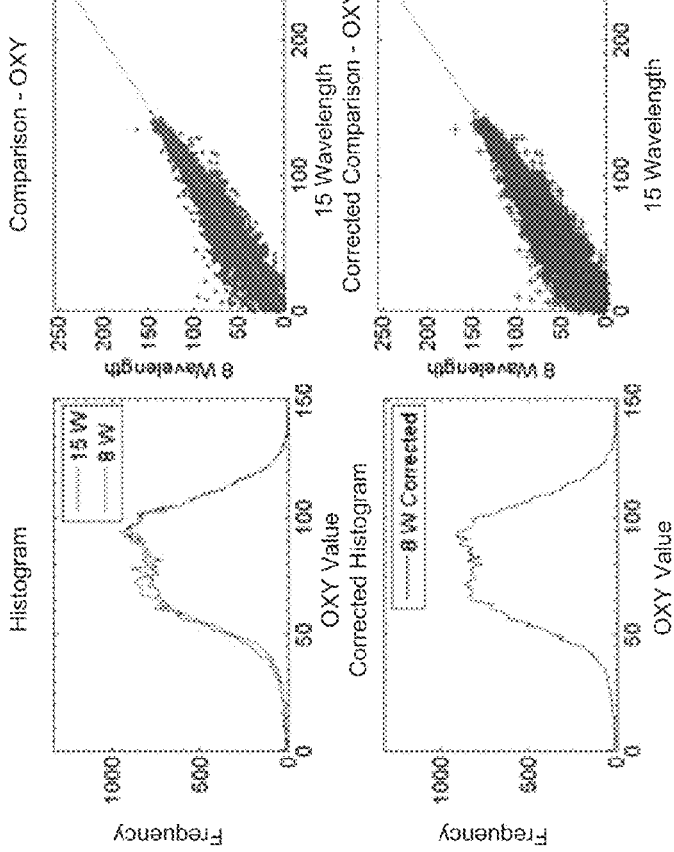
Figure 12A  Figure 12B  Figure 12C  Figure 12D

OXY – All Wavelengths

| 33 | 62 | 94 | 105 | 109 | 111 | 111 | 98 | 74 |
|---|---|---|---|---|---|---|---|---|
| 38 | 67 | 89 | 97 | 104 | 105 | 112 | 101 | 73 |
| 45 | 61 | 79 | 79 | 89 | 93 | 101 | 98 | 72 |
| 49 | 56 | 73 | 69 | 76 | 85 | 97 | 97 | 73 |
| 48 | 54 | 67 | 62 | 69 | 81 | 96 | 95 | 77 |
| 47 | 61 | 64 | 57 | 58 | 78 | 90 | 95 | 80 |
| 52 | 70 | 61 | 56 | 64 | 79 | 92 | 95 | 83 |
| 59 | 70 | 68 | 66 | 68 | 86 | 95 | 98 | 85 |
| 69 | 84 | 80 | 77 | 67 | 97 | 105 | 110 | 97 |

Figure 13A

OXY – Corrected Error

| 11 | 6 | 2 | 1 | 0 | 0 | -1 | 0 | -2 |
|---|---|---|---|---|---|---|---|---|
| 8 | 4 | 2 | 0 | 0 | -1 | -1 | -1 | -3 |
| 1 | 3 | 0 | 0 | 0 | -1 | -1 | -1 | -3 |
| 3 | 2 | 0 | 1 | 0 | -1 | -1 | -1 | -2 |
| 7 | 2 | 1 | 2 | 0 | -1 | -1 | 0 | -1 |
| 6 | 1 | 2 | 2 | 3 | 0 | -1 | 0 | -2 |
| 4 | 1 | 1 | 1 | 1 | 0 | -1 | -1 | -2 |
| 6 | 1 | 0 | 1 | 0 | 0 | -1 | -1 | -1 |
| 5 | -2 | -1 | 0 | -1 | -1 | -2 | -1 | -1 |

Figure 13B

DEOXY – All Wavelengths

| 37 | 44 | 56 | 68 | 68 | 74 | 75 | 69 | 61 |
|---|---|---|---|---|---|---|---|---|
| 27 | 46 | 55 | 59 | 65 | 69 | 71 | 69 | 64 |
| 27 | 43 | 49 | 50 | 57 | 60 | 62 | 67 | 63 |
| 29 | 37 | 42 | 41 | 49 | 58 | 60 | 66 | 63 |
| 28 | 36 | 40 | 36 | 40 | 54 | 61 | 67 | 64 |
| 33 | 38 | 38 | 37 | 44 | 51 | 57 | 63 | 59 |
| 41 | 47 | 37 | 35 | 41 | 48 | 53 | 58 | 54 |
| 44 | 46 | 38 | 40 | 43 | 48 | 52 | 55 | 56 |
| 51 | 47 | 44 | 42 | 44 | 53 | 55 | 55 | 54 |

Figure 13C

DEOXY – Corrected Error

| 7 | 1 | -2 | -2 | -2 | 0 | 0 | -1 | -5 |
|---|---|---|---|---|---|---|---|---|
| -1 | 0 | -2 | -1 | 0 | 0 | 0 | -1 | -3 |
| 1 | 0 | -2 | -2 | -1 | -1 | -1 | -1 | -3 |
| 2 | 0 | -1 | -1 | -1 | -1 | -1 | -1 | -3 |
| 6 | 0 | -2 | -2 | -2 | 0 | -1 | -1 | -3 |
| 3 | 0 | -2 | 3 | 0 | -1 | -1 | -2 | -2 |
| 5 | 0 | -2 | -2 | -1 | 0 | -1 | -1 | -2 |
| 2 | 0 | -2 | -1 | 0 | 0 | 0 | -1 | -1 |
| 0 | 0 | -1 | -2 | -1 | 0 | 0 | 0 | -1 |

Figure 13D

SYSTEMS AND METHODS FOR MEASURING TISSUE OXYGENATION

CROSS REFERENCE TO RELATED APPLICATIONS

This application is a continuation of U.S. patent application Ser. No. 15/267,090, filed Sep. 15, 2016 which is a continuation-in-part of U.S. patent application Ser. No. 14/664,793, filed Mar. 20, 2015, and issued as U.S. Pat. No. 9,480,424, which claims priority to U.S. Provisional Patent Application No. 61/969,039, filed Mar. 21, 2014, U.S. Provisional Patent Application No. 62/090,302, filed Dec. 10, 2014, and U.S. Provisional Patent Application No. 62/090,324, filed Dec. 10, 2014, the disclosures of which are hereby incorporated by reference herein in their entireties for all purposes.

TECHNICAL FIELD

The present disclosure generally relates to spectroscopy, such as hyperspectral or multi-spectral imaging, and in particular, to systems, methods and devices for performing hyperspectral imaging of chromophore systems.

BACKGROUND

Hyperspectral (also known as "multispectral") spectroscopy is an imaging technique that integrates multiple images of an object resolved at different spectral bands (e.g., ranges of wavelengths) into a single data structure, referred to as a three-dimensional hyperspectral data cube. Hyperspectral spectroscopy is often used to identify an individual component of a complex composition through the recognition of corresponding spectral signatures of the individual components in a particular hyperspectral data cube.

Hyperspectral spectroscopy has been used in a variety of applications, ranging from geological and agricultural surveying to military surveillance and industrial evaluation. Hyperspectral spectroscopy has also been used in medical applications to facilitate complex diagnosis and predict treatment outcomes. For example, medical hyperspectral imaging has been used to accurately predict viability and survival of tissue deprived of adequate perfusion, and to differentiate diseased (e.g. tumor) and ischemic tissue from normal tissue.

Despite the great potential clinical value of hyperspectral imaging, however, several drawbacks have limited the use of hyperspectral imaging in the clinic setting. In particular, current medical hyperspectral instruments are costly because of the complex optics and computational requirements currently used to resolve images at a plurality of spectral bands to generate a suitable hyperspectral data cube. Hyperspectral imaging instruments can also suffer from poor temporal and spatial resolution, as well as low optical throughput, due to the complex optics and taxing computational requirements needed for assembling, processing, and analyzing data into a hyperspectral data cube suitable for medical use. Moreover, because hyperspectral imaging is time consuming and requires complex optical equipment, it is more expensive than the conventional methods.

SUMMARY

Various implementations of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various implementations are used to enable improved ulcer formation detection.

In one implementation, the disclosure provides methods, devices, and nontransitory computer-readable storage medium for determining tissue oxygenation according to a method. The method includes obtaining a data set comprising a plurality of images of a tissue of interest. Each respective image in the plurality of images is resolved at a different spectral band, in a predetermined set of eight to twelve spectral bands. Further, each respective image in the plurality of images comprises an array of pixel values. In the method, the plurality of images are registered, using the processor, on a pixel-by-pixel basis, to form a plurality of registered images of the tissue. This plurality of images is referred to as a composite image or a hypercube. In the method, spectral analysis is performed at a plurality of points in a two-dimensional area of the plurality of registered images of the tissue. In some instances, the term "point" and "pixel" is synonymous. However, in other instances, each "point" is a predetermined number of pixels in the two-dimensional area of the plurality of registered images of the tissue. For instance, in some embodiments, there is a one-to-many relationship between points and pixels, where, for example, (e.g., each point represents two pixels, each point represent three pixels, and so forth). In the method, the spectral analysis includes determining approximate values of oxyhemoglobin levels and deoxyhemoglobin levels at each respective point in the plurality of points.

In some embodiments, the predetermined set of eight to ten spectral bands includes all the spectral bands in the set of {510±3 nm, 530±3 nm, 540±3 nm, 560±3 nm, 580±3 nm, 590±3 nm, 620±3 nm, and 660±3 nm}, where each respective spectral band in the eight to ten spectral bands has a full width at half maximum of less than 15 nm, less than 10 nm, or 5 nm or less.

In some embodiments, the predetermined set of eight to ten spectral bands includes spectral bands in the set of {520±3 nm, 540±3 nm, 560±3 nm, 580±3 nm, 590±3 nm, 610±3 nm, 620±3 nm, and 640±3 nm}, where each respective spectral band in the eight to ten spectral bands has a full width at half maximum of less than 15 nm, less than 10 nm, or 5 nm or less.

In some embodiments, the predetermined set of eight to ten spectral bands includes spectral bands in the set of {500±3 nm, 530±3 nm, 545±3 nm, 570±3 nm, 585±3 nm, 600±3 nm, 615±3 nm, and 640±3 nm}, where each respective spectral band in the eight to ten spectral bands has a full width at half maximum of less than 15 nm, less than 10 nm, or 5 nm or less.

In some embodiments, the predetermined set of eight to ten spectral bands includes spectral bands in the set of {520±3 nm, 540±3 nm, 560±3 nm, 580±3 nm, 590±3 nm, 610±3 nm, 620±3 nm, and 660±3 nm}, where the spectral bands having central wavelengths of 520±3 nm, 540±3 nm, 560±3 nm, 580±3 nm, 590±3 nm, 610±3 nm, and 620±3 nm have a full width at half maximum of less than 15 nm, less than 10 nm, or less than 5 nm or less, and the spectral band having the central wavelength of 660±3 nm has a full width at half maximum of less than 20 nm, less than 15 nm, or less than 10 nm or less.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the present disclosure can be understood in greater detail, a more particular description may be had by reference to the features of various implementations, some of which are illustrated in the appended drawings. The appended drawings, however, merely illustrate the more pertinent features of the present disclosure and are therefore not to be considered limiting, for the description may admit to other effective features and arrangements.

FIGS. 4A, 4B and 4C are flow-diagrams illustrating a method of measuring tissue oxygenation according to some implementations.

FIG. 9 illustrates an example of the output from averaging OXY values over the square segmentation of an OXY map, generated according to some implementations.

FIG. 11C—DEOXY) and those generated using only the eight wavelengths of exemplary subset 5778 (FIG. 11B—OXY; FIG. 11D—DEOXY), according to some implementations. The OXY and DEOXY maps generated using only eight wavelengths were corrected using linear correction factors for subset number 2. FIG. 11E shows a native image of the tissue.

FIGS. 12A, 12B, 12C, and 12D illustrate statistics generated from the three OXY and DEOXY maps generated using all fifteen wavelengths or only the eight wavelengths of exemplary subset 5778, from the first hyperspectral data set, according to some implementations. FIGS. 12A and 12C illustrate histograms showing the pixel value distribution of the OXY and DEOXY maps, respectively. FIGS. 12B and 12D illustrate scatter plots of the uncorrected and corrected pixel values determined using eight wavelengths plotted against pixel values determined using all fifteen wavelengths.

FIGS. 13A, 13B, 13C, and 13D illustrate qualitative analysis of the OXY and DEOXY maps generated from the first data set, using fifteen and eight wavelengths, according to some implementations. FIGS. 13A and 13C illustrate mean pixel values for approximately 40-pixel squares overlaid on the OXY and DEOXY maps generated using all fifteen wavelengths, respectively. The cross indicates the bottom right of each square. FIGS. 13B and 13D illustrate the difference between the averaged values in the maps generated using fifteen wavelengths and the corrected maps generated using the eight wavelengths of exemplary subset 5778, overlaid on OXY and DEOXY maps generated using the corrected eight wavelengths, respectively.

FIG. 14C—DEOXY) and those generated using only the eight wavelengths of exemplary subset 5778 (FIG. 14B—OXY; FIG. 14D—DEOXY), according to some implementations. The OXY and DEOXY maps generated using only eight wavelengths were corrected using the linear correction factors for subset number 2. FIG. 14E shows a native image of the tissue.

FIGS. 15A and 15C illustrate histograms showing the pixel value distribution of the OXY and DEOXY maps, respectively. FIGS. 15B and 15D illustrate scatter plots of the uncorrected and corrected pixel values determined using eight wavelengths plotted against pixel values determined using all fifteen wavelengths.

FIGS. 16A and 16C illustrate mean pixel values for approximately 40-pixel squares overlaid on the OXY and DEOXY maps generated using all fifteen wavelengths, respectively. The cross indicates the bottom right of each square. FIGS. 16B and 16D illustrate the difference between the averaged values in the maps generated using fifteen wavelengths and the corrected maps generated using the eight wavelengths of exemplary subset 5778, overlaid on OXY and DEOXY maps generated using the corrected eight wavelengths, respectively.

FIG. 17C—DEOXY) and those generated using only the eight wavelengths of exemplary subset 5778 (FIG. 17B—OXY; FIG. 17D—DEOXY), according to some implementations. The OXY and DEOXY maps generated using only eight wavelengths were corrected using the linear correction factors for subset number 2. FIG. 17E shows a native image of the tissue.

FIGS. 18A and 18C illustrate histograms showing the pixel value distribution of the OXY and DEOXY maps, respectively. FIGS. 18B and 18D illustrate scatter plots of the uncorrected and corrected pixel values determined using eight wavelengths plotted against pixel values determined using all fifteen wavelengths.

FIGS. 19A and 19C illustrate mean pixel values for approximately 40-pixel squares overlaid on the OXY and DEOXY maps generated using all fifteen wavelengths, respectively. The cross indicates the bottom right of each square. FIGS. 19B and 19D illustrate the difference between the averaged values in the maps generated using fifteen wavelengths and the corrected maps generated using the eight wavelengths of exemplary subset 5778, overlaid on OXY and DEOXY maps generated using the corrected eight wavelengths, respectively.

FIG. 21A illustrates a scatter plot of OXY and DEOXY values determined for healing and non-healing ulcers. The cloud of green points represent individual instances of the Monte Carlo analysis. FIG. 21B illustrates the sensitivity, specificity, and positive predictive values determined for the simulation.

DETAILED DESCRIPTION

Numerous details are described herein in order to provide a thorough understanding of the example implementations illustrated in the accompanying drawings. However, the invention may be practiced without many of the specific details. And, well-known methods, components, and circuits have not been described in exhaustive detail so as not to unnecessarily obscure more pertinent aspects of the implementations described herein.

Figure 1A:
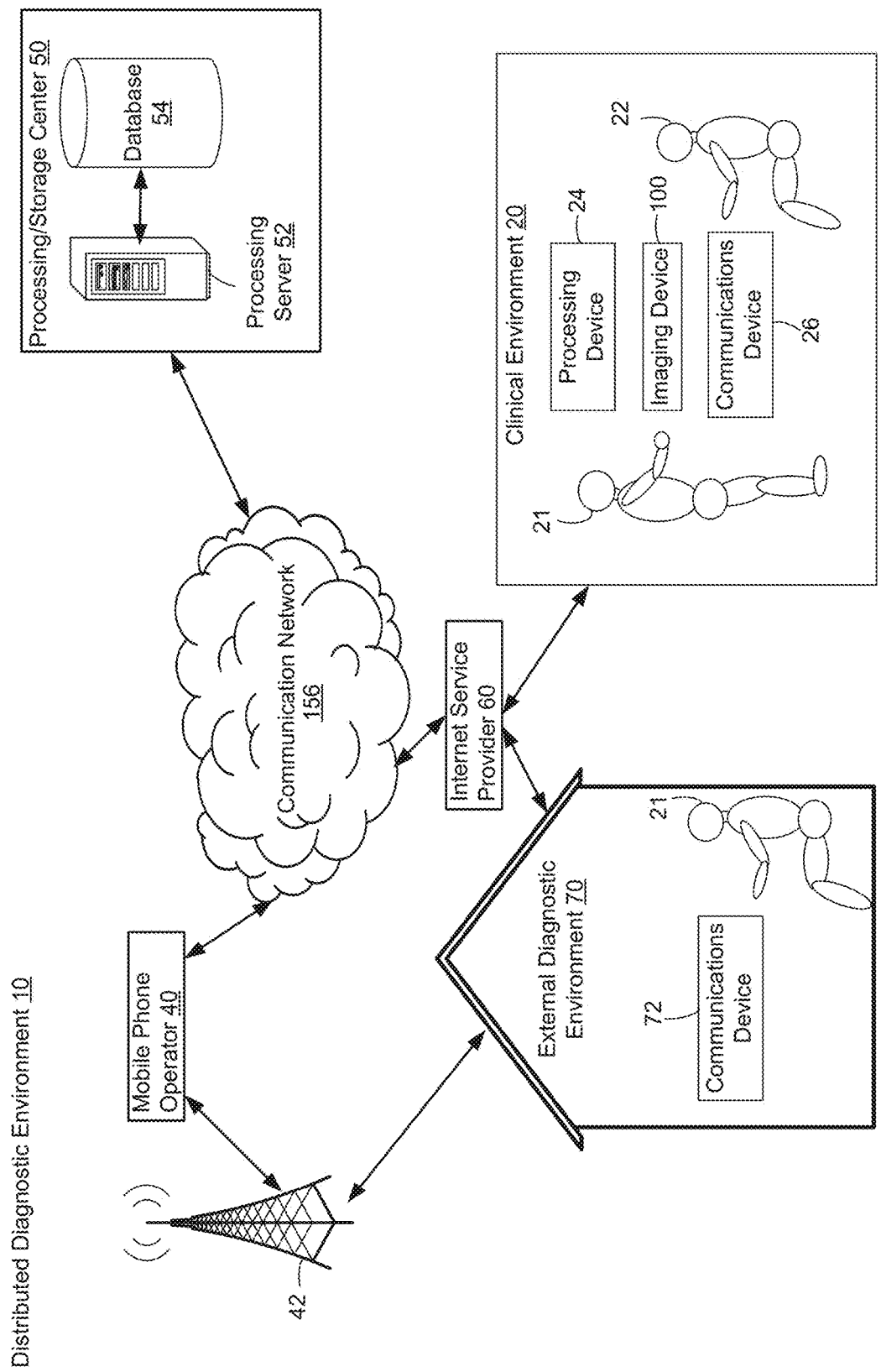
FIG. 1A is a schematic example of a distributed diagnostic environment including a hyperspectral imaging device according to some implementations.
Figure 1B:
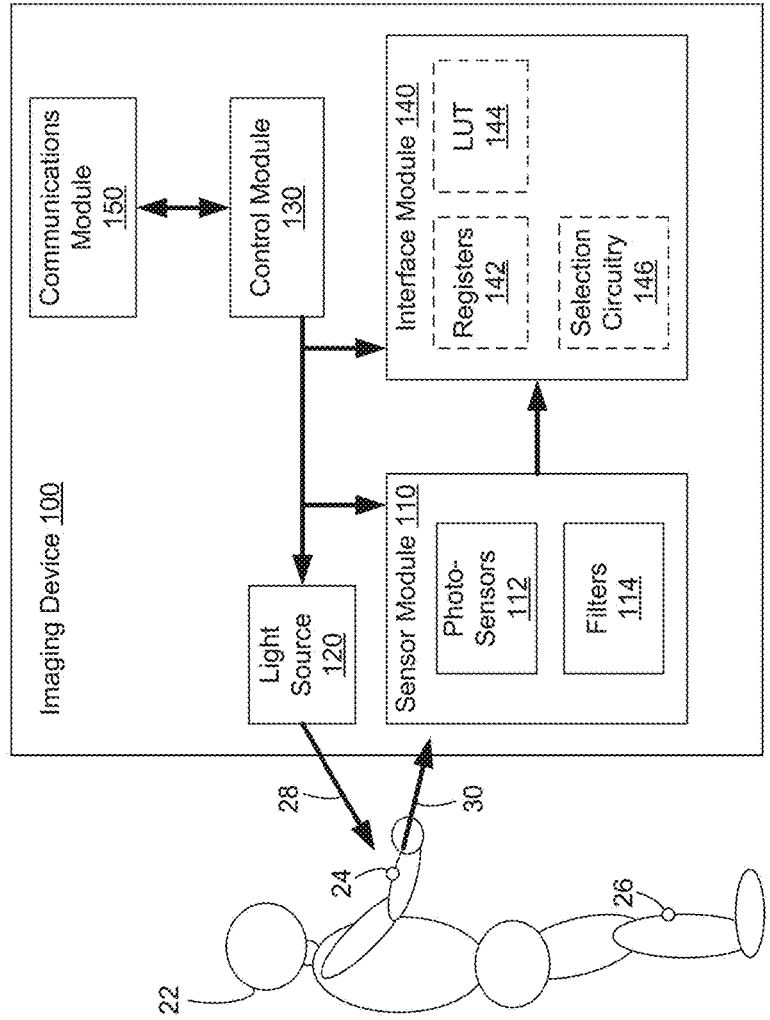
FIG. 1B is a schematic diagram of a local diagnostic environment according to some implementations.
Figure 2:
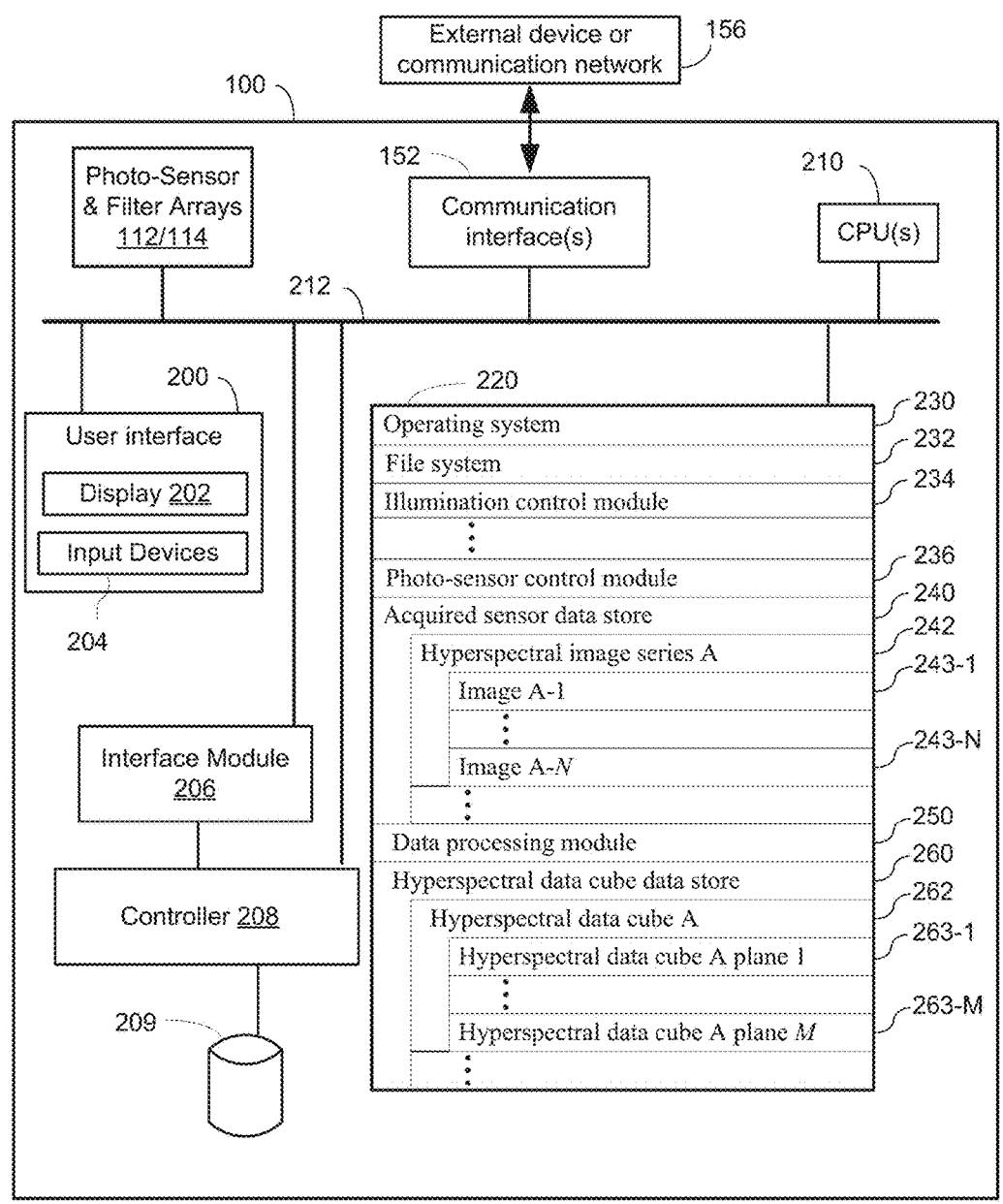
FIG. 2 is a block diagram of an implementation of a hyperspectral imaging device used in accordance with some embodiments of the present disclosure.
Figure 3:
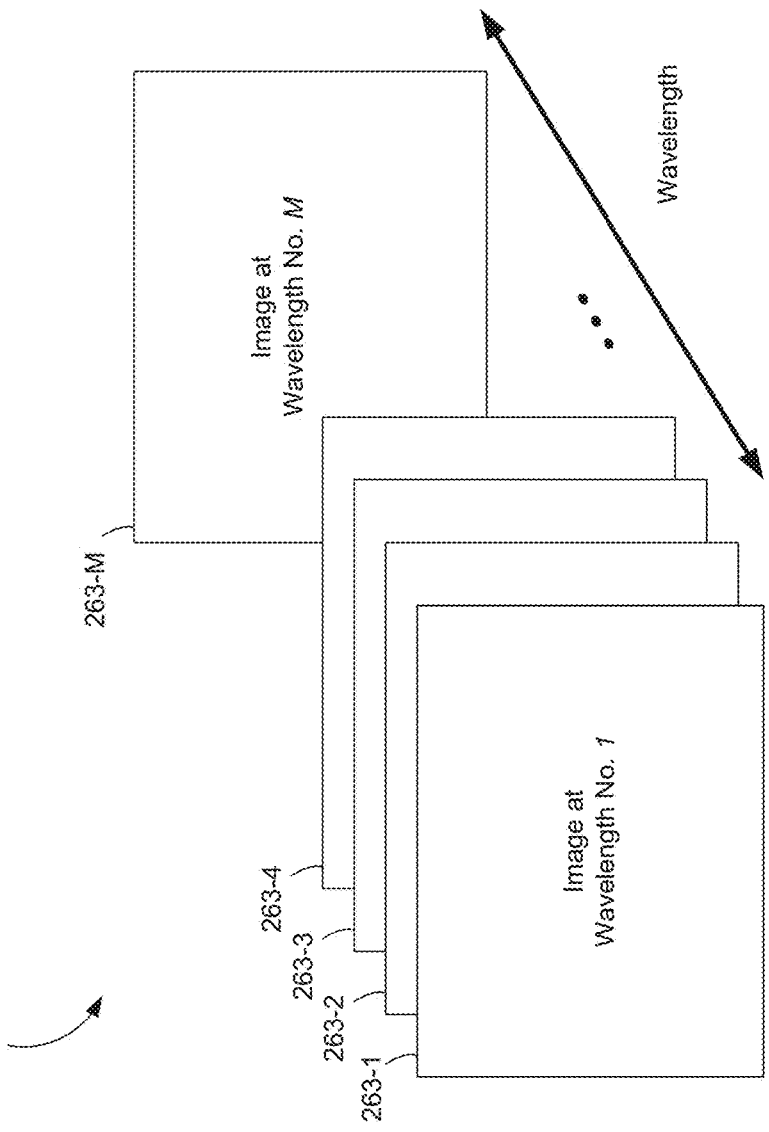
FIG. 3 is a schematic illustration of a hyperspectral data cube.
Figure 4A:
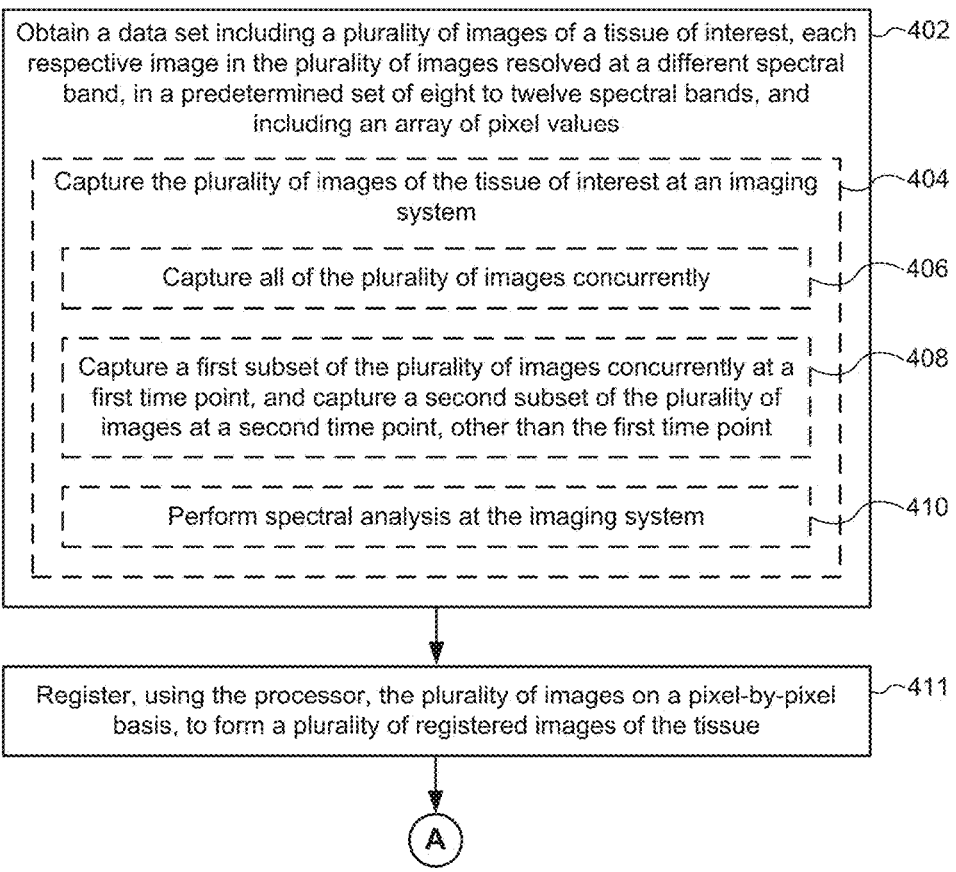
Figure 4B:
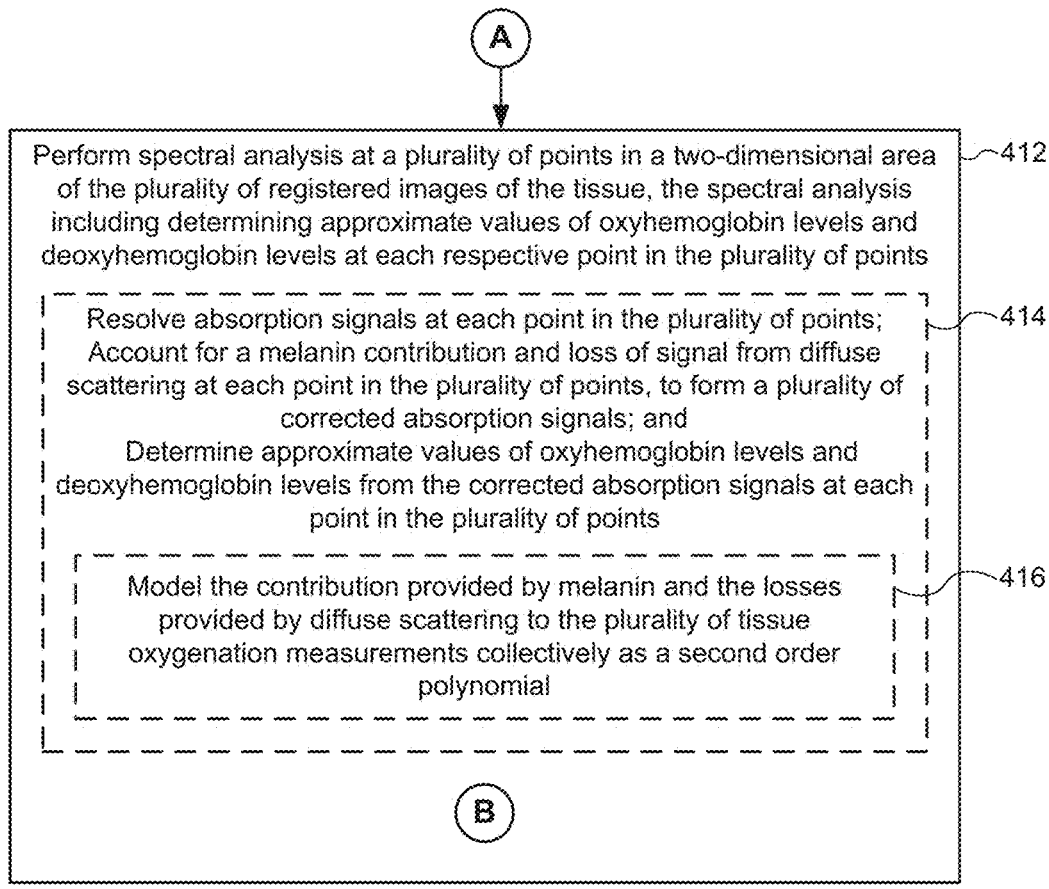

FIGS. 1-3, described below, provide descriptions of exemplary imaging systems and hyperspectral data cubes for use with the embodiment described herein. FIGS. 4A-4C are flow diagrams illustrating a method of measuring tissue oxygenation.

FIG. 1A is an example of a distributed diagnostic environment 10 including an imaging device 100 according to some implementations. In some implementations, the distributed diagnostic environment 10 includes one or more clinical environments 20, one or more processing and/or storage centers 50, and a communication network 156 that, together with one or more Internet Service Providers 60 and/or Mobile phone operators 40, with concomitant cell towers 42, allow communication between the one or more clinical environments 20 and the one or more processing and/or storage centers 50.

The clinical environment 20 depicted in FIG. 1 is designed to accommodate the demand of many subjects 22, by taking advantage of improved hyperspectral imaging techniques described herein. In some implementations, the clinical environment 20 includes a medical professional 21 operating an imaging device 100 to collect a series of images of a subject's 22 tissue. In some embodiments, the clinical environment also includes a communication device 26 that communicates with processing and/or storage center 50 via communications network 156. In some embodiments, the clinical environment 20 includes a processing device 24 for processing hyperspectral images without reliance on processing and/or storage center 50. In some embodiments, the clinical environment includes both a communication device 26 and a processing device 24.

In some implementations, the imaging device 100 illuminates an object (e.g., an area of the body of a subject 22) and generates imaging data of the object. In some implementations, the imaging device 100 illuminates an object using one or more light sources 120. In some implementations, after illuminating the object, or concurrently thereto, the imaging device 100 generates and transmits imaging data (e.g., the hyperspectral image data set) corresponding to the object to processing and/or storage center 50 for forming a processed hyperspectral image. In other implementations, the imaging device 100 and/or processing device 24 form the processed hyperspectral image using the image data set, and transmits the processed hyperspectral image to the processing and/or storage center 50.

In some implementations, spectral analysis of the imaging data is performed at the processing and/or storage center 50, e.g., using processing server 52. In some implementations, a record of the spectral analysis is created in a database 54 at the processing and/or storage center 50. In some implementations, a record of the spectral analysis and/or an indication of a physiologic condition based on the spectral analysis is sent from the processing and/or storage center 50 back to the clinical environment 20.

In some implementations, image capture and processing includes the imaging device 100 collecting a plurality of images of a region of interest of a subject (e.g., a first image captured at a first spectral bandwidth and a second image captured at a second spectral bandwidth). The imaging device 100 stores each respective image at a respective memory location (e.g., the first image is stored at a first location in memory 220 and the second image is stored at a second location in memory 220). The imaging device 100 compares, on a pixel-by-pixel basis (e.g., with processor 210), each pixel of the respective images to produce a composite (e.g., hyperspectral, multi-spectral) image of the region of interest of the subject. In some implementations, individual pixel values are binned, averaged, or otherwise arithmetically manipulated prior to pixel-by-pixel analysis, e.g., pixel-by-pixel comparison includes comparison of binned, averaged, or otherwise arithmetically manipulated pixel values.

In other implementations, spectral analysis is performed at the clinical environment 20, e.g., using the imaging device 100 and/or processing device 24. In some implementations, a record of the spectral analysis and/or an indication of a physiologic condition based on the spectral analysis is then sent from the clinical environment 20 to the processing and/or storage center 50, where a record is created in database 54. In some implementations, a record of the spectral analysis and/or an indication of a physiologic condition is created at a local database in the clinical environment 20. In some implementations, the local database is in the imaging device 100, allowing for optional transfer later to a different local or external database. In other embodiments, the local database is connected wired or wirelessly to the imaging device 100 or processing device 24.

In some implementations, a record of the spectral analysis and/or an indication of a physiologic condition is outputted at the clinical environment for examination by a medical professional 21, which may be the same or different medical professional who operated the imaging device. In some implementations, a record of the spectral analysis and/or an indication of a physiologic condition is outputted at an external diagnostics environment 70 including a communications device 72 in communication with the clinical environment 20 and/or processing and/or storage center 50 via the communication network 156.

In some implementations, the medical professional 21, after examining the outputted spectral analysis or indication of a physiological condition, assigns a course of treatment for the subject 22. In some implementations, the treatment may be administered by the same medical professional 21 who operated the imaging device 100, by the medical professional 21 who reviewed the indication of the physiological parameter, by another medical professional 21, or by the subject 22 themselves.

FIG. 1B is a schematic diagram of a clinical diagnostic environment 20 according to some implementations. The clinical diagnostic environment 20 includes an imaging device 100 and a communications module 150. The communications module 150 is used, for example, to optionally communicate imaging data to a remote location, to communicate a record of the imaging analysis and/or an indication of a physiologic condition, and/or to receive software updates or diagnostic information.

In some implementations, the imaging device 100 illuminates an area of the body of a subject 22 (e.g., a location on an upper extremity 24 or location on a lower extremity 26 of the subject 22) and generates imaging data of the area. In some implementations, the imaging device 100 illuminates the area of the body of the subject using one or more light sources (120). Such light sources emit light 28 that is reflected by area 24 to form reflected light 30 that is received by sensor module 110. Sensor module 100 includes photo-sensors 112 and filters 114.

In some embodiments, for example, where the imaging device 100 employs a photo-sensor array coupled to a filter array, the output from the photo-sensors 112 is sent to registers 142 of an interface module 140 and processed by one or more register look-up tables 144 and selection circuitry 146. For instance, in some embodiments, look-up table 144 is used in the following manner. In such embodiments, for purposes of illustration, registers 142 is a plurality of registers. The imaging device 100 uses the registers 142 to receive the output of the photo-sensors 112 and the control module 130 identifies which registers 142 in the plurality of registers correspond to filter elements of a particular filter-type in a plurality of filter-types using the look-up table. The control module 130 selects one or more subsets of photo-sensor outputs from the plurality of registers based on the identification of the registers that correspond to filter elements of the particular filter-type. The independent subsets of photo-sensors are then used to form independent images, each image corresponding to a filter-type. To this end, in some implementations there is selection control circuitry 146 to select data using column select and row select circuitry. This data is stored and processed in registers 142.

Operation of the light source 120, sensor module 110 and interface module 140 is under the control of control module 130. In some embodiments, as illustrated in FIG. 1B, control module 130, in turn, interacts with a communications module 150 in order to facilitate the acquisition of imaging data from a subject 22.

FIG. 2 is a block diagram of an implementation of an imaging device, such as imaging device 100. In particular, FIG. 2 is not limited to any particular configuration of image acquisition modalities, such as the beam-steering embodiments described with respect to FIGS. 5 and 6, the single sensor embodiments described with respect to FIG. 7, and the concurrent capture on multiple photo-sensors embodiments described with respect to FIG. 8. In fact, FIG. 2 encompasses any form of imaging device provided that enables collection of a spectral image in accordance with the methods described in more detail below, e.g., in accordance with the methods described in FIGS. 4A-4C.

The methods described herein can be employed with any known hyperspectral/multispectral imaging system or other form of imaging system. For example, in one embodiment, the methods described herein are employed in conjunction with a spatial scanning HSI system. Spatial scanning HSI systems include point scanning and line-scanning imaging systems in which a complete spectrum is concurrently acquired at a single pixel or line of pixels. The instrument then scans through a region of interest collecting complete spectrums at each point (e.g., pixel) or line (e.g., line of pixels) sequentially. In another embodiment, the methods described herein are employed in conjunction with a spectral scanning HSI system. Spectral scanning HSI systems acquire an image of the entire region of interest at a single wavelength with a two-dimensional detector. The instrument collects a series of images of the entire region of interest as each wavelength in a predetermined set of wavelengths.

As such, FIG. 2 encompasses a broad range of imaging devices, provided they are capable of collecting a hyper-spectral image series in the manner disclosed herein. As such, FIG. 2 represents, by way of example and upon adaption to perform the methods disclosed herein, any of the imaging devices of FIGS. 5 through 8 described below, and/or any of the imaging devices disclosed in International Patent Publication Nos. WO 2014/007869, WO 2013/184226, WO 2014/063117, and WO 2014/146053, each of which is hereby incorporated by reference herein in its entirety.

While some example features are illustrated in FIG. 2, those skilled in the art will appreciate from the present disclosure that various other features have not been illustrated for the sake of brevity and so as not to obscure more pertinent aspects of the example implementations disclosed herein. To that end, the imaging device 100 includes one or more central processing units (CPU) 210, an optional main non-volatile storage unit 209, an optional controller 208, a system memory 220 for storing system control programs, data, and application programs, including programs and data optionally loaded from the non-volatile storage unit 209. In some implementations the non-volatile storage unit 209 includes a memory card or other form of nontransitory media, for storing software and data. The storage unit 209 is optionally controlled by the controller 208.

In some implementations, the imaging device 100 optionally includes a user interface 200 including one or more input devices 204 (e.g., a touch screen, buttons, or switches) and/or an optional display 202. Additionally and/or alternatively, in some implementations, the imaging device 100 may be controlled by an external device such as a handheld device, a smartphone (or the like), a tablet computer, a laptop computer, a desktop computer, and/or a server system. To that end, the imaging device 100 includes one or more communication interfaces 152 for connecting to any wired or wireless external device or communication network (e.g. a wide area network such as the Internet) 156. In some embodiments, imaging device 100 is very compact and docks directly onto or with a handheld device, a smartphone (or the like), a tablet computer, and/or a laptop computer by an electronic interface. In some implementations, imaging device 100 docks to a desktop computer (e.g., via a docking station or USB connection. The imaging device 100 includes an internal bus 212 for interconnecting the aforementioned elements. The communication bus 212 may include circuitry (sometimes called a chipset) that interconnects and controls communications between the aforementioned components.

In some implementations, the imaging device 100 communicates with a communication network 156, thereby enabling the imaging device 100 to transmit and/or receive data between mobile communication devices over the communication network, particularly one involving a wireless link, such as cellular, WiFi, ZigBee, BlueTooth, IEEE 802.11b, 802.11a, 802.11g, or 802.11n, etc. The communication network can be any suitable communication network configured to support data transmissions. Suitable communication networks include, but are not limited to, cellular networks, wide area networks (WANs), local area networks (LANs), the Internet, IEEE 802.11b, 802.11a, 802.11g, or 802.11n wireless networks, landline, cable line, fiber-optic line, USB, etc. The imaging system, depending on an embodiment or desired functionality, can work completely offline by virtue of its own computing power, on a network by sending raw or partially processed data, or both concurrently.

The system memory 220 includes high-speed random access memory, such as DRAM, SRAM, DDR RAM, or other random access solid state memory devices; and typically includes non-volatile memory flash memory devices, or other non-transitory solid state storage devices. The system memory 220 optionally includes one or more storage devices remotely located from the CPU(s) 508. The system memory 220, or alternately the non-transitory memory device(s) within system memory 220, comprises a non-transitory computer readable storage medium.

In some implementations, operation of the imaging device 100 is controlled primarily by an operating system 530, which is executed by the CPU 210. The operating system 230 can be stored in the system memory 220 and/or storage unit 209. In some embodiments, the image device 100 is not controlled by an operating system, but rather by some other suitable combination of hardware, firmware and software.

In some implementations, the system memory 220 includes one or more of a file system 232 for controlling access to the various files and data structures described herein, an illumination software control module 234 for controlling a light source associated and/or integrated with the imaging device 100, a photo-sensor control module 236, a sensor data store 240 for storing hyperspectral image series A 242, including images 243-1 to 243-N, acquired by photo-sensors (e.g. the photo-sensors 112), a data processing software module 250 for manipulating the acquired sensor data, a hyperspectral data cube data store 260 for storing hyperspectral data cube A data 262, including data planes 263-1 to 263-M, assembled from the acquired hyperspectral image series, and a communication interface software control module 154 for controlling the communication interface 152 that connects to an external device (e.g., a handheld device, laptop computer, or desktop computer) and/or communication network (e.g. a wide area network such as the Internet).

The acquired sensor data 242 and hyperspectral data cube data 262 can be stored in a storage module in the system memory 220, and do not need to be concurrently present, depending on which stages of the analysis the imaging device 100 has performed at a given time. In some implementations, prior to imaging a subject and after communicating the acquired sensor data or processed data files thereof, the imaging device 100 contains neither acquired sensor data 242 nor the hyperspectral data cube data 262. In some implementations, after imaging a subject and after communicating the acquired sensor data or processed data files thereof, the imaging device 100 retains the acquired sensor data 242 and/or hyperspectral data cube data 262 for a period of time (e.g., until storage space is needed, for a predetermined amount of time, etc.).

In some implementations, the programs or software modules identified above correspond to sets of instructions for performing a function described above. The sets of instructions can be executed by one or more processors, e.g., a CPU(s) 210. The above identified software modules or programs (e.g., sets of instructions) need not be implemented as separate software programs, procedures, or modules, and thus various subsets of these programs or modules may be combined or otherwise re-arranged in various embodiments. In some embodiments, the system memory 220 stores a subset of the modules and data structures identified above. Furthermore, the system memory 220 may store additional modules and data structures not described above.

The system memory 220 optionally also includes one or more of the following software modules, which are not illustrated in FIG. 2: a spectral library which includes profiles for a plurality of medical conditions, a spectral analyzer software module to compare measured spectral data to a spectral library, control modules for additional sensors, information acquired by one or more additional sensors (such as a remote temperature measuring device), an image constructor software module for generating a spectral image, a spectral image assembled based on a hyperspectral data cube and optionally fused with information acquired by an additional sensor, a fusion software control module for integrating data acquired by an additional sensor into a hyperspectral data cube, and a display software control module for controlling a built-in display.

While examining a subject and/or viewing spectral images of the subject, a physician can optionally provide input to the image device 100 that modifies one or more parameters upon which a spectral image and/or diagnostic output is based. In some implementations, this input is provided using input device 204. Among other things, the image device can be controlled to modify the spectral portion selected by a spectral analyzer (e.g., to modify a threshold of analytical sensitivity) or to modify the appearance of the image generated by an image assembler (e.g., to switch from an intensity map to a topological rendering).

In some implementations, the imaging device 100 can be instructed to communicate instructions to an imaging subsystem to modify the sensing properties of the photo-sensors 112 (e.g., an exposure setting, a frame rate, an integration rate, or a wavelength to be detected). Other parameters can also be modified. For example, the imaging device 100 can be instructed to obtain a wide-view image of the subject for screening purposes, or to obtain a close-in image of a particular region of interest.

In some implementations, the imaging device 100 does not include a controller 208 or storage unit 209. In some such implementations, the memory 220 and CPU 210 are one or more application-specific integrated circuit chips (ASICs) and/or programmable logic devices (e.g. an FGPA—Field Programmable Gate Array). For example, in some implementations, an ASIC and/or programmed FPGA includes the instructions of the illumination control module 234, photo-sensor control module 236, and/or the data processing module 250. In some implementations, the ASIC and/or FPGA further includes storage space for the acquired sensor data store 240 and the sensor data 242 stored therein and/or the hyperspectral data cube data store 260 and the hyperspectral/multispectral data cubes 262 stored therein.

In some implementations, the system memory 220 includes a spectral library and a spectral analyzer for comparing hyperspectral data generated by the image device 100 to known spectral patterns associated with various physiologic parameters and/or medical conditions. In some implementations, analysis of the acquired hyperspectral data is performed on an external device such as a handheld device, tablet computer, laptop computer, desktop computer, an external server, for example in a cloud computing environment or processing and/or storage center 50.

In some implementations, a spectral library includes profiles for a plurality of physiologic arterial parameters and/or medical conditions, each of which contains a set of spectral characteristics unique to the medical condition. A spectral analyzer uses the spectral characteristics to determine the probability that a region of the subject corresponding to a measured hyperspectral data cube is afflicted with a physiologic parameter and/or medical condition. In some implementations, each profile includes additional information about the physiological parameter and/or condition, e.g., information about whether the condition is malignant or benign, options for treatment, etc. In some implementations, each profile includes biological information, e.g., information that is used to modify the detection conditions for subjects of different skin types. In some implementations, the spectral library is stored in a single database. In other implementations, such data is instead stored in a plurality of databases that may or may not all be hosted by the same computer, e.g., on two or more computers addressable by wide area network. In some implementations, the spectral library is electronically stored in the storage unit 220 and recalled using the controller 208 when needed during analysis of hyperspectral data cube data.

In some implementations, the spectral analyzer analyzes a particular spectra derived from hyperspectral data cube data, the spectra having pre-defined spectral ranges (e.g., spectral ranges specific for a particular physiologic arterial parameter and/or medical condition), by comparing the spectral characteristics of a pre-determined physiologic arterial parameter and/or medical condition to the subject's spectra within the defined spectral ranges. In some implementations, the pre-defined spectral ranges correspond to values of one or more of deoxyhemoglobin levels, oxyhemoglobin levels, total hemoglobin levels, oxygen saturation, oxygen perfusion, hydration levels, total hematocrit levels, melanin levels, and collagen levels of a tissue on a patient (e.g., an area 24 or 26 of the body of a subject 22). Performing such a comparison only within defined spectral ranges can both improve the accuracy of the characterization and reduce the computational power needed to perform such a characterization.

In some implementations, the physiologic parameter is an arterial parameter selected from the group consisting of blood flow (e.g., blood ingress and/or egress), oxygen delivery, oxygen utilization, oxygen saturation, deoxyhemoglobin levels, oxyhemoglobin levels, total hemoglobin levels, oxygen perfusion, hydration levels, and total hematocrit levels.

In some implementations, the medical condition is selected from the group consisting of peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, detection of advanced glycemic end products (AGEs), exposure to a chemical or biological agent, and an inflammatory response.

In some implementations, the spectral analyzer identifies a spectral signature within the hyperspectral data cube that corresponds with a physiologic parameter and/or medical condition of the patient. In certain implementations, this is accomplished by identifying a pattern of oxidation or hydration in a tissue associated with a tissue of the patient. In some implementations, the analysis of the hyperspectral data cube includes performing at least one of adjusting the brightness of at least one of the respective digital images in the hyperspectral data cube (e.g., data cube plane 362-M at wavelength range No. M), adjusting the contrast of at least one of the respective digital images in the hyperspectral data cube, removing an artifact from at least one of the respective digital images in the hyperspectral data cube, processing one or more sub-pixels of at least one of the respective digital images in the hyperspectral data cube, and transforming a spectral hypercube assembled from a plurality of digital images.

In some implementations, the display 202 receives an indication of a physiologic parameter and/or medical condition (e.g., from an output module), and displays the indication of the physiologic parameter and/or medical condition. In some embodiments, an output module is a general display control module. In some implementations, the display 202 receives an image (e.g., a color image, mono-wavelength image, or hyperspectral/multispectral image) from a display control module, and displays the image. Optionally, the display subsystem also displays a legend that contains additional information. For example, the legend can display information indicating the probability that a region has a particular medical condition, a category of the condition, a probable age of the condition, the boundary of the condition, information about treatment of the condition, information indicating possible new areas of interest for examination, and/or information indicating possible new information that could be useful to obtain a diagnosis, e.g., another test or another spectral area that could be analyzed.

In some implementations, a housing display is built into the housing of the imaging device 100. In an example of such an implementation, a video display in electronic communication with the processor 210 is included. In some implementations, the housing display is a touch screen display that is used to manipulate the displayed image and/or control the image device 100.

In some implementations, the communication interface 152 comprises a docking station for a mobile device having a mobile device display. A mobile device, such as a smart phone, a personal digital assistant (PDA), an enterprise digital assistant, a tablet computer, an IPOD, a digital camera, a portable music player, or a wearable technology device can be connected to the docking station, effectively mounting the mobile device display onto the imaging device 100. Optionally, the mobile device is used to manipulate the displayed image and/or control the image device 100.

In some implementations, the imaging device 100 is configured to be in wired or wireless communication with an external display, for example, on a handheld device, tablet computer, laptop computer, desktop computer, television, IPOD, projector unit, or wearable technology device, on which the image is displayed. Optionally, a user interface on the external device is used to manipulate the displayed image and/or control the imaging device 100.

In some implementations, an image can be displayed in real time on the display. The real-time image can be used, for example, to focus an image of the subject, to select an appropriate region of interest, and to zoom the image of the subject in or out. In one embodiment, the real-time image of the subject is a color image captured by an optical detector that is not covered by a detector filter. In some implementations, the imager subsystem comprises an optical detector dedicated to capturing true color images of a subject. In some implementations, the real-time image of the subject is a mono-wavelength, or narrow-band (e.g., 10-50 nm), image captured by an optical detector covered by a detector filter. In these embodiments, any optical detector covered by a detector filter in the imager subsystem may be used for: (i) resolving digital images of the subject for integration into a hyperspectral data cube, and (ii) resolving narrow-band images for focusing, or otherwise manipulating the optical properties of the imaging device 100.

In some implementations, an indication of a physiologic parameter, medical condition, and/or hyperspectral image constructed from data captured by the photo-sensors 112 is displayed on an internal housing display, mounted housing display, or external display. Assembled hyperspectral data (e.g., present in a hyperspectral/multispectral data cube) is used to create a two-dimensional representation of the imaged object or subject, based on one or more parameters (e.g., a physiologic arterial parameter). An image constructor module, stored in the imaging system memory or in an external device, constructs an image based on, for example, one or more analyzed spectra. Specifically, the image constructor creates a representation of information within the one or more spectra. In one example, the image constructor constructs a two-dimensional intensity map in which the spatially-varying intensity of one or more particular wavelengths (or wavelength ranges) within the one or more spectra is represented by a corresponding spatially varying intensity of a visible marker.

In some implementations, the image constructor fuses a hyperspectral image with information obtained from one or more additional sensors. Non-limiting examples of suitable image fusion methods include: band overlay, high-pass filtering method, intensity hue-saturation, principle component analysis, and discrete wavelet transform.

FIG. 3 is a schematic illustration of a hyperspectral data cube 262. Hyperspectral sensors collect information as a set of images, which are referred to herein as hyperspectral data cube planes 263. Each image 263 represents a range of the electromagnetic spectrum and is also known as a spectral band. These images 263 are then combined and form a three-dimensional hyperspectral data cube 262 for processing and analysis.

FIGS. 4A-4B are flow diagrams illustrating a method 400 of measuring tissue oxygenation. The method 400 is performed at an electronic device having one or more processors and memory. In some implementations one or more steps of the method are performed at an imaging system (e.g., imaging system 100, FIG. 1; coaxial imaging system 500 employing a beam steering element, FIG. 5; single-sensor imaging system 700 employing photo-sensor and filter arrays, FIG. 7; or concurrent capture imaging system 800, FIG. 8).

The electronic device (e.g., a computer or imaging system) obtains (402) a data set (e.g., hyperspectral image series 242 or hyperspectral data cube 262) including a plurality of images (e.g., images 231) of a tissue of interest.

Each respective image in the plurality of images is resolved at a different spectral band, in a predetermined set of eight to twelve spectral bands, and includes an array of pixel values. For in instance, in some embodiments, each respective image comprises 500,000 or more pixel values, 1,000,000 or more pixel values, 1,100,000 or more pixel values, 1,200,000 or more pixel values, or 1,300,000 or more measured pixel values. In some implementations, the hyperspectral data set also includes data from images resolved at spectral bands other than those of the predetermined set of eight to ten spectral bands (e.g., data that will not be included in the processing steps described herein).

Figure 5:
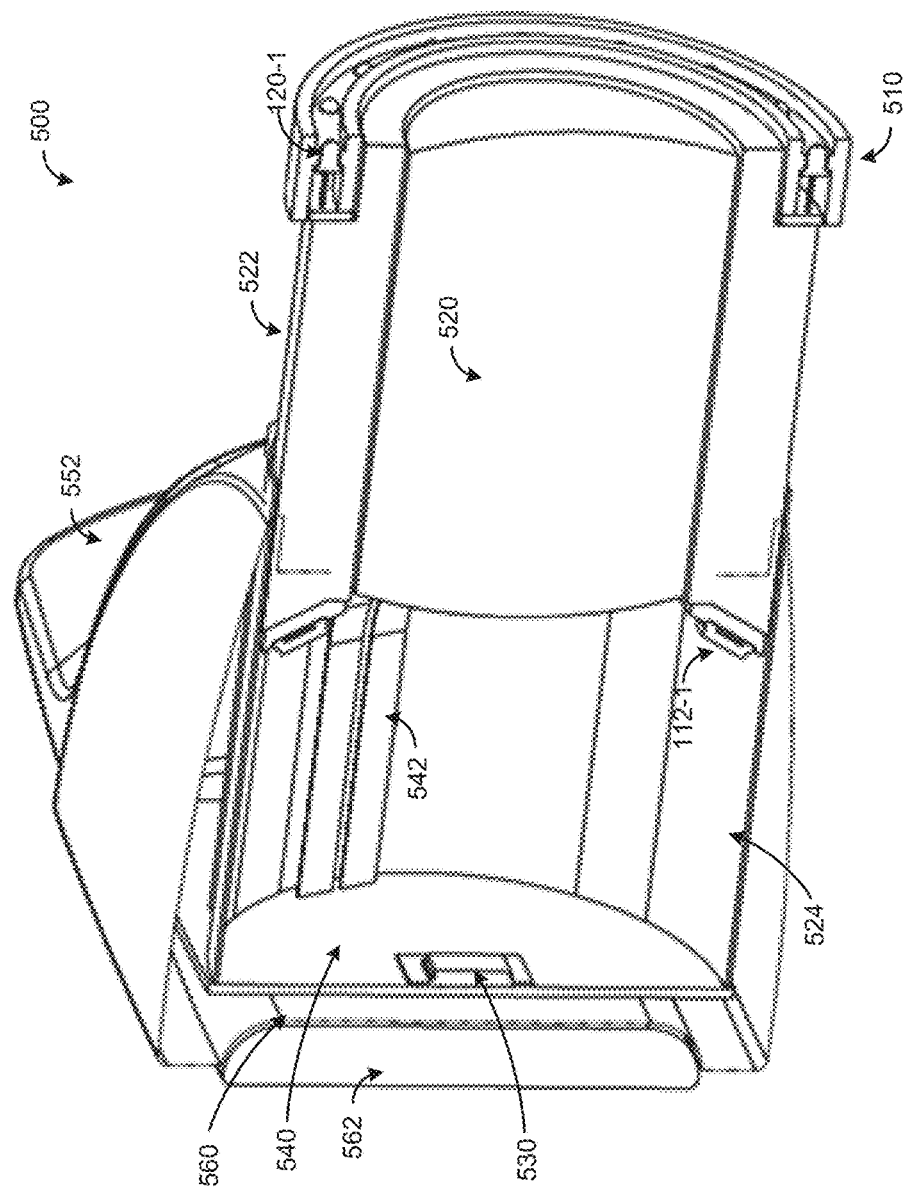
FIG. 5 is a schematic illustration of the internal hardware of a co-axial hyperspectral/multispectral camera mounted in a housing, according to some implementations. The illustration shows a cross-section down the barrel of the camera with a perspective view of the beam steering element 204.
Figure 7:
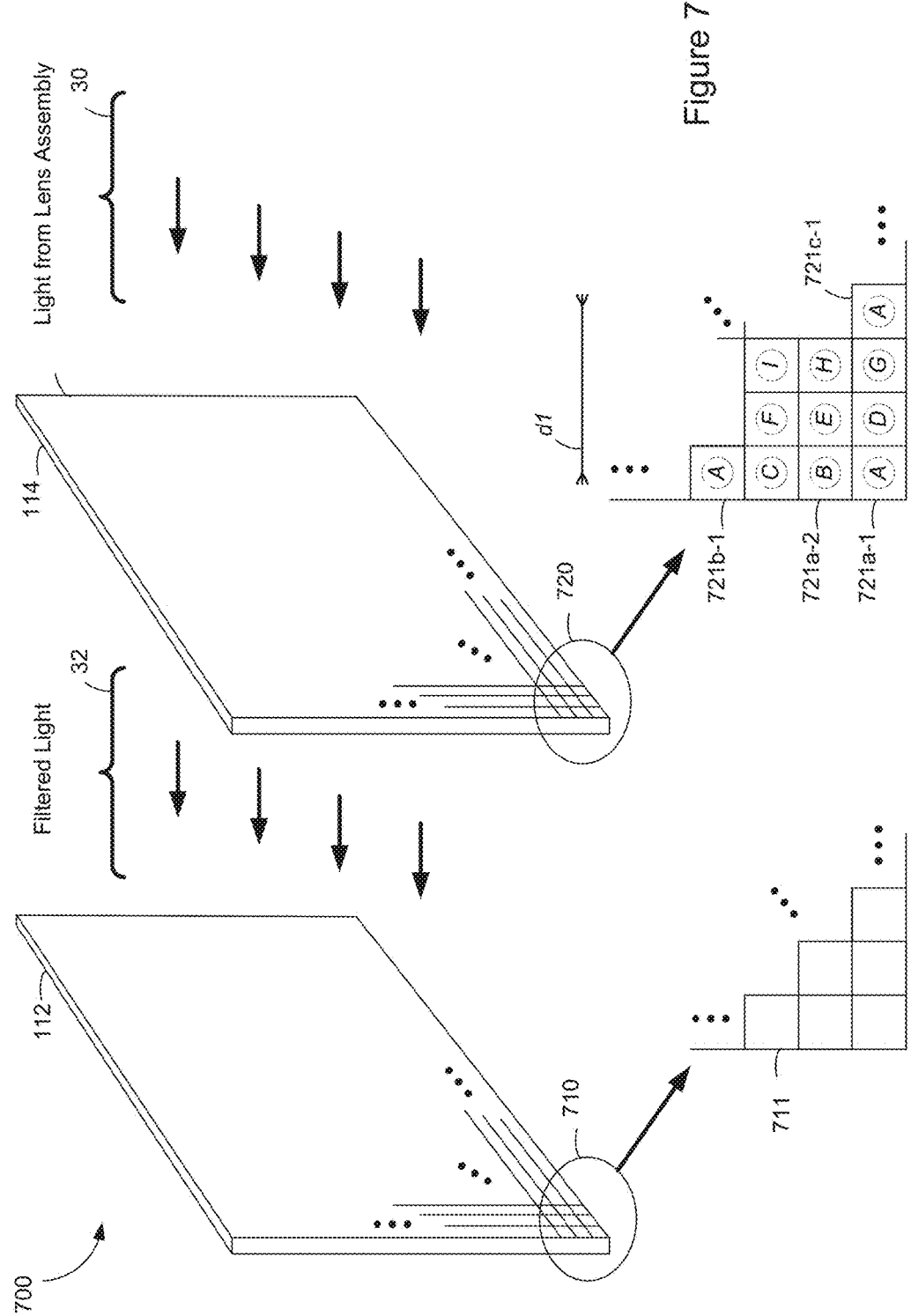
FIG. 7 is an exploded schematic view of an implementation of an image sensor assembly, according to some implementations employing a single-sensor hyperspectral imager.
Figure 8:
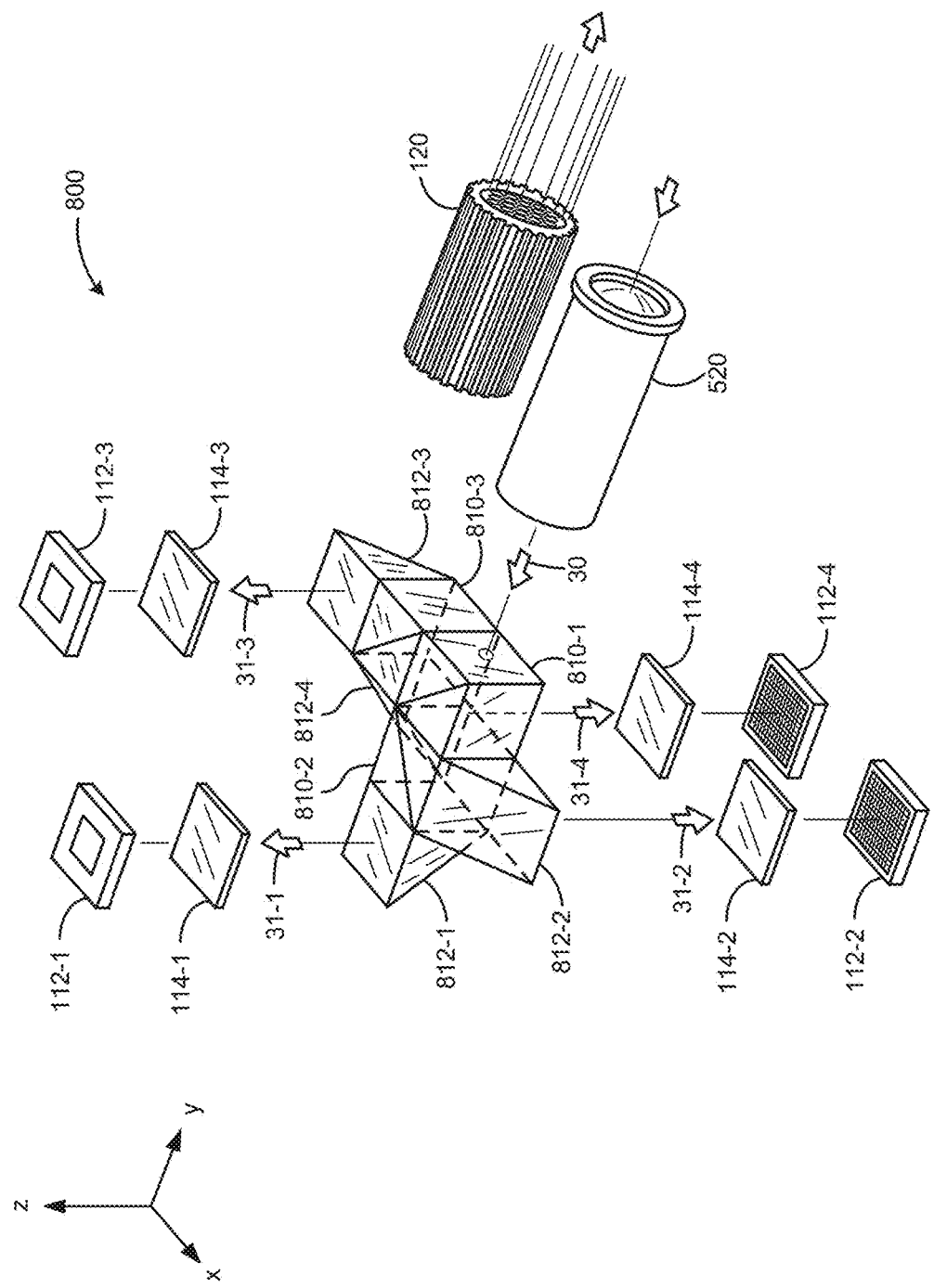
FIG. 8 is an exploded schematic view of a multi-sensor simultaneous capture hyperspectral imaging device, according to some implementations.

In some implementations, the method includes capturing (404) the plurality of images of the tissue of interest at an imaging system (e.g., imaging system 100, FIG. 1; coaxial imaging system 500 employing a beam steering element, FIG. 5; single-sensor imaging system 700 employing photo-sensor and filter arrays, FIG. 7; or concurrent capture imaging system 800, FIG. 8).

In some implementations, the imaging system captures (406) all of the plurality of images concurrently (e.g., when using a single-sensor imaging system 700 employing photo-sensor and filter arrays, FIG. 7; or concurrent capture imaging system 800 employing eight or more image sensors, FIG. 8).

In some implementations, hyperspectral imaging system captures (408) a first subset of the plurality of images concurrently at a first time point, and captures a second subset of the plurality of images at a second time point other than the first time point. For example, a concurrent capture imaging system (e.g., system 800 in FIG. 8) concurrently captures four images, one each at photo-sensors 112-1 to 112-4, each image at a different spectral band in the predetermined set of eight to ten spectral bands, in a first capture event. The concurrent capture imaging system then concurrently captures four more images, one each at photo-sensors 112-1 to 112-4, each image at a different spectral band in the predetermined set of eight to ten spectral bands, in a second capture event. As such, the concurrent capture imaging system captures images at eight of the predetermined set of eight to ten spectral bands between the first and second capture events. In some implementations, more than three capture events (e.g., three, four, or five capture events) can be used to capture images at all the predetermined set of eight to twelve spectral bands.

In some implementations, collecting the hyperspectral image includes illuminating the tissue of the subject with a first light (e.g., with light source 120 in FIGS. 1B, 5, 6, and 8), the first light including a first subset of spectral bands in the predetermined set of spectral bands. In some implementations, the light used to illuminate the region of interest is polarized to improve the signal-to-noise ratio of backscattered light detected by the imaging system. Use of a polarizing filter, orthogonal to a polarization of an illuminating light, in front of the detector reduces non-polarized ambient light from the detected signal.

In some implementations, capturing the hyperspectral image includes concurrently capturing a first subset of images in the plurality of images while illuminated with light corresponding to the spectral bands being captured, each respective image in the first plurality of images captured at a unique spectral band in the first plurality of spectral bands. In other words, images are captured at multiple spectral bands while the region of interest is illuminated with matching light.

In some implementations, each respective image in the first subset of images (e.g., each image 234 in hyperspectral image series A 242 in FIG. 2) is captured with a unique optical detector in a plurality of optical detectors (e.g., with a respective optical detector 112 in a concurrent capture imaging system 800 as illustrated in FIG. 8). For example, in some embodiments, each optical detector 112 is covered with a respective filter 114, allowing light corresponding to a unique spectral band in the first plurality of spectral bands to pass to the detector 112. In this fashion, the images concurrently collected by each of the optical detectors 112 are combined to form a portion of, or the entirety of, image series A 242.

In some implementations, e.g., when images of the subject are captured at less than all of the wavelengths in the predetermined set of spectral bands when illuminated with the first light, the method further includes illuminating the tissue with a second light (e.g., with light source 120 in FIGS. 1B, 5, 6, and 8), the second light including a second subset of spectral bands in the predetermined set of spectral bands, e.g., where the second subset of spectral bands is other than the first subset of spectral bands.

In some implementations, the first light and the second light are irradiated from separate light sources. In some implementations, the light used to illuminate the region of interest is polarized to improve the signal-to-noise ratio of backscattered light detected by the imaging system. Use of a polarizing filter, orthogonal to the polarization of the illuminating light, in front of the detector reduces non-polarized ambient light and light reflected directly off the surface being images from the detected signal.

In some implementations, collecting the hyperspectral image includes concurrently collecting a second subset of images in the plurality of images of the region of interest of the subject (e.g., images 243 in image series A 242 in FIG. 2) while illuminated by the second light, each respective image in the second subset of images collected at a unique spectral band in the second subset of spectral bands. In other words, a second set of images is collected at multiple spectral bands while the region of interest is illuminated with matching light. The second set of images complements the first set of images, such that all images required for a hyperspectral image series (e.g., series A 242 in FIG. 2) are collected between the first and second set of images.

In some implementations, each respective image in the first subset of images is collected with a unique optical detector in a plurality of optical detectors, each respective image in the second subset of images is collected with unique optical detector in the plurality of optical detectors, and at least one optical detector in the plurality of optical detectors collects a respective image in the first subset of images and a respective image in the second subset of images. In other words, in some implementations, an imaging system having more than one imaging sensor (e.g., a concurrent capture imaging system 800, as illustrated in FIG. 8) is used, and at least one of the optical detectors (e.g., optical detector 112-1 in FIG. 8) is used to collect a first image (e.g., in the first subset of images) at a first spectral band and then a second image (e.g., in the second subset of images) at a second spectral band.

In some embodiments, the optical detector (e.g., optical detector 112-1 in FIG. 8) is covered by a dual bandpass filter (e.g., filter 114-1 in FIG. 8) that allows light of the first spectral band and light of the second spectral band to pass through to the optical detector. In this fashion, the region of interest of the subject is first illuminated with light that includes the first spectral band, but not the second spectral band, and the first image is captured by the optical detector (e.g., optical detector 112-1 in FIG. 8). Then, the region of interest of the subject is illuminated with light that includes the second spectral band, but not the first spectral band, and the second image is captures by the optical detector (e.g., the same optical detector 112-1 in FIG. 8). Thus, the optical detector (e.g., optical detector 112-1 in FIG. 8) is used to collect two images, at different spectral bands, of the hyperspectral image series (e.g., image 243-B and image 243-C in image series A 242, represented in FIG. 2).

In some implementations, each respective optical detector in the plurality of optical detectors (e.g., each of optical detectors 112-1 to 112-4, illustrated in FIG. 8) collects (428) a respective image in the first subset of images and a respective image in the second subset of images. In some implementations, each optical detector (e.g., optical detectors 112 in FIG. 8) is covered by a unique dual band pass filter (e.g., filters 114 in FIG. 8). In this fashion, the region of interest of the subject is illuminated with a first light having spectral bands corresponding to one of the band passes on each of the filters, but not light having spectral bands corresponding to the other band passes on each of the filters (e.g., light emitted from first light source 120-1). A first sub-set of images is collected while the location is illuminated with the first light. Then, the location is illuminated with a second light having spectral bands corresponding to the other spectral band pass on each of the filters, but not light having wavelengths corresponding to the first band pass on each of the filters (e.g., light emitted from second light source 120-2). A second sub-set of images is then collected while the location is illuminated with the second light.

In some implementations, the first subset of images is four images and the second subset of images is four images. For example, in some implementations, an imaging system having four optical detectors (e.g., concurrent capture imaging system 800 in FIG. 8) is used. Each optical detector (e.g., optical detectors 112) collects an image in the first subset and an image in the second subset of images, to form a hyperspectral image series consisting of eight images.

In some implementations, each respective optical detector in the plurality of optical detectors (e.g., optical detectors 112 of a hyperspectral imaging system such as the concurrent capture imaging system 800 illustrated in FIG. 8) is covered by a dual-band pass filter (e.g., filters 114 in FIG. 8).

In some implementations, each respective optical detector is covered by a triple bandpass filter, enabling use of a third light source and collection of three sets of images at unique spectral bands. For example, four optical detectors can collect images at up to twelve unique spectral bands, when each detector is covered by a triple bandpass filter.

In some implementations, each respective optical detector is covered by a quad-bandpass filter, enabling use of a fourth light source and collection of four sets of images at unique spectral bands. For example, four optical detectors can collect images at up to sixteen unique spectral bands, when each detector is covered by a quad band-pass filter. In yet other implementations, bandpass filters allowing passage of five, six, seven, or more bands each can be used to collect larger sets of unique spectral bands.

The method further includes, registering (411), using the processor, the plurality of images on a pixel-by-pixel basis, to form a plurality of registered images of the tissue. In some implementations, registering includes storing each respective image at a corresponding memory location (e.g., in memory 220), and comparing, on a pixel-by-pixel basis (e.g., with processor 210) each pixel of the respective images to produce the plurality of registered images. In some implementations, one or more registered images is then stored at a corresponding memory location.

In some implementations (e.g., where the methods includes capturing images at an imaging system), the method includes performing spectral analysis at the imaging system 100 (e.g., the system captures and then processes the image). In other implementations, the imaging system 100 captures the images, and then transmits the images, or pre-processed data (e.g., a hypercube), to an external processing device (e.g., local processing device 24 or remote processing server 52) for spectral analysis.

The electronic device then performs (412) spectral analysis at a plurality of points in a two-dimensional area of the plurality of registered images of the tissue (e.g., evaluates absorbance at the same points or groups of points in each of the images captured at the predetermined set of spectral bands), the spectral analysis including determining approximate values of oxyhemoglobin levels and deoxyhemoglobin levels at each respective point in the plurality of points.

In some implementations, the device performs spectral analysis by resolving (414) absorption signals at each point in the plurality of points, accounting for a melanin contribution and loss of signal from diffuse scattering at each point in the plurality of points, to form a plurality of corrected absorption signals, and determining approximate values of oxyhemoglobin levels and deoxyhemoglobin levels from the corrected absorption signals at each point in the plurality of points.

Algorithms for determining oxyhemoglobin and deoxyhemoglobin from hyperspectral data are known in the art. For example, exemplary processing algorithms are described in U.S. Pat. No. 8,644,911, the disclosure of which is hereby expressly incorporated by reference, in its entirety, for all purposes. Advantageously, the present disclosure reduces the computational burden of determining oxyhemoglobin levels and deoxyhemoglobin, when using algorithms disclosed in the art, by facilitating accurate determination with significantly few wavelengths (e.g., using eight to ten wavelengths rather than fifteen or more).

In some implementations, the electronic device (e.g., imaging device 100, local processing device 24, or remote processing server 52) models (416) the contribution provided by melanin and the losses provided by diffuse scattering (e.g., background contributions) to the plurality of tissue oxygenation measurements collectively as a second order polynomial. For example, U.S. Pat. No. 8,644,911 describes an exemplary method for modeling contributions from melanin and losses provided by diffuse scattering as a second order polynomial. In other implementations, background contributions (e.g., melanin absorption and loss due to diffuse scattering) may be modeled according to any linear or non-linear model known in the art.

In some implementations, the predetermined set of spectral bands includes eight spectral bands having central wavelengths of about 510 nm, 530 nm, 540 nm, 560 nm, 580 nm, 590 nm, 620 nm, and 660 nm. In some implementations the predetermined set is a set of twelve spectral bands, including these eight. In some implementations the predetermined set is a set of eleven spectral bands, including these eight. In some implementations the predetermined set is a set of ten spectral bands, including these eight. In some implementations the predetermined set is a set of nine spectral bands, including these eight. In some implementations, the predetermined set only includes these eight spectral bands.

In a specific implementation, the predetermined set of spectral bands includes eight spectral bands having central wavelengths of 510±2 nm, 530±2 nm, 540±2 nm, 560±2 nm, 580±2 nm, 590±2 nm, 620±2 nm, and 660±2 nm, and each spectral band in the eight spectral bands has a full width at half maximum of less than 10 nm (408). In some embodiments, the spectral band with a central wavelength of 660±2 nm is collected as a wider spectral band (e.g., has a full width at half maximum ("FWHM") that is greater than the FWHM of the other spectral bands in the predetermined set) to account for the lower sensitivity of many optical detectors to radiation near this wavelength, relative to the sensitivity to shorter wavelengths in the visible spectrum. In some embodiments, the spectral band having the central wavelength of 660±2 nm has a full width at half maximum of less than 20 nm.

In some embodiments, the predetermined set of spectral bands includes from seven to twelve spectral bands (e.g., seven, eight, nine, ten, eleven, or twelve wavelengths) that each have a central wavelength in the spectral region of from 490 nm to 670 nm, where at least seven of the spectral bands in the predetermined set have central wavelengths selected from 510±3 nm, 530±3 nm, 540±3 nm, 560±3 nm, 580±3 nm, 590±3 nm, 620±3 nm, and 660±3 nm. In some embodiments, each of the spectral bands in the predetermined set has a full width at half maximum of less than 20 nm. In some embodiments, each of the spectral bands in the predetermined set that has a central wavelengths of 640 nm or less has a full width at half maximum of less than 15 nm (e.g., and each spectral band having a central wavelength of more than 640 nm has a full width at half maximum of less than 15 nm).

In some implementations, the predetermined set of spectral bands includes eight spectral bands having central wavelengths of about 520 nm, 540 nm, 560 nm, 580 nm, 590 nm, 610 nm, 620 nm, and 640 nm. In some implementations the predetermined set is a set of twelve spectral bands, including these eight. In some implementations the predetermined set is a set of eleven spectral bands, including these eight. In some implementations the predetermined set is a set of ten spectral bands, including these eight. In some implementations the predetermined set is a set of nine spectral bands, including these eight. In some implementations, the predetermined set only includes these eight spectral bands.

In another specific implementation, the predetermined set of spectral bands includes eight spectral bands having central wavelengths of 520±2 nm, 540±2 nm, 560±2 nm, 580±2 nm, 590±2 nm, 610±2 nm, 620±2 nm, and 640±2, and each spectral band in the eight spectral bands has a full width at half maximum of less than 10 nm (409).

In some embodiments, the predetermined set of spectral bands includes from seven to twelve spectral bands (e.g., seven, eight, nine, ten, eleven, or twelve wavelengths) that each have a central wavelength in the spectral region of from 490 nm to 670 nm, where at least seven of the spectral bands in the predetermined set have central wavelengths selected from 520±3 nm, 540±3 nm, 560±3 nm, 580±3 nm, 590±3 nm, 610±3 nm, 620±3 nm, and 640±3. In some embodiments, each of the spectral bands in the predetermined set has a full width at half maximum of less than 20 nm. In some embodiments, each of the spectral bands in the predetermined set that has a central wavelengths of 640 nm or less has a full width at half maximum of less than 15 nm (e.g., and each spectral band having a central wavelength of more than 640 nm has a full width at half maximum of less than 15 nm).

In some implementations, the predetermined set of spectral bands consists of eight spectral bands having central wavelengths of about 500 nm, 530 nm, 545 nm, 570 nm, 585 nm, 600 nm, 615 nm, and 640 nm. In some implementations the predetermined set is a set of twelve spectral bands, including these eight. In some implementations the predetermined set is a set of eleven spectral bands, including these eight. In some implementations the predetermined set is a set of ten spectral bands, including these eight. In some implementations the predetermined set is a set of nine spectral bands, including these eight. In some implementations, the predetermined set only includes these eight spectral bands.

In another specific implementation, the predetermined set of spectral bands includes eight spectral bands having central wavelengths of 500±2 nm, 530±2 nm, 545±2 nm, 570±2 nm, 585±2 nm, 600±2 nm, 615±2 nm, and 640±2 nm, and each spectral band in the eight spectral bands has a full width at half maximum of less than 10 nm (410).

In some embodiments, the predetermined set of spectral bands includes from seven to twelve spectral bands (e.g., seven, eight, nine, ten, eleven, or twelve wavelengths) that each have a central wavelength in the spectral region of from 490 nm to 670 nm, where at least seven of the spectral bands in the predetermined set have central wavelengths selected from 500±3 nm, 530±3 nm, 545±3 nm, 570±3 nm, 585±3 nm, 600±3 nm, 615±3 nm, and 640±3 nm. In some embodiments, each of the spectral bands in the predetermined set has a full width at half maximum of less than 20 nm. In some embodiments, each of the spectral bands in the predetermined set that has a central wavelengths of 640 nm or less has a full width at half maximum of less than 15 nm (e.g., and each spectral band having a central wavelength of more than 640 nm has a full width at half maximum of less than 15 nm).

In some implementations, the predetermined set of spectral bands includes eight spectral bands having central wavelengths of about 520 nm, 540 nm, 560 nm, 580 nm, 590 nm, 610 nm, 620 nm, and 660 nm. In some implementations the predetermined set is a set of twelve spectral bands, including these eight. In some implementations the predetermined set is a set of eleven spectral bands, including these eight. In some implementations the predetermined set is a set of ten spectral bands, including these eight. In some implementations the predetermined set is a set of nine spectral bands, including these eight. In some implementations, the predetermined set only includes these eight spectral bands.

In another specific implementation, the predetermined set of spectral bands includes eight spectral bands having central wavelengths of 520±2 nm, 540±2 nm, 560±2 nm, 580±2 nm, 590±2 nm, 610±2 nm, 620±2 nm, and 660±2, and the spectral bands having central wavelengths of 520±2 nm, 540±2 nm, 560±2 nm, 580±2 nm, 590±2 nm, 610±2 nm, and 620±2 nm have a full width at half maximum of less than 15 nm, and the spectral band having the central wavelength of 660±2 nm has a full width at half maximum of less than 20 nm.

In a specific implementation, the predetermined set of eight to twelve spectral bands includes eight spectral bands having central wavelengths of 520±3 nm, 540±3 nm, 560±3 nm, 580±3 nm, 590±3 nm, 610±3 nm, 620±3 nm, and 660±3, and the spectral bands having central wavelengths of 520±3 nm, 540±3 nm, 560±3 nm, 580±3 nm, 590±3 nm, 610±3 nm, and 620±3 nm have a full width at half maximum of less than 15 nm, and the spectral band having the central wavelength of 660±3 nm has a full width at half maximum of less than 20 nm.

In a specific implementation, the predetermined set of eight to twelve spectral bands includes eight spectral bands having central wavelengths of 520±2 nm, 540±2 nm, 560±2 nm, 580±2 nm, 590±2 nm, 610±2 nm, 620±2 nm, and 660±2, and the spectral bands having central wavelengths of 520±2 nm, 540±2 nm, 560±2 nm, 580±2 nm, 590±2 nm, 610±2 nm, and 620±2 nm have a full width at half maximum of less than 15 nm, and the spectral band having the central wavelength of 660±2 nm has a full width at half maximum of less than 20 nm.

In a specific implementation, the predetermined set of eight to twelve spectral bands includes eight spectral bands having central wavelengths of 520±1 nm, 540±1 nm, 560±1 nm, 580±1 nm, 590±1 nm, 610±1 nm, 620±1 nm, and 660±1, and the spectral bands having central wavelengths of 520±1 nm, 540±1 nm, 560±1 nm, 580±1 nm, 590±1 nm, 610±1 nm, and 620±1 nm have a full width at half maximum of less than 15 nm, and the spectral band having the central wavelength of 660±1 nm has a full width at half maximum of less than 20 nm.

In a specific implementation, the predetermined set of eight to twelve spectral bands includes eight spectral bands having central wavelengths of 520 nm, 540 nm, 560 nm, 580 nm, 590 nm, 610 nm, 620 nm, and 660, and the spectral bands having central wavelengths of 520 nm, 540 nm, 560 nm, 580 nm, 590 nm, 610 nm, and 620 nm have a full width at half maximum of less than 15 nm, and the spectral band having the central wavelength of 660 nm has a full width at half maximum of less than 20 nm.

In some embodiments, the predetermined set of spectral bands includes from seven to twelve spectral bands (e.g., seven, eight, nine, ten, eleven, or twelve wavelengths) that each have a central wavelength in the spectral region of from 490 nm to 670 nm, where at least seven of the spectral bands in the predetermined set have central wavelengths selected from 520±3 nm, 540±3 nm, 560±32 nm, 580±3 nm, 590±3 nm, 610±3 nm, 620±3 nm, and 660±3. In some embodiments, each of the spectral bands in the predetermined set has a full width at half maximum of less than 20 nm. In some embodiments, each of the spectral bands in the predetermined set that has a central wavelengths of 640 nm or less has a full width at half maximum of less than 15 nm (e.g., and each spectral band having a central wavelength of more than 640 nm has a full width at half maximum of less than 15 nm).

Use of the term "about," for purposes of this particular set of spectral bands, refers to a central wavelength that is no more than 5 nm from the recited wavelength. In some implementations, each spectral band in the set has a central wavelength that is no more than 4 nm from the recited wavelength. In some implementations, each spectral band in the set has a central wavelength that is no more than 3 nm from the recited wavelength. In some implementations, each spectral band in the set has a central wavelength that is no more than 2 nm from the recited wavelength. In some implementations, each spectral band in the set has a central wavelength that is no more than 1 nm from the recited wavelength. In some implementations, each spectral band in the set has the recited central wavelength.

In some implementations, each respective spectral band has a full width at half maximum of less than 20 nm. In some implementations, each respective spectral band has a full width at half maximum of less than 15 nm (422). In some implementations, each respective spectral band has a full width at half maximum of less than 10 nm. In some implementations, each respective spectral band has a full width at half maximum of less than 5 nm (424). In some implementations, each respective spectral band has a full width at half maximum of less than 4 nm. In some implementations, each respective spectral band has a full width at half maximum of less than 3 nm. In some implementations, each respective spectral band has a full width at half maximum of less than 2 nm. In some implementations, each respective spectral band has a full width at half maximum of no more than 1 nm.

In some implementations, the data set of images acquired at the predetermined set of spectral bands is obtained by capturing the plurality of images (e.g., of a tissue of interest) using the same device that registers the images, and/or performs the spectral analysis. In other implementations, the images are acquired using a spectral imaging system (e.g., a hyperspectral camera) and the image registration and/or spectral analysis is performed at a second electronic device (e.g., a computer, server, portable electronic device, such as a tablet or smart phone).

In some implementations, all of the images forming the data set (e.g., the images acquired at the predetermined set of spectral bands) are captured concurrently (e.g., using an imaging device having multiple optical sensors and/or a filter array positioned in front of a multi-pixel optical detector. Exemplary embodiments of imaging systems that can be used for concurrent capture of images at multiple spectral bands are described below.

In some implementations, a first subset of the plurality of images forming the data set (e.g., the images acquired at the predetermined set of spectral bands) is captured concurrently at a first time point and a second subset of the plurality of images forming the data set is captured concurrently at a second time point, other than the first time point. Exemplary embodiments of imaging systems that can be used for concurrent capture of images at multiple spectral bands are described below.

In some implementations, the spectral analysis includes resolving absorption signals at each respective point (e.g., pixel or bin of pixels) in a plurality of points (e.g., pixels or bins of pixels) in each image of the data set; accounting for a melanin contribution and loss of signal from diffuse scattering at each point in the plurality of points, to generate corrected absorption signals at each point (e.g., pixel or bin of pixels), and then determining approximate values of oxyhemoglobin levels and deoxyhemoglobin levels from the corrected absorption signals at each point (e.g., pixel or bin of pixels). In some implementations, absorptive contribution provided by melanin and signal losses caused by diffuse scattering to the plurality of tissue oxygenation measurements are collectively modeled as a second order polynomial. Exemplary methods for accounting for the absorptive contributions of melanin and loss of signal from diffuse scattering are described in U.S. Pat. No. 8,644,911, the disclosure of which is hereby incorporated by reference, in its entirety, for all purposes.

In some implementations, the imaging system is handheld and battery operated. This is accomplished by reducing the power budget needed to operate the hyperspectral imaging system. In non-limiting examples, the power budget is reduced by one or more of: using orthogonal polarizing filters in front of the illumination source (e.g., light source 120 in FIG. 1B; illumination subsystem 510 in FIG. 5; or illumination source 120 in FIG. 8) and detection source (e.g., sensor module 110 in FIG. 1B, optical detectors 112 in FIG. 5 and FIG. 8); using matched narrowband irradiation sources (e.g., LED light sources emitting one or more narrow spectral bands) and detection filters (e.g., notch or other narrow band filters); using capacitors to store large current bursts needed for efficient illumination of the target (e.g., a tissue); and reducing the number of spectral bands required to construct a high resolution hyperspectral image (e.g., using only eight to ten spectral bands).

In some embodiments, the method further includes providing a therapy for a medical condition based on the tissue oxygenation measurements. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, an inflammatory response, or a cancer.

In some implementations, the method further includes providing a diagnosis of a medical condition based on the tissue oxygenation measurements. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some implementations, the method further includes providing a prognosis for progression, regression, recurrence, or disease-free survival of a medical condition based on the tissue oxygenation measurements. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some implementations, the method further includes assigning a therapy for a medical condition based on the tissue oxygenation measurements. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some embodiments, the method further includes providing a preventative therapy for a medical condition based on the tissue oxygenation measurements. For example, hyperspectral analysis of diabetic patients may identify hot spots indicating emerging foot ulcers that have not yet been ulcerated. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In one embodiment, the disclosure provides an electronic device with one or more processors, memory, and one or more programs (e.g., stored in the memory) configured to be executed by the one or more processors. The one or more programs include instructions for obtaining a data set including a plurality of images of a tissue of interest, each respective image in the plurality of images resolved at a different spectral band in a predetermined set of eight to twelve spectral bands, and including an array of pixel (or pixel bin) values. The one or more programs also include instructions for registering, using the processor, the plurality of images on a pixel-by-pixel (or pixel bin by pixel bin) basis, to form a plurality of registered images of the tissue. The one or more programs also provide instructions for performing spectral analysis at a plurality of points in a two-dimensional area of the plurality of registered images of the tissue, the spectral analysis including determining approximate values of oxyhemoglobin levels and deoxyhemoglobin levels at each respective pixel (or pixel bin) in the plurality of pixels (or pixel bins), where the predetermined set of eight to twelve spectral bands includes spectral bands having central wavelengths of: 520±3 nm, 540±3 nm, 560±3 nm, 580±3 nm, 590±3 nm, 610±3 nm, 620±3 nm, and 660±3 nm, and where the spectral bands having central wavelengths of 520±3 nm, 540±3 nm, 560±3 nm, 580±3 nm, 590±3 nm, 610±3 nm, and 620±3 nm have a full width at half maximum of less than 15 nm, and the spectral band having the central wavelength of 660±3 nm has a full width at half maximum of less than 20 nm.

In some implementations, the electronic device is an imaging system that includes one or more photo-sensors in electronic communication with the one or more processors and configured to resolve light of the predetermined set of eight to twelve spectral bands, and where the instructions for obtaining the data set include instructions for capturing the plurality of images of the tissue of interest using the one or more photo-sensors. In some implementations, the plurality of images is captured concurrently. In some implementations, a first subset of the plurality of images is captured concurrently at a first time point and a second subset of the plurality of images is captured concurrently at a second time point (e.g., after the first time point).

In some implementations, the instructions include resolving absorption signals at each respective point in the plurality of points (e.g., each pixel or pixel bin), accounting for a melanin contribution and loss of signal from diffuse scattering at each respective point in the plurality of points (e.g., each pixel or pixel bin), to form a plurality of corrected absorption signals, and determining approximate values of oxyhemoglobin levels and deoxyhemoglobin levels from the corrected absorption signals at each respective point in the plurality of points (e.g., each pixel or bin of pixels). In some implementations, absorptive contribution provided by melanin and signal losses caused by diffuse scattering to the plurality of tissue oxygenation measurements are collectively modeled as a second order polynomial. Exemplary methods for accounting for the absorptive contributions of melanin and loss of signal from diffuse scattering are described in U.S. Pat. No. 8,644,911, the disclosure of which is hereby incorporated by reference, in its entirety, for all purposes.

In one embodiment, the disclosure provides a non-transitory computer readable medium storing one or more programs that include instructions, which when executed by an electronic device having a processor and memory, cause the electronic device to obtain a data set including a plurality of images of a tissue of interest, each respective image in the plurality of images resolved at a different spectral band in a predetermined set of eight to twelve spectral bands, and including an array of pixel (or pixel bin) values. The one or more programs also include instructions causing the device to register, using the processor, the plurality of images on a pixel-by-pixel (or pixel bin by pixel bin) basis, to form a plurality of registered images of the tissue. The one or more programs also provide instructions that cause the device to perform spectral analysis at a plurality of points in a two-dimensional area of the plurality of registered images of the tissue, the spectral analysis including determining approximate values of oxyhemoglobin levels and deoxyhemoglobin levels at each respective pixel (or pixel bin) in the plurality of pixels (or pixel bins), where the predetermined set of eight to twelve spectral bands includes spectral bands having central wavelengths of: 520±3 nm, 540±3 nm, 560±3 nm, 580±3 nm, 590±3 nm, 610±3 nm, 620±3 nm, and 660±3 nm, and where the spectral bands having central wavelengths of 520±3 nm, 540±3 nm, 560±3 nm, 580±3 nm, 590±3 nm, 610±3 nm, and 620±3 nm have a full width at half maximum of less than 15 nm, and the spectral band having the central wavelength of 660±3 nm has a full width at half maximum of less than 20 nm.

In some implementations, the non-transitory computer-readable medium, when executed by an imaging system having one or more photo-sensors in electronic communication with the one or more processors and configured to resolve light of the predetermined set of eight to twelve spectral bands, cause the imaging system to capture the plurality of images of the tissue of interest using the one or more photo-sensors. In some implementations, the plurality of images is captured concurrently. In some implementations, a first subset of the plurality of images is captured concurrently at a first time point and a second subset of the plurality of images is captured concurrently at a second time point (e.g., after the first time point).

Figure 6:
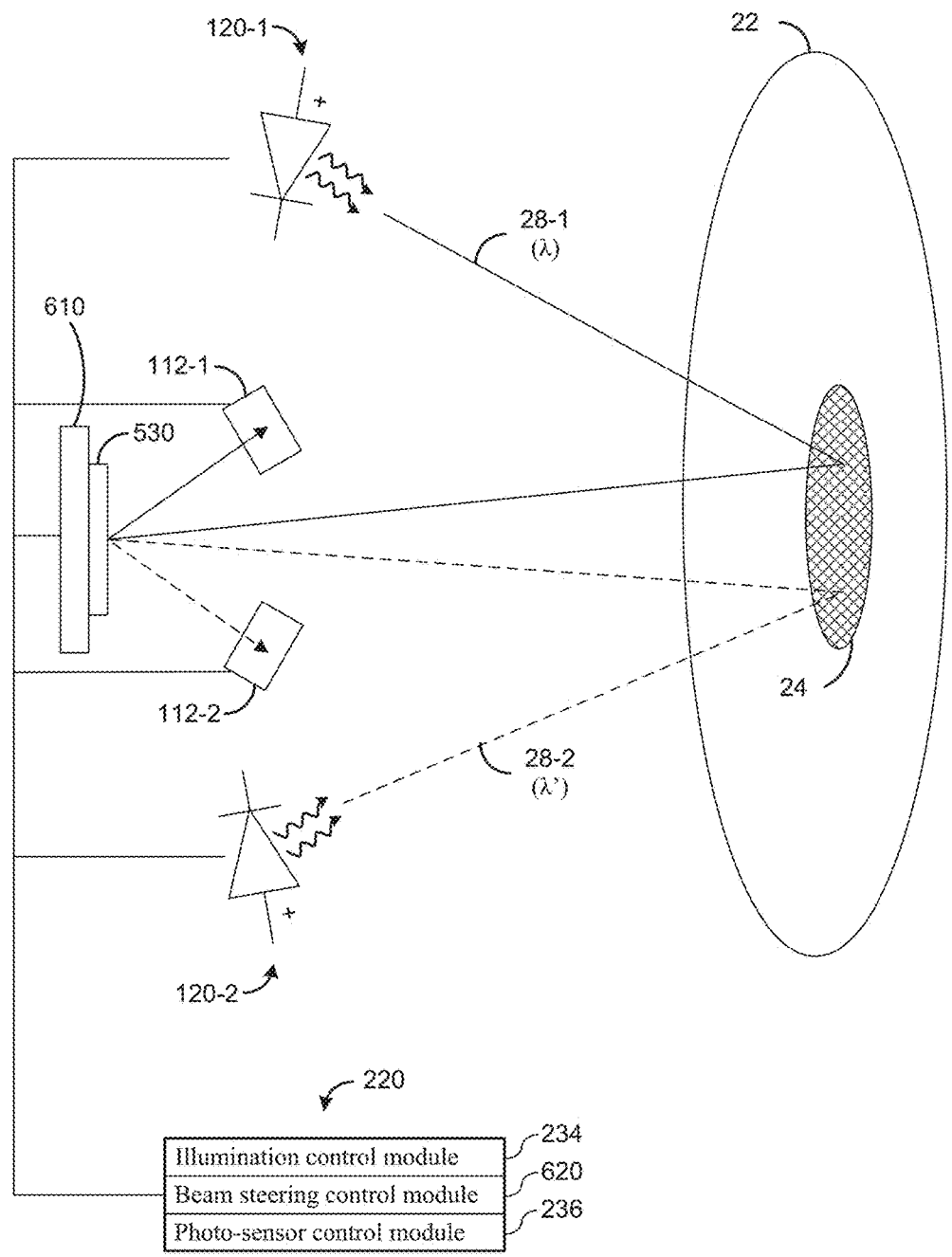
FIG. 6 is a schematic illustration of the light path for a captured hyperspectral/multispectral image, according to some implementations employing a co-axial hyperspectral imager with a beam-steering element.

In some implementations, the instructions cause the device to resolve absorption signals at each respective point in the plurality of points (e.g., each pixel or pixel bin), accounting for a melanin contribution and loss of signal from diffuse scattering at each respective point in the plurality of points (e.g., each pixel or pixel bin), to form a plurality of corrected absorption signals, and determining approximate values of oxyhemoglobin levels and deoxyhemoglobin levels from the corrected absorption signals at each respective point in the plurality of points (e.g., each pixel or bin of pixels). In some implementations, absorptive contribution provided by melanin and signal losses caused by diffuse scattering to the plurality of tissue oxygenation measurements are collectively modeled as a second order polynomial. Exemplary methods for accounting for the absorptive contributions of melanin and loss of signal from diffuse scattering are described in U.S. Pat. No. 8,644,911, the disclosure of which is hereby incorporated by reference, in its entirety, for all purposes Exemplary Implementations In some implementations, the methods described herein are performed using imaging systems with unique internal optical architectures that allow for faster image acquisition and data processing. FIGS. 5 and 6 illustrate one such implementation in which the imaging system has a beam steering element configured to steer light to one of a plurality of optical detectors, each of which are configured to resolve light of a specific spectral band. FIG. 7 illustrates the principle behind a second such implementation, in which the imaging system employs a photo-sensor array having a plurality of photo-sensors, covered by a spectral filter array having a plurality of filter elements. This implementation enables capture of images at all wavelengths necessary to construct a hyperspectral image with a single exposure. FIG. 8 illustrates the principle behind a third such implementation, in which the imaging system concurrently captures multiple images at multiple spectral bands by splitting the incidental light and directing it to multiple optical detectors.

FIG. 5 illustrates the use of an imaging system including a beam steering element having a plurality of operating modes, which directs light of different wavelengths to distinct optical detectors from a common point of origin, thus maintaining co-axial alignment between images captured by the respective optical detectors. In one implementation, the imaging device includes a housing having an exterior and an interior and at least one objective lens attached to or within the housing. The at least one objective lens is disposed in an optical communication path comprising an originating end and a terminating end. The imaging device also includes a beam steering element within the interior of the housing. The beam steering element is in optical communication with the at least one objective lens and is positioned at the terminating end of the optical communication path. The beam steering element is characterized by a plurality of operating modes. Each respective operating mode in the plurality of operating modes causes the beam steering element to be in optical communication with a different optical detector.

According to certain embodiments, the co-axial imaging device 500 includes: an illumination subsystem 510 containing one or more light sources 120; an objective lens assembly 520 housed in a chassis 522 that anchors the lens assembly with respect to other components of the optical assembly; an optional stray light shield 524; a beam steering element 530 in electrical communication, and optionally mounted on, a motherboard 540 in electrical communication with one or more CPU(s) (not shown); and an imager subsystem comprising a plurality of optical detectors 112 in electrical communication with the motherboard 540 by way of a flex circuit or wire 542.

In one embodiment, an optical communication path is created when radiation emitted from one or more of the lights 120 of the illumination subsystem 510 illuminates a tissue of the subject (not shown) and is backscattered to an objective lens assembly 520, which focuses the light on a beam steering element 530 having a plurality of operating modes. When positioned in a respective operating mode, the beam steering element 530 reflects the light onto one of the plurality of optical detectors 112, which is configured to capture an image of the surface of the subject at one or more specific wavelengths.

Each optical detector 112 in the imager subsystem is optionally covered by an optical filter (e.g., a detector filter), which allows light of a predetermined wavelength to pass through to the detector. In one embodiment, one or more of the light sources 120 is matched to a filter covering an optical detector 112, e.g., the light emits radiation at wavelength that is capable of passing through the corresponding filter. When respective light sources 120 in a plurality of light sources are matched to corresponding detector filters in a plurality of detector filters, the beam steering element 530 functions to direct radiation emitted by a respective light source 120 to the corresponding optical detector 112 covered by a matching filter. The beam steering element 530 is configured to have a plurality of operating modes, each of which directs light backscattered from the tissue of the subject to a different optical detector 112.

The internal hardware of co-axial imaging device 500 is mounted in housing 552, according to some embodiments. Optionally, housing 552 includes dock 560 for attaching portable device 562 to housing 552. Optionally, portable device 562 contains a display, preferably a touch-screen display, for displaying images acquired by internal hardware of a co-axial imaging device 500.

Referring to FIG. 6, light 28 having a first wavelength (k), emitted from a light source 120, reflects or backscatters from a region of interest (24; ROI) on an object or subject 22. The light 28 then passes through the objective lens assembly (not shown) and is directed by a beam steering element 530, positioned in a first operating mode in a plurality of operating modes, towards an optical detector 112 configured to resolve light of the first wavelength (k). In certain embodiments, the beam steering element is positioned in its respective operating modes through the use of an actuator 610 capable of adjust tip and tilt angles of the beam steering element.

In some embodiments, control modules, stored in the system memory 220 control: the illumination, via an illumination control module 234, the direction of the beam towards one or more optical detectors 112 via a beam steering control module 620, and the image exposure time and optical detectors themselves via an optical detector control module 236. The beam steering control module 620 directs actuator 610 to place the beam steering element 530 in various operating modes, each of which is in optical communication with one of the optical detectors 112.

For example, to collect images of an object 22 for hyperspectral/multispectral analysis at two different wavelengths, k and k', the illumination control module 234 turns on a first light 120-1, emitting light 28-1 at a first wavelength (k), illuminating a region of interest (ROI) 24 on the subject 22. Reflected or backscattered light 120-1 from the subject 22 enters the objective lens or assembly thereof (not shown) and hits the beam steering element 530, placed in a first operating mode by an actuator 610 controlled by the beam steering control module 620, which redirects the light onto an optical detector 112-1 configured to resolve light of wavelength λ. The illumination control module 234 then turns off the first light 120-1 and turns on a second light 120-2, emitting light 28-2 at a second wavelength (k'), illuminating the ROI 24. Concurrently, the beam steering control module 620 instructs the actuator 610 to place the beam steering element 530 in a second operating mode, which is in optical communication with a second optical detector 112-2 configured to resolve light of wavelength k'. Thus, when reflected or backscattered light 28-2 hits the beam steering element 530, the light 28-2 is redirected onto the second optical detector 112-2.

The beam steering element 530 can be one or more reflective elements capable of redirecting the incident beam in one or more directions toward the detector(s). In some embodiments, the beam steering element 530 is an element that reflects light in one or more directions (e.g., a mirror element). In a particular embodiment the beam steering element is a plain mirror capable of reflecting light over a wide range of wavelengths. In another particular embodiment, the beam steering element is an array of mirrors, for example an array of micromirrors.

In one embodiment, the beam steering element consists of more than one element and is capable of concurrently directing lights of different wavelengths in different directions. In specific embodiments, the beam steering element includes a first hot mirror and a second mirror positioned behind the hot mirror. The hot mirror is suitably coated to reflect light above or below a certain wavelength, while being transparent to light with lower or higher wavelengths, respectively.

Further implementations of the co-axial hyperspectral imaging strategy are disclosed in International Publication No. WO 2014/007869, the content of which is expressly incorporated herein by reference, in its entirety, for all purposes.

In some implementations, the method is performed using an imaging device including a photo-sensor array including a plurality of photo-sensors. Each photo-sensor provides a respective output. The device further comprises a spectral filter array having a plurality of filter elements. Each filter element is arranged to filter light received by a respective one or more of the photo-sensors. Each filter element is one of a plurality of filter-types. Each filter-type characterized by a unique spectral pass-band. The device further includes an interface module to select a plurality of subsets of photo-sensor outputs. Each such subset is associated with a single respective filter-type. The device comprises a control module that generates a hyperspectral data cube from the subsets of photo-sensor outputs by generating a plurality of images. Each such image is produced from a single corresponding subset of photo-sensor outputs in the plurality of photo-sensor outputs and so is associated with a corresponding filter-type in the plurality of filter-types.

FIG. 7 is an exploded schematic view of an implementation of an image sensor assembly for a single-sensor imaging device 700. The image sensor assembly includes a photo-sensory array 112 in combination with a filter array 114. In some implementations, the photo-sensory array 112 includes a plurality of photo-sensors. For example, detailed view 710 schematically shows, as a non-limiting example only, a number of photo-sensors 711 included in the photo-sensor array 112. Each photo-sensor 711 generates a respective electrical output by converting light incident on the photo-sensor.

The light incident on a particular photo-sensor 711 is filtered by a respective filter in the filter array 114. In some implementations, the filter array 114 is configured to include a plurality of filter elements. Each filter element is arranged to filter light received by a respective one or more of the plurality of photo-sensors in the photo-sensor array 112. Each filter element is also one of a plurality of filter-types, and each filter-type is characterized by a spectral pass-band different from the other filter-types. As such, the electrical output of a particular photo-sensor is associated with a particular spectral pass-band associated with the respective filter associated the particular photo-sensor 711.

For example, the detailed view 720 schematically shows, as a non-limiting example only, a number of filter-types A, B, C, D, E, F, G, H, and I are included in the filter array 114. In one implementation, at least two of filter types A, B, C, D, E, F, G, H, and I have different spectral pass-bands. For example, as illustrated in FIG. 7, filter elements 721*a*-1 and 721*a*-2 of filter types A and B, respectively, have different spectral pass-bands. In some implementations, at least two of filter types A, B, C, D, E, F, G, H, and I have the same spectral pass-band and at least two of filter types A, B, C, D, E, F, G, H, and I have different spectral pass-bands.

In some implementations, each filter-type A, B, C, D, E, F, G, H, and I has a spectral pass-band different from the others. In some implementations, the filter-types A, B, C, D, E, F, G, H, and I are arranged in a 3×3 grid that is repeated across the filter array 114. For example, as illustrated in FIG. 7, three filter elements 721*a*-1, 721*b*-1, 721*c*-1 of filter-type A are illustrated to show that instances of filter-type A are repeated in a uniform distribution across the filter array 114 such that the center-to-center distance d1 between two filters of the same type is less than 250 microns in some implementations. In some implementations, the center-to-center distance d1 between two filters of the same type is less than 100 microns.

Moreover, while nine filter-types are illustrated for example in FIG. 7, those skilled in the art will appreciate from the present disclosure that any number of filter types can be used in various implementations. For example, in some implementations 3, 5, 16 or 25 filter-types can be used in various implementations. Additionally and/or alternatively, while a uniform distribution of filter-types has been illustrated and described, those skilled in the art will appreciate from the present disclosure that, in various implementations, one or more filter-types may be distributed across a filter array in a non-uniform distribution. Additionally and/or alternatively, those skilled in the art will also appreciate that "white-light" or transparent filter elements may be included as one of the filter-types in a filter array.

FIG. 7 illustrates an advantage of the single-sensor imaging device. A single exposure of light 30 from a lens assembly is filtered by filter array 114 to form filtered light 32 that impinges upon sensor 112 and, from this single exposure, multiple images 243 of the same region 24 of a subject 22 are concurrently made. The imaging device 700 includes a photo-sensor array 112 including a plurality of photo-sensors 711. Each photo-sensor 711 provides a respective output. Imaging device 700 further includes a spectral filter array 114 having a plurality of filter elements 721. Each filter element 721 is arranged to filter light 30 received by a respective one or more of the plurality of photo-sensors 711. Each filter element 721 is one of a plurality of filter-types. For instance, in FIG. 7, each filter element 721 is one of filter types A, B, C, D, E, F, G, H, and I, with each respective filter-type characterized by a spectral pass-band different from the other filter-types.

An interface module selects one or more subsets of photo-sensor 711 outputs. Each subset of photo-sensor 711 outputs is associated with (receives light exclusively through) a single respective filter-type. For instance, in one such subset are the photo-sensors 711 that are associated with (receive light exclusively from) filter type A, another such subset are the photo-sensors 711 that are associated with filter type B and so forth. A control module is configured to generate a hyperspectral data cube 262 from the one or more sub-sets of photo-sensor outputs by generating a plurality of respective images 263. In some embodiments, each respective image 263 in the plurality of images is produced from a single respective sub-set of photo-sensor outputs 711 so that each respective image 263 in the plurality of images is associated with a particular filter-type. Thus, for example, referring to FIG. 7, all the photo-sensors 711 that receive filtered light from filter elements 721 of filter type A are used to form a first image 263-1, all the photo-sensors 711 that receive filtered light from filter elements 721 of filter type B are used to form a second image 263-2, all the photo-sensors 711 that receive filtered light from filter elements 721 of filter type C are used to form a third image 263-3, and so forth thereby creating a hyperspectral data cube 262 from the one or more sub-sets of photo-sensor outputs. The hyperspectral data cube 262 comprises the plurality of images, each image being of the same region of a subject but at a different wavelength or wavelength ranges.

The concept disclosed in FIG. 7 is highly advantageous because multiple light exposures do not need to be used to acquire all the images 263 needed to form the hyperspectral data cube 262. In some embodiments, a single light exposure is used to concurrently acquire each image 263. This is made possible because the spatial resolution of the sensor 112 exceeds the resolution necessary for an image 263. Thus, rather than using all the pixels in the sensor 112 to form each image 263, the pixels can be divided up in the manner illustrated in FIG. 7, for example, using filter plate 114 so that all the images are taken concurrently. In some implementations, the spectral pass-bands of the filter-elements used in a filter array 114 correspond to a predetermined set of spectral bands, e.g., used to identify a particular type of spectral signature in an object (e.g., in a tissue of a subject).

In one implementation, an imaging device comprises a filter array 114 containing a first set of filter elements sufficient to distinguish spectral signatures related to a first medical condition (e.g., a pressure ulcer) from healthy tissue (e.g., non-ulcerated tissue). In one implementation, the filter array 114 of the imaging device further contains a second set of filter elements sufficient to distinguish spectral signatures related to a second medical condition (e.g., a cancerous tissue) from healthy tissue (e.g., a non-cancerous tissue). In some implementations, the first set of filter elements and the second set of filter elements may overlap, such that a particular filter element is used for investigation of both types of medical conditions. Accordingly, in some implementations, the imaging device will have a plurality of imaging modalities, each individual imaging modality related to the investigation of a different medical condition.

Further implementations of the single-sensor imaging device are disclosed in International Publication No. WO 2014/063117, the content of which is expressly incorporated herein by reference, in its entirety, for all purposes.

In some implementations, a similar effect can be achieved by placing multiple imager chips in an array (e.g., a 2×2, 3×3, 4×4, or 5×5 array). To minimize off axis imaging errors, individual imager dies may be arranged in a tight, multi-chip module configuration.

In some implementations, the method is performed using an imaging device that concurrently captures multiple images, where each image represents a desired spectral band. Specifically, the imaging device uses multiple photo-sensors and beam splitting elements to capture a plurality of images concurrently. Thus, a user does not need to maintain perfect alignment between the imaging device and a subject while attempting to capture multiple discrete images, and can instead simply align the imaging device once and capture all of the required images in a single operation of the imaging device.

FIG. 8 is an exploded schematic view of an optical assembly of an exemplary concurrent capture imaging system, in accordance with some implementations, in which the optical paths formed by the optical path assembly are shown. In some implementations, the imager includes a single light source 120. In other implementations, as shown in FIG. 8, the imager contains two or more light sources 120, configured to emit light having different spectral bands (e.g., partially overlapping or non-overlapping). In some implementations, the light sources emit the same spectral bands, but are differentially filtered (e.g., by a filter placed in front of the light sources) such that the illuminating light from each light source has different spectral bands (e.g., partially overlapping or non-overlapping). The optical path assembly channels light received by the lens assembly 520 (e.g., illuminating light emitted from light source 120 and back-scattered from the region of interest on the patient) to the various photo-sensors 112 of the optical assembly.

Turning to FIG. 8, the optical assembly includes a first beam splitter 810-1, a second beam splitter 810-2, and a third beam splitter 810-3. Each beam splitter is configured to split the light received by the beam splitter into at least two optical paths. For example, beam splitters for use in the optical path assembly may split an incoming beam into one output beam that is collinear to the input beam, and another output beam that is perpendicular to the input beam.

Specifically, the first beam splitter 810-1 is in direct optical communication with the lens assembly 52, and splits the incoming light (represented by arrow 30) into a first optical path and a second optical path. The first optical path is substantially collinear with the light entering the first beam splitter 810-1, and passes to the second beam splitter 810-2. The second optical path is substantially perpendicular to the light entering the first beam splitter 810-1, and passes to the third beam splitter 810-3. In some implementations, the first beam splitter 810-1 is a 50:50 beam splitter. In other implementations, the first beam splitter 810-1 is a dichroic beam splitter.

The second beam splitter 810-2 is adjacent to the first beam splitter 810-1 (and is in direct optical communication with the first beam splitter 810-1), and splits the incoming light from the first beam splitter 810-1 into a third optical path and a fourth optical path. The third optical path is substantially collinear with the light entering the second beam splitter 810-2, and passes through to the first beam steering element 812-1. The fourth optical path is substantially perpendicular to the light entering the second beam splitter 810-2, and passes through to the second beam steering element 812-2. In some implementations, the second beam splitter 810-2 is a 50:50 beam splitter. In other implementations, the second beam splitter 810-2 is a dichroic beam splitter.

The beam steering elements 812 (e.g., 812-1 . . . 812-4) are configured to change the direction of the light that enters one face of the beam steering element. Beam steering elements 812 are any appropriate optical device that changes the direction of light. For example, in some implementations, the beam steering elements 812 are prisms (e.g., folding prisms or bending prisms). In some implementations, the beam steering elements 812 are mirrors. In some implementations, the beam steering elements 812 are other appropriate optical devices or combinations of devices.

Returning to FIG. 8, the first beam steering element 812-1 is adjacent to and in direct optical communication with the second beam splitter 810-2, and receives light from the third optical path (e.g., the output of the second beam splitter 810-2 that is collinear with the input to the second beam splitter 810-2). The first beam steering element 812-1 deflects the light in a direction that is substantially perpendicular to the fourth optical path (and, in some implementations, perpendicular to a plane defined by the optical paths of the beam splitters 212, e.g., the x-y plane) and onto the first photo-sensor 112-1. The output of the first beam steering element 214-1 is represented by arrow 31-1.

The second beam steering element 812-2 is adjacent to and in direct optical communication with the second beam splitter 810-2, and receives light from the fourth optical path (e.g., the perpendicular output of the second beam splitter 810-2). The second beam steering element 812-2 deflects the light in a direction that is substantially perpendicular to the third optical path (and, in some implementations, perpendicular to a plane defined by the optical paths of the beam splitters 810, e.g., the x-y plane) and onto the second photo-sensor 112-2. The output of the second beam steering element 812-2 is represented by arrow 31-2.

As noted above, the first beam splitter 810-1 passes light to the second beam splitter 810-2 along a first optical path (as discussed above), and to the third beam splitter 810-3 along a second optical path.

The third beam splitter 810-3 is adjacent to the first beam splitter 810-1 (and is in direct optical communication with the first beam splitter 810-1), and splits the incoming light from the first beam splitter 810-1 into a fifth optical path and a sixth optical path. The fifth optical path is substantially collinear with the light entering the third beam splitter 810-3, and passes through to the third beam steering element 812-3. The sixth optical path is substantially perpendicular to the light entering the third beam splitter 810-3, and passes through to the fourth beam steering element 812-4. In some implementations, the third beam splitter 810-3 is a 50:50 beam splitter. In other implementations, the third beam splitter 810-3 is a dichroic beam splitter.

The third beam steering element 812-3 is adjacent to and in direct optical communication with the third beam splitter 810-3, and receives light from the fifth optical path (e.g., the output of the third beam splitter 810-3 that is collinear with the input to the third beam splitter 810-3). The third beam steering element 812-3 deflects the light in a direction that is substantially perpendicular to the third optical path (and, in some implementations, perpendicular to a plane defined by the optical paths of the beam splitters 810, e.g., the x-y plane) and onto the third photo-sensor 112-3. The output of the third beam steering element 812-3 is represented by arrow 31-3.

The fourth beam steering element 812-4 is adjacent to and in direct optical communication with the third beam splitter 810-3, and receives light from the sixth optical path (e.g., the perpendicular output of the third beam splitter 810-3). The fourth beam steering element 812-4 deflects the light in a direction that is substantially perpendicular to the sixth optical path (and, in some implementations, perpendicular to a plane defined by the optical paths of the beam splitters 810, e.g., the x-y plane) and onto the fourth photo-sensor 112-4. The output of the fourth beam steering element 812-4 is represented by arrow 31-4.

As shown in FIG. 8, the output paths of the first and third beam steering elements 812-1, 812-3 are in opposite directions than the output paths of the second and fourth beam steering elements 812-2, 812-4. Thus, the image captured by the lens assembly 520 is projected onto the photo-sensors mounted on the opposite sides of the image assembly. However, the beam steering elements 812 need not face these particular directions. Rather, any of the beam steering elements 812 can be positioned to direct the output path of each beam steering element 812 in any appropriate direction. For example, in some implementations, all of the beam steering elements 812 direct light in the same direction. In such cases, all of the photo-sensors may be mounted on a single circuit board. Alternatively, in some implementations, one or more of the beam steering elements 812 directs light substantially perpendicular to the incoming light, but in substantially the same plane defined by the optical paths of the beam splitters 810 (e.g., within the x-y plane).

Further implementations of suitable devices and strategies for collection images in accordance with the current disclosure are disclosed in U.S. Non-Provisional application Ser. No. 14/664,754, filed on Mar. 20, 2015, the content of which is expressly incorporated herein by reference, in its entirety, for all purposes.

Hyperspectral Imaging

Hyperspectral and multispectral imaging are related techniques in larger class of spectroscopy commonly referred to as spectral imaging or spectral analysis. Typically, hyperspectral imaging relates to the acquisition of a plurality of images, each image representing a narrow spectral band captured over a continuous spectral range, for example, 5 or more (e.g., 5, 10, 15, 20, 25, 30, 40, 50, or more) spectral bands having a FWHM bandwidth of 1 nm or more each (e.g., 1 nm, 2 nm, 3 nm, 4 nm, 5 nm, 10 nm, 20 nm or more), covering a contiguous spectral range (e.g., from 400 nm to 800 nm). In contrast, multispectral imaging relates to the acquisition of a plurality of images, each image representing a narrow spectral band captured over a discontinuous spectral range.

For the purposes of the present disclosure, the terms "hyperspectral" and "multispectral" are used interchangeably and refer to a plurality of images, each image representing a narrow spectral band (having a FWHM bandwidth of between 10 nm and 30 nm, between 5 nm and 15 nm, between 5 nm and 50 nm, less than 100 nm, between 1 and 100 nm, etc.), whether captured over a continuous or discontinuous spectral range. For example, in some implementations, wavelengths 1-N of a hyperspectral data cube 1336-1 are contiguous wavelengths or spectral bands covering a contiguous spectral range (e.g., from 400 nm to 800 nm). In other implementations, wavelengths 1-N of a hyperspectral data cube 1336-1 are non-contiguous wavelengths or spectral bands covering a non-contiguous spectral ranges (e.g., from 400 nm to 440 nm, from 500 nm to 540 nm, from 600 nm to 680 nm, and from 900 to 950 nm).

As used herein, "narrow spectral range" refers to a continuous span of wavelengths, typically consisting of a FWHM spectral band of no more than about 100 nm. In certain embodiments, narrowband radiation consists of a FWHM spectral band of no more than about 75 nm, 50 nm, 40 nm, 30 nm, 25 nm, 20 nm, 15 nm, 10 nm, 5 nm, 4 nm, 3 nm, 2 nm, 1 nm, or less. In some implementations, wavelengths imaged by the methods and devices disclosed herein are selected from one or more of the visible, near-infrared, short-wavelength infrared, mid-wavelength infrared, long-wavelength infrared, and ultraviolet (UV) spectrums.

By "broadband" it is meant light that includes component wavelengths over a substantial portion of at least one band, e.g., over at least 20%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. In certain embodiments, broadband light includes component wavelengths across at least 100 nm of the electromagnetic spectrum. In other embodiments, broadband light includes component wavelengths across at least 150 nm, 200 nm, 250 nm, 300 nm, 400 nm, 500 nm, 600 nm, 700 nm, 800 nm, or more of the electromagnetic spectrum.

By "narrowband" it is meant light that includes components over only a narrow spectral region, e.g., less than 20%, or less than 15%, or less than 10%, or less than 5%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, e.g., may together constitute a broadband light source. In certain embodiments, broadband light includes component wavelengths across no more than 100 nm of the electromagnetic spectrum (e.g., has a spectral bandwidth of no more than 100 nm). In other embodiments, narrowband light has a spectral bandwidth of no more than 90 nm, 80 nm, 75 nm, 70 nm, 60 nm, 50 nm, 40 nm, 30 nm, 25 nm, 20 nm, 15 nm, 10 nm, 5 nm, or less of the electromagnetic spectrum.

As used herein, the "spectral bandwidth" of a light source refers to the span of component wavelengths having an intensity that is at least half of the maximum intensity, otherwise known as "full width at half maximum" (FWHM) spectral bandwidth. Many light emitting diodes (LEDs) emit radiation at more than a single discreet wavelength, and are thus narrowband emitters. Accordingly, a narrowband light source can be described as having a "characteristic wavelength" or "center wavelength," i.e., the wavelength emitted with the greatest intensity, as well as a characteristic spectral bandwidth, e.g., the span of wavelengths emitted with an intensity of at least half that of the characteristic wavelength.

By "coherent light source" it is meant a light source that emits electromagnetic radiation of a single wavelength in phase. Thus, a coherent light source is a type of narrowband light source with a spectral bandwidth of less than 1 nm. Non-limiting examples of coherent light sources include lasers and laser-type LEDs. Similarly, an incoherent light source emits electromagnetic radiation having a spectral bandwidth of more than 1 nm and/or is not in phase. In this regard, incoherent light can be either narrowband or broadband light, depending on the spectral bandwidth of the light.

Examples of suitable broadband light sources 104 include, without limitation, incandescent lights such as a halogen lamp, xenon lamp, a hydrargyrum medium-arc iodide lamp, and a broadband light emitting diode (LED). In some embodiments, a standard or custom filter is used to balance the light intensities at different wavelengths to raise the signal level of certain wavelength or to select for a narrowband of wavelengths. Broadband illumination of a subject is particularly useful when capturing a color image of the subject or when focusing the hyperspectral/multi spectral imaging system.

Examples of suitable narrowband, incoherent light sources 104 include, without limitation, a narrow band light emitting diode (LED), a superluminescent diode (SLD) (see, Redding B., arVix: 1110.6860 (2011), the content of which is hereby incorporated herein by reference in its entirety for all purposes), a random laser, and a broadband light source covered by a narrow band-pass filter. Examples of suitable narrowband, coherent light sources 104 include, without limitation, lasers and laser-type light emitting diodes. While both coherent and incoherent narrowband light sources 104 can be used in the imaging systems described herein, coherent illumination is less well suited for full-field imaging due to speckle artifacts that corrupt image formation (see, Oliver, B. M., *Proc IEEE* 51, 220-221 (1963)).

The conventional HSI system involves two scanning methods: spatial scanning and spectral scanning. Spatial scanning methods generate hyperspectral images by acquiring a complete spectrum for each pixel in the case of whiskbroom (point-scanning) instruments or line of pixels in pushbroom (line-scanning) instruments, and then spatially scanning through the scene. Spectral scanning methods, also called staring or area-scanning imaging, involves capturing the whole scene with 2-D detector arrays in a single exposure and then stepping through wavelengths to complete the data cube.

Hyperspectral Medical Imaging

The disclosure provides systems and methods useful for hyperspectral/multispectral medical imaging (HSMI). HSMI relies upon distinguishing the interactions that occur between light at different wavelengths and components of the human body, especially components located in or just under the skin. For example, it is well known that deoxyhemoglobin absorbs a greater amount of light at 700 nm than does water, while water absorbs a much greater amount of light at 1200 nm, as compared to deoxyhemoglobin. By measuring the absorbance of a two-component system consisting of deoxyhemoglobin and water at 700 nm and 1200 nm, the individual contribution of deoxyhemoglobin and water to the absorption of the system, and thus the concentrations of both components, can readily be determined. By extension, the individual components of more complex systems (e.g., human skin) can be determined by measuring the absorption of a plurality of wavelengths of light reflected or backscattered off of the system.

The particular interactions between the various wavelengths of light measured by hyperspectral/multispectral imaging and each individual component of the system (e.g., skin) produces hyperspectral/multispectral signature, when the data is constructed into a hyperspectral/multispectral data cube. Specifically, different regions (e.g., different ROI on a single subject or different ROI from different subjects) interact differently with light depending on the presence of, e.g., a medical condition in the region, the physiological structure of the region, and/or the presence of a chemical in the region. For example, fat, skin, blood, and flesh all interact with various wavelengths of light differently from one another. A given type of cancerous lesion interacts with various wavelengths of light differently from normal skin, from non-cancerous lesions, and from other types of cancerous lesions. Likewise, a given chemical that is present (e.g., in the blood, or on the skin) interacts with various wavelengths of light differently from other types of chemicals. Thus, the light obtained from each illuminated region of a subject has a spectral signature based on the characteristics of the region, which signature contains medical information about that region.

The structure of skin, while complex, can be approximated as two separate and structurally different layers, namely the epidermis and dermis. These two layers have very different scattering and absorption properties due to differences of composition. The epidermis is the outer layer of skin. It has specialized cells called melanocytes that produce melanin pigments. Light is primarily absorbed in the epidermis, while scattering in the epidermis is considered negligible. For further details, see G. H. Findlay, "Blue Skin," British Journal of Dermatology 83(1), 127-134 (1970), the content of which is incorporated herein by reference in its entirety for all purposes.

The dermis has a dense collection of collagen fibers and blood vessels, and its optical properties are very different from that of the epidermis. Absorption of light of a bloodless dermis is negligible. However, blood-born pigments like oxy- and deoxy-hemoglobin and water are major absorbers of light in the dermis. Scattering by the collagen fibers and absorption due to chromophores in the dermis determine the depth of penetration of light through skin.

Light used to illuminate the surface of a subject will penetrate into the skin. The extent to which the light penetrates will depend upon the wavelength of the particular radiation. For example, with respect to visible light, the longer the wavelength, the farther the light will penetrate into the skin. For example, only about 32% of 400 nm violet light penetrates into the dermis of human skin, while greater than 85% of 700 nm red light penetrates into the dermis or beyond (see, Capinera J. L., Encyclopedia of Entomology, 2nd Edition, Springer Science (2008) at page 2854, the content of which is hereby incorporated herein by reference in its entirety for all purposes). For purposes of the present disclosure, when referring to "illuminating a tissue," "reflecting light off of the surface," and the like, it is meant that radiation of a suitable wavelength for detection is backscattered from a tissue of a subject, regardless of the distance into the subject the light travels. For example, certain wavelengths of infra-red radiation penetrate below the surface of the skin, thus illuminating the tissue below the surface of the subject.

Briefly, light from the illuminator(s) on the systems described herein penetrates the subject's superficial tissue and photons scatter in the tissue, bouncing inside the tissue many times. Some photons are absorbed by oxygenated hemoglobin molecules at a known profile across the spectrum of light. Likewise for photons absorbed by de-oxygenated hemoglobin molecules. The images resolved by the optical detectors consist of the photons of light that scatter back through the skin to the lens subsystem. In this fashion, the images represent the light that is not absorbed by the various chromophores in the tissue or lost to scattering within the tissue. In some embodiments, light from the illuminators that does not penetrate the surface of the tissue is eliminated by use of polarizers. Likewise, some photons bounce off the surface of the skin into air, like sunlight reflecting off a lake.

Accordingly, different wavelengths of light may be used to examine different depths of a subject's skin tissue. Generally, high frequency, short-wavelength visible light is useful for investigating elements present in the epidermis, while lower frequency, long-wavelength visible light is useful for investigating both the epidermis and dermis. Furthermore, certain infra-red wavelengths are useful for investigating the epidermis, dermis, and subcutaneous tissues.

In the visible and near-infrared (VNIR) spectral range and at low intensity irradiance, and when thermal effects are negligible, major light-tissue interactions include reflection, refraction, scattering and absorption. For normal collimated incident radiation, the regular reflection of the skin at the air-tissue interface is typically only around 4%-7% in the 250-3000 nanometer (nm) wavelength range. For further details, see R. R. Anderson and J. A. Parrish, "The optics of human skin," Journal of Investigative Dermatology 77(1), 13-19 (1981), the content of which is hereby incorporated by reference in its entirety for all purposes. When neglecting the air-tissue interface reflection and assuming total diffusion of incident light after the stratum corneum layer, the steady state VNIR skin reflectance can be modeled as the light that first survives the absorption of the epidermis, then reflects back toward the epidermis layer due the isotropic scattering in the dermis layer, and then finally emerges out of the skin after going through the epidermis layer again.

Accordingly, the systems and methods described herein can be used to diagnose and characterize a wide variety of medical conditions. In one embodiment, the concentration of one or more skin or blood component is determined in order to evaluate a medical condition in a patient. Non-limiting examples of components useful for medical evaluation include: deoxyhemoglobin levels, oxyhemoglobin levels, total hemoglobin levels, oxygen saturation, oxygen perfusion, hydration levels, total hematocrit levels, melanin levels, collagen levels, and bilirubin levels. Likewise, the pattern, gradient, or change over time of a skin or blood component can be used to provide information on the medical condition of the patient.

Non-limiting examples of conditions that can be evaluated by hyperspectral/multispectral imaging include: tissue ischemia, ulcer formation, ulcer progression, pressure ulcer formation, pressure ulcer progression, diabetic foot ulcer formation, diabetic foot ulcer progression, venous stasis, venous ulcer disease, peripheral artery disease, atherosclerosis, infection, shock, cardiac decompensation, respiratory insufficiency, hypovolemia, the progression of diabetes, congestive heart failure, sepsis, dehydration, hemorrhage, hemorrhagic shock, hypertension, cancer (e.g., detection, diagnosis, or typing of tumors or skin lesions), retinal abnormalities (e.g., diabetic retinopathy, macular degeneration, or corneal dystrophy), skin wounds, burn wounds, exposure to a chemical or biological agent, and an inflammatory response.

In one embodiment, the systems and methods described herein are used to evaluate tissue oximetery and correspondingly, medical conditions relating to patient health derived from oxygen measurements in the superficial vasculature. In certain embodiments, the systems and methods described herein allow for the measurement of oxygenated hemoglobin, deoxygenated hemoglobin, oxygen saturation, and oxygen perfusion. Processing of these data provide information to assist a physician with, for example, diagnosis, prognosis, assignment of treatment, assignment of surgery, and the execution of surgery for conditions such as critical limb ischemia, diabetic foot ulcers, pressure ulcers, peripheral vascular disease, surgical tissue health, etc.

In one embodiment, the systems and methods described herein are used to evaluate diabetic and pressure ulcers. Development of a diabetic foot ulcer is commonly a result of a break in the barrier between the dermis of the skin and the subcutaneous fat that cushions the foot during ambulation. This rupture can lead to increased pressure on the dermis, resulting in tissue ischemia and eventual death, and ultimately manifesting in the form of an ulcer (Frykberg R. G. et al., Diabetes Care 1998; 21(10):1714-9). Measurement of oxyhemoglobin, deoxyhemoglobin, and/or oxygen saturation levels by hyperspectral/multispectral imaging can provide medical information regarding, for example: a likelihood of ulcer formation at an ROI, diagnosis of an ulcer, identification of boundaries for an ulcer, progression or regression of ulcer formation, a prognosis for healing of an ulcer, the likelihood of amputation resulting from an ulcer. Further information on hyperspectral/multispectral methods for the detection and characterization of ulcers, e.g., diabetic foot ulcers, are found in U.S. Patent Application Publication No. 2007/0038042, and Nouvong A. et al., Diabetes Care. 2009 Nov. 32(11): 2056-61, the contents of which are hereby incorporated herein by reference in their entireties for all purposes.

Other examples of medical conditions include, but are not limited to: tissue viability (e.g., whether tissue is dead or living, and/or whether it is predicted to remain living); tissue ischemia; malignant cells or tissues (e.g., delineating malignant from benign tumors, dysplasias, precancerous tissue, metastasis); tissue infection and/or inflammation; and/or the presence of pathogens (e.g., bacterial or viral counts). Some embodiments include differentiating different types of tissue from each other, for example, differentiating bone from flesh, skin, and/or vasculature. Some embodiments exclude the characterization of vasculature.

In yet other embodiments, the systems and methods provided herein can be used during surgery, for example to determine surgical margins, evaluate the appropriateness of surgical margins before or after a resection, evaluate or monitor tissue viability in near-real time or real-time, or to assist in image-guided surgery. For more information on the use of hyperspectral/multispectral imaging during surgery, see, Holzer M. S. et al., J Urol. 2011 August; 186(2): 400-4; Gibbs-Strauss S. L. et al., Mol Imaging. 2011 April; 10(2): 91-101; and Panasyuk S. V. et al., Cancer Biol Ther. 2007 March; 6(3): 439-46, the contents of which are hereby incorporated herein by reference in their entirety for all purposes.

For more information on the use of hyperspectral/multispectral imaging in medical assessments, see, for example: Chin J. A. et al., J Vasc Surg. 2011 December; 54(6): 1679-88; Khaodhiar L. et al., Diabetes Care 2007; 30:903-910; Zuzak K. J. et al., Anal Chem. 2002 May 1; 74(9): 2021-8; Uhr J. W. et al., Transl Res. 2012 May; 159(5): 366-75; Chin M. S. et al., J Biomed Opt. 2012 February; 17(2): 026010; Liu Z. et al., Sensors (Basel). 2012; 12(1): 162-74; Zuzak K. J. et al., Anal Chem. 2011 Oct. 1; 83(19): 7424-30; Palmer G. M. et al., J Biomed Opt. 2010 November-December; 15(6): 066021; Jafari-Saraf and Gordon, Ann Vasc Surg. 2010 August; 24(6): 741-6; Akbari H. et al., IEEE Trans Biomed Eng. 2010 August; 57(8): 2011-7; Akbari H. et al., Conf Proc IEEE Eng Med Biol Soc. 2009: 1461-4; Akbari H. et al., Conf Proc IEEE Eng Med Biol Soc. 2008: 1238-41; Chang S. K. et al., Clin Cancer Res. 2008 Jul. 1; 14(13): 4146-53; Siddiqi A. M. et al., Cancer. 2008 Feb. 25; 114(1): 13-21; Liu Z. et al., Appl Opt. 2007 Dec. 1; 46(34): 8328-34; Zhi L. et al., Comput Med Imaging Graph. 2007 December; 31(8): 672-8; Khaodhiar L. et al., Diabetes Care. 2007 April; 30(4): 903-10; Ferris D. G. et al., J Low Genit Tract Dis. 2001 April; 5(2): 65-72; Greenman R. L. et al., Lancet. 2005 Nov. 12; 366(9498): 1711-7; Sorg B. S. et al., J Biomed Opt. 2005 July-August; 10(4): 44004; Gillies R. et al., and Diabetes Technol Ther. 2003; 5(5): 847-55, the contents of which are hereby incorporated herein by reference in their entirety for all purposes.

In yet other embodiments, the systems and methods provided herein can be used during surgery, for example to determine surgical margins, evaluate the appropriateness of surgical margins before or after a resection, evaluate or monitor tissue viability in near-real time or real-time, or to assist in image-guided surgery. For more information on the use of hyperspectral/multispectral imaging during surgery, see, Holzer M. S. et al., J Urol. 2011 August; 186(2): 400-4; Gibbs-Strauss S. L. et al., Mol Imaging. 2011 April; 10(2): 91-101; and Panasyuk S. V. et al., Cancer Biol Ther. 2007 March; 6(3): 439-46, the contents of which are hereby incorporated herein by reference in their entirety for all purposes.

EXAMPLES

Example 1—Selection of Wavelengths for Tissue Oxygenation Measurements by Sensitivity Maximization An initial attempt was made to select a minimal set of eight wavelengths that allow accurate determination of tissue oxygenation in human tissue, by selecting wavelengths that optimized sensitivity to oxyhemoglobin and deoxyhemoglobin (e.g., the chromophores of interest), while minimizing sensitivity to melanin (e.g., the major background chromophore in surface tissues). Numerical optimization is used to select a set of wavelengths, defined as that ideally maximizes the ratio:

$$L = \frac{\frac{dOXY}{dc_{oxy}} \cdot \frac{dDEOXY}{dc_{deoxy}}}{\frac{dOXY}{dc_{deoxy}} \cdot \frac{dDEOXY}{dc_{oxy}} \cdot \frac{dOXY}{dc_{melanin}} \cdot \frac{dDEOXY}{dc_{melanin}}} \quad \text{Equation 1}$$

where dOXY is change in measured oxyhemoglobin concentration, dDEOXY is change in measured deoxyhemoglobin concentration, $dc_{oxy}$ is change in oxyhemoglobin concentration, $dc_{deoxy}$ is change in deoxyhemoglobin concentration, and $dc_{melanin}$ is change in melanin concentration. The proper set of wavelengths $\vec{\lambda}$ will increase the sensitivity of the measured OXY/DEOXY to the true concentration of oxyhemoglobin $c_{oxy}/c_{deoxy}$, and minimize the cross-sensitivity between OXY and DEOXY and their sensitivity to the melanin concentration $c_{melanin}$. Potential members of $\vec{\lambda}$ were restricted to be between 500 and 640 nm and to be multiples of 5 nm. However, in practice, the expression could be evaluated over any range of wavelengths and relative wavelength steps.

To evaluate L for a given candidate set of wavelengths $\vec{\lambda}$, the tissue reflectance for wavelength set $\vec{\lambda}$ was simulated using a range of randomized concentrations $c_{oxy}$, $c_{deoxy}$, and $c_{melanin}$. The hyperspectral algorithm for oxyhemoglobin and deoxyhemoglobin determination provided in U.S. Pat. No. 8,644,911 was then applied to the simulated tissue reflectances to estimate OXY and DEOXY. The derivatives in Equation 1 were approximated by perturbing $c_{oxy}$, $c_{deoxy}$, and $c_{melanin}$ by a small change in concentration (~$10^{-6}$) and estimating the perturbed OXY and DEOXY from the simulated tissue reflectance of the perturbed concentrations.

For perturbed concentrations of oxyhemoglobin, deoxyhemoglobin, and melanin ($c_{oxy,p}$, $c_{deoxy,p}$, and $c_{melanin,p}$), and perturbed OXY and DEOXY estimates ($OXY_p$ and $DEOXY_p$), the sensitivity of OXY/DEOXY is approximated by:

$$\frac{dOXY}{dc_{oxy}} = \frac{OXY - OXY_p}{c_{oxy} - x_{oxy,p}} \quad \text{Equation 2}$$

$$\frac{dDEOXY}{dc_{deoxy}} = \frac{DEOXY - DEOXY_p}{c_{deoxy} - c_{deoxy,p}} \quad \text{Equation 3}$$

the cross-sensitivity between OXY and DEOXY is approximated by:

$$\frac{dOXY}{dc_{deoxy}} = \frac{OXY - OXY_p}{c_{deoxy} - c_{deoxy,p}} \quad \text{Equation 4}$$

$$\frac{dDEOXY}{dc_{oxy}} = \frac{DEOXY - DEOXY_p}{c_{oxy} - c_{oxy,p}} \quad \text{Equation 5}$$

and the sensitivity to melanin is approximated by:

$$\frac{dOXY}{dc_{melanin}} = \frac{OXY - OXY_p}{c_{melanin} - c_{melanin,p}} \quad \text{Equation 6}$$

$$\frac{dDEOXY}{dc_{melanin}} = \frac{DEOXY - DEOXY_p}{c_{melanin} - c_{melanin,p}} \quad \text{Equation 7}$$

L was found by evaluating Equation 2 to Equation 7 and substituting the solutions into Equation 1. In each case, $c_{x,p} = c_x + 10^{-6}$. The median value of $\vec{\lambda}$ was found over randomized sets of $c_{oxy}$, $c_{deoxy}$, and $c_{melanin}$ at a fixed $\vec{\lambda}$. The process was repeated using different $\vec{\lambda}$ chosen by a guided exhaustive search (e.g., using a genetic algorithm) until a $\vec{\lambda}$ was found that maximized L. The final set of selected wavelengths from the analysis was 500 nm, 530 nm, 545 nm, 570 nm, 585 nm, 600 nm, 615 nm, and 640 nm.

Example 2—Selection of Wavelengths for Tissue Oxygenation Measurements by Exhaustive Search Over Clinical Data The objective of the search was to find sets of eight wavelengths that perform about as well in determining tissue oxygenation as the set of fifteen wavelengths described in U.S. Pat. No. 8,644,911 (500 nm, 510 nm, 520 nm, 530 nm, 540 nm, 550 nm, 560 nm, 570 nm, 580 nm, 590 nm, 600 nm, 610 nm, 620 nm, 640 nm, and 660 nm), the disclosure of which is hereby expressly incorporated by reference in its entirety for all purposes.

A reference dataset containing 169 hypercubes (i.e., image sets captured at each of the fifteen wavelengths disclosed above) from approximately 50 health patients was used for this analysis. Briefly, each hypercube was processed according to the hyperspectral algorithm disclosed in U.S. Pat. No. 8,644,911, at all fifteen wavelengths, to determine baseline oxyhemoglobin and deoxyhemoglobin values for each pixel. The algorithm was then applied to the same hypercube, at a unique subset of eight wavelengths. The resulting OXY and DEOXY maps for each subset of eight wavelengths was then compared to the baseline oxyhemoglobin and deoxyhemoglobin values determined using all fifteen wavelengths. The fifteen and eight wavelength processed maps were split into averaged segments, compared, and their correlation evaluated. The process was performed for all 6435 combinations of eight wavelengths from the original set of fifteen wavelengths.

OXY and DEOXY maps were produced from a set of measured reflectance maps, $R_{measured}(\lambda)$, at multiple wavelengths by converting tissue reflectance into apparent absorption and estimating the relative oxyhemoglobin and deoxyhemoglobin concentrations. The relationship between measured reflectance and OXY and DEOXY is described by:

$$R^{-1}(A(\lambda)) \rightarrow (\text{OXY}, \text{DEOXY}) \qquad \text{Equation 8}$$

where $A(\lambda)$ is the apparent absorption defined as:

$$A(\lambda) = -\log_{10}(R_{measured}(\lambda)) \qquad \text{Equation 9}$$

where $R_{measured}(\lambda)$ is the wavelength dependent reflectance image of tissue captured by the hyperspectral imaging device.

The transformation from reflectance to apparent absorption and to relative concentration arises from the Beer-Lambert law which posits that the intensity of light traveling through an absorbing but non-scattering medium decays exponentially with the product of the distance traveled and absorption coefficient of the medium.

In the simple case of light travelling through a non-scattering media in a cuvette, light with initial intensity $I_0$ and output intensity $I_1$, incident to a cuvette of length L filled with a mixture of substances, results in a total absorption coefficient of $\mu_a = \Sigma c_i \epsilon_i$. Absorption $A(\lambda)$ is logarithmically related to the ratio of the intensity $I_0$ and output intensity $I_1$, also called transmittance $$T = \frac{I_1}{I_0},$$

and is linearly related to the absorption spectra $\epsilon_i(\lambda)$ of the individual chromophores in the cuvette via their molar concentrations $C_i$, defined as:

$$A(\lambda) = -\log_{10}\left(\frac{I_1(\lambda)}{I_0(\lambda)}\right) = L\sum C_i \epsilon_i(\lambda) \qquad \text{Equation 10}$$

Since the cuvette side-length L and the molar absorption spectra $\epsilon_i(\lambda)$ are known, the concentrations $C_i$ can be found by linearly least squares fitting.

However, light traversing tissue encounters multiple absorption and scattering events before exiting the tissue, and thus requires the use of a modified Beer-Lambert law described as:

$$A(\lambda) = -\log_{10}(R_{measured}(\lambda)) = L(\mu'_s(\lambda))\Sigma C_i \epsilon_i(\lambda) \qquad \text{Equation 11}$$

where the function $L(\mu'_s(\lambda))$ is the effective average pathlength of light through tissue before remittance and is a function of the scattering properties of the tissue and the wavelength of light. $L(\mu'_s(\lambda))$ can be simplified into a constant by averaging over the wavelengths of interest defined by:

$$\tilde{L} = \frac{1}{\lambda_{max} - \lambda_{min}} \int_{\lambda_{min}}^{\lambda_{max}} L(\mu'_s(\lambda)) d\lambda \qquad \text{Equation 12}$$

Then the modified Beer-Lambert law simplifies into an equation defining the relationship between apparent absorption and relative concentration $$A(\lambda) \approx \tilde{L}\Sigma C_i \epsilon_i(\lambda) = \Sigma k_i \epsilon_i(\lambda) \qquad \text{Equation 13}$$

The simplified and modified Beer-Lambert law is similar to Equation 10 in that $C_i$ and $k_i$ are solvable through linear least square fit. Importantly, the concentration of a chromophore $C_i$ is proportional to relative concentrations $k_i$ and that exact knowledge of $L(\mu'_s(\lambda))$ and $\tilde{L}$ is not required if only relative concentrations are of interest.

Applying the measured reflectance from each candidate subset of eight wavelengths to Equation 13, the apparent absorption was modeled as a linear combination of:

$$A(\lambda) = k_1 + k_2\lambda + k_3\lambda^2 + k_4\epsilon_{oxy}(\lambda) + k_5\epsilon_{deoxy} \qquad 14$$

where $\epsilon_{oxy}(\lambda)$ and $\epsilon_{deoxy}(\lambda)$ are the molar absorption coefficients of oxyhemoglobin and deoxyhemoglobin, $k_4$ and $k_5$ are the relative concentrations of oxyhemoglobin and deoxyhemoglobin, and $\lambda$ is the wavelength of light interrogating the tissue. The constant $k_1$, linear $k_2$, and quadratic $k_3$ are present in the linear combination to account for absorption contribution by melanin. Each $k_i$ was solved by linear least square fit.

Finally, relative concentrations of oxyhemoglobin and deoxyhemoglobin were converted to OXY and DEOXY by:

$$\text{OXY} = c_{oxy} c_{scale} k_4 \qquad \text{Equation 15}$$

$$\text{DEOXY} = c_{deoxy} c_{scale} k_5 \qquad \text{Equation 16}$$

where $c_{oxy}$ and $c_{deoxy}$ are scaling factors determined empirically from correlation experiments and $c_{scale}$ is an arbitrary scale constant chosen for esthetic purposes.

Conventionally, oxyhemoglobin and deoxyhemoglobin values determined by medical hyperspectral imaging are presented to the physician as averages over a subset of the pixels in an image. Thus, to assess the accuracy of the candidate subsets of eight wavelengths, as compared to the fifteen wavelength standard, average OXY and DEOXY values were averaged over contiguous squares of approximately forty by forty pixels. The resulting averages of OXY and DEOXY determined using sets of eight and fifteen wavelengths were compared for each hypercube. An example of the square segmentation for an OXY map is shown in FIG. 9.

To improve the accuracy of oxyhemoglobin and deoxyhemoglobin measurement using eight wavelengths, a linear correction was applied to correlate the results with those achieved using fifteen wavelengths. The linear correction for OXY and DEOXY were solved by fitting observations of OXY and DEOXY into the linear models:

$$\begin{bmatrix} OXY_{15,1} \\ OXY_{15,2} \\ OXY_{15,3} \\ \vdots \\ OXY_{15,n} \end{bmatrix} = \begin{bmatrix} 1 & OXY_{8,1} & DEOXY_{8,1} \\ 1 & OXY_{8,2} & DEOXY_{8,2} \\ 1 & OXY_{8,3} & DEOXY_{8,3} \\ \vdots & \vdots & \vdots \\ 1 & OXY_{8,n} & DEOXY_{8,n} \end{bmatrix} \begin{bmatrix} OC_1 \\ OC_2 \\ OC_3 \end{bmatrix} \quad \text{Equation 17}$$

$$\begin{bmatrix} DEOXY_{15,1} \\ DEOXY_{15,2} \\ DEOXY_{15,3} \\ \vdots \\ DEOXY_{15,n} \end{bmatrix} = \begin{bmatrix} 1 & OXY_{8,1} & DEOXY_{8,1} \\ 1 & OXY_{8,2} & DEOXY_{8,2} \\ 1 & OXY_{8,3} & DEOXY_{8,3} \\ \vdots & \vdots & \vdots \\ 1 & OXY_{8,n} & DEOXY_{8,n} \end{bmatrix} \begin{bmatrix} dc_1 \\ dc_2 \\ dc_3 \end{bmatrix} \quad \text{Equation 18}$$

where $OXY_{15,n}$ and $DEOXY_{15,n}$ are the averaged values of 15 wavelength results, $OXY_{8,1}$ and $DEOXY_{8,1}$ are the averaged values of 8 wavelength results. The value of n was n=9×9×169=13,689 and corresponded to the total number of averaging squares over 169 images taken from the normal population. The values $oc_1$, $oc_2$, and $oc_3$ are linear correction coefficients for OXY, and $dc_1$, $dc_2$, and $dc_3$ are linear correction coefficients for DEOXY. The coefficients oc and dc can be solved using linear least square fit. Substituting the coefficients into Equation 19 and Equation 20 enables evaluating corrected OXY and DEOXY values $$OXY_{corrected} = oc_1 + oc_2 OXY_8 oc_3 DEOXY_8 \quad \text{Equation 19}$$

$$DEOXY_{corrected} = dc_1 + dc_2 OXY_8 dc_3 DEOXY_8 \quad \text{Equation 20}$$

Figures 10A, 10B:
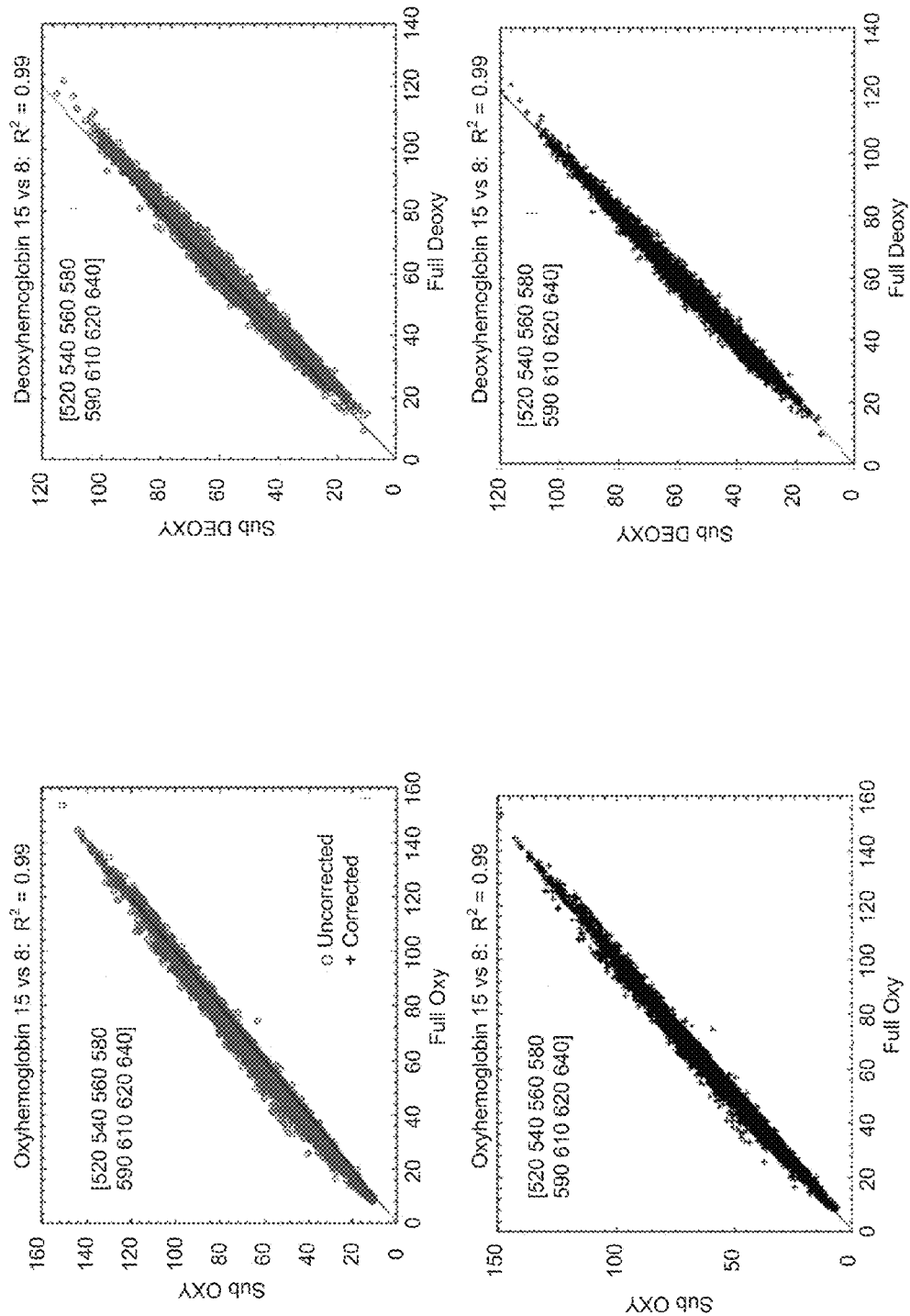
FIGS. 10A and 10B illustrate OXY or DEOXY scatter plots for exemplary subset 5778 of eight wavelenghs, generated according to some implementations.

The corrected OXY and DEOXY values generated from candidate subsets of eight wavelengths were then evaluated against the OXY and DEOXY values generated using all fifteen wavelengths by fitting a scatter plot to a statistical model and computing the coefficient of determination ($R^2$) for all subsets of eight wavelengths. $R^2$ values close to 1 are desired and indicate a good fit. $R^2$ can be evaluated by:

$$R^2 = \frac{\sum_i^l (y_i - f_i)^2}{\sum_i^l (y_i - \bar{y})^2} \quad \text{Equation 21}$$

where $\bar{y}$ is the average 8 wavelengths OXY or DEOXY value, $y_i$ is an element of the 8 wavelengths result, and $f_i$ is the corresponding element of the statistical model and subsequently the corresponding 15 wavelengths OXY or DEOXY value (namely, the 45 degree line). FIG. 10A-10B illustrate OXY or DEOXY scatter plots for an exemplary subset of eight wavelenghs, respectively.

Evaluation of the scatter plot comparisons revealed two eight-wavelength subsets that provided measurements correlating to both the OXY or DEOXY measurements obtained using all fifteen wavelengths with an $R^2$ value of at least 0.99. Advantageously, replacement of the 640 nm wavelength in subset 2 (ID 5778) with a wavelength at 660 nm also gives an eight-wavelength subset that provides OXY and DEOXY measurements correlating to those obtained using all fifteen wavelengths with an $R^2$ value of at least 0.99. These subsets are given in Table 1.

TABLE 1

Optimal sets of eight wavelengths.

| Subset | ID | W1 | W2 | W3 | W4 | W5 | W6 | W7 | W8 | OXY $R^2$ | DEOXY $R^2$ |
|---|---|---|---|---|---|---|---|---|---|---|---|
| 1 | 4526 | 510 | 530 | 540 | 560 | 580 | 590 | 620 | 660 | 0.998 | 0.996 |
| 2 | 5778 | 520 | 540 | 560 | 580 | 590 | 610 | 620 | 640 | 0.994 | 0.990 |
| 3 |  | 520 | 540 | 560 | 580 | 590 | 610 | 620 | 660 | 0.994 | 0.995 |

The identified wavelengths have near perfect correlation between eight wavelengths and fifteen wavelengths. Notably, the first subset includes wavelengths between 510 nm and 660 nm, while the second subset includes wavelengths between 520 nm and 640 nm. The 30 nm difference between the span of the first subset and the span of the second subset allow for some flexibility in the design of a suitable hyperspectral camera.

Example 3—Evaluation of Optimal Subset #2

Figure 11A:
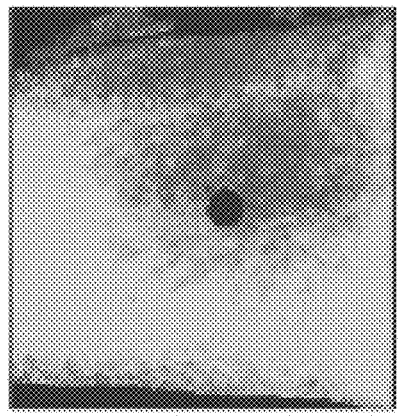
FIGS. 11A, 11B, 11C, 11D, and 11E show OXY and DEOXY maps, generated from a first hyperspectral data set, using all fifteen wavelengths (FIG. 11A—OXY.
Figure 11B:
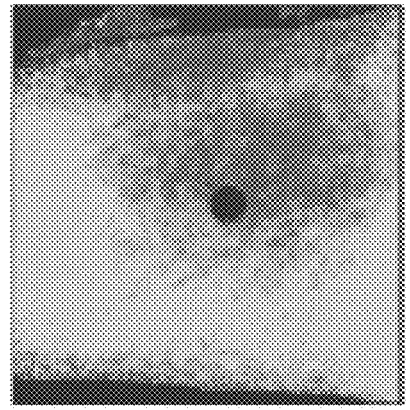
Figure 11C:
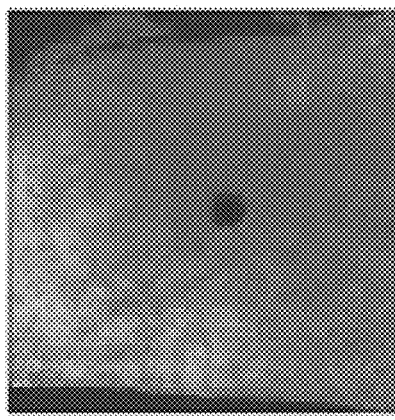
Figure 11D:
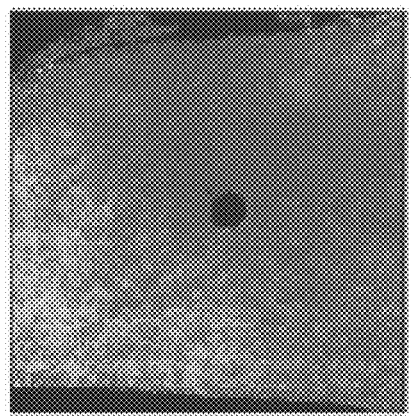
Figure 11E:
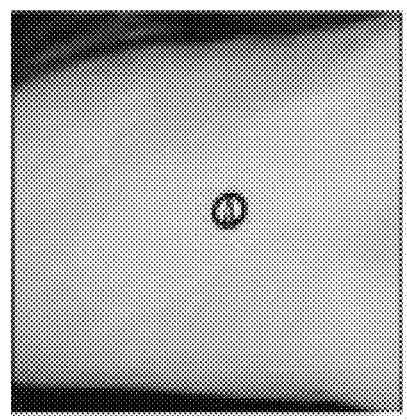

An individual data set, containing images of the bottom of a foot from a healthy individual at all fifteen wavelengths, was processed using either the full fifteen wavelengths or the eight wavelengths in subset 5778 (optimal subset number 2). As shown in FIGS. 11A-11E, there were minimal visual differences between the processed OXY and DEOXY maps generated using all fifteen wavelengths (FIG. 11A—OXY; FIG. 11C—DEOXY) and those generated using only eight wavelengths (FIG. 11B—OXY; FIG. 11D—DEOXY). The OXY and DEOXY maps generated using only eight wavelengths were corrected using the linear correction factors for subset number 2. FIG. 11E shows a native image of the tissue.

Statistics for the corrected and uncorrected OXY and DEOXY pixel values determined using eight wavelengths were then plotted against those determined using all fifteen wavelengths. FIGS. 12A and 12C are histograms showing the pixel value distribution of the three OXY and DEOXY maps, respectively. As shown, the shapes of the histograms generated using pixel data from the eight-wavelength and fifteen-wavelength analysis are similar. FIGS. 12B and 12D are scatter plots of the uncorrected and corrected pixel values determined using eight wavelengths plotted against pixel values determined using all fifteen wavelengths. As shown, there is minimal difference between the corrected and uncorrected data generated using eight wavelengths and the mean of the data generated with fifteen wavelengths or eight wavelengths (corrected or uncorrected).

Qualitative analysis of the OXY and DEOXY maps generated with fifteen and eight wavelengths was then performed by averaging square segments of the maps. FIGS. 13A and 13C show mean pixel values for approximately 40-pixel squares overlaid on the OXY and DEOXY maps generated using all fifteen wavelengths. The cross indicates the bottom right of each square. The difference between the averaged values in the maps generated using fifteen wavelengths and the corrected maps generated using eight wavelengths was then determined. FIGS. 13B and 13D show the difference between the averaged values overlaid on the OXY and DEOXY maps generated using the corrected eight wavelengths. Positive difference values indicate over-prediction, while negative values indicate under-prediction. As shown, the error introduced by the use of only eight wavelengths is minimal, and is only noticeable along the edges of the limb.

Example 4—Further Evaluation of Optimal Subset #2

Figure 14A:
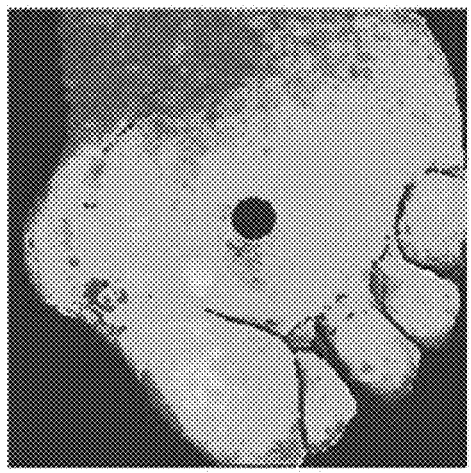
FIGS. 14A, 14B, 14C, 14D, and 14E show OXY and DEOXY maps, generated from a second hyperspectral data set, using all fifteen wavelengths (FIG. 14A—OXY.
Figure 14B:
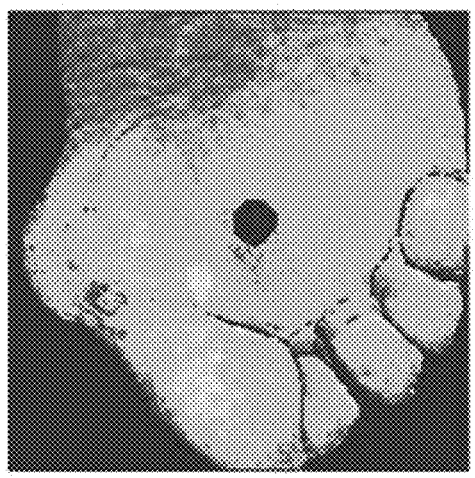
Figure 14C:
Figure 14D:
Figure 14E:
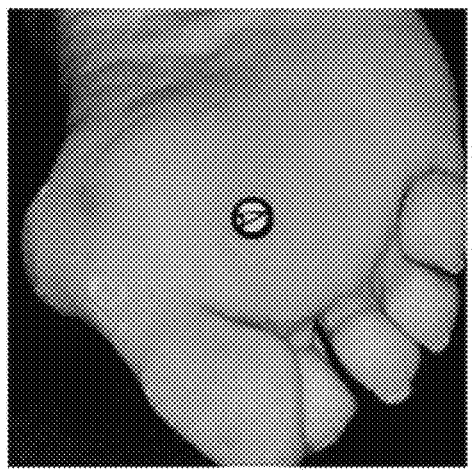

Two more data sets, containing images of the bottom of healthy individuals' feet at all fifteen wavelengths, were further was processed using either the full fifteen wavelengths or the eight wavelengths in subset 5778 (optimal subset number 2). As shown in FIGS. 14A-14E, there were minimal visual differences between the processed OXY and DEOXY maps generated using all fifteen wavelengths (FIG. 14A—OXY; FIG. 14C—DEOXY) and those generated using only eight wavelengths (FIG. 14B—OXY; FIG. 14D—DEOXY) for the first data set. The OXY and DEOXY maps generated using only eight wavelengths were corrected using the linear correction factors for subset number 2. FIG. 14E shows a native image of the tissue.

Figures 15A, 15B, 15C, 15D:
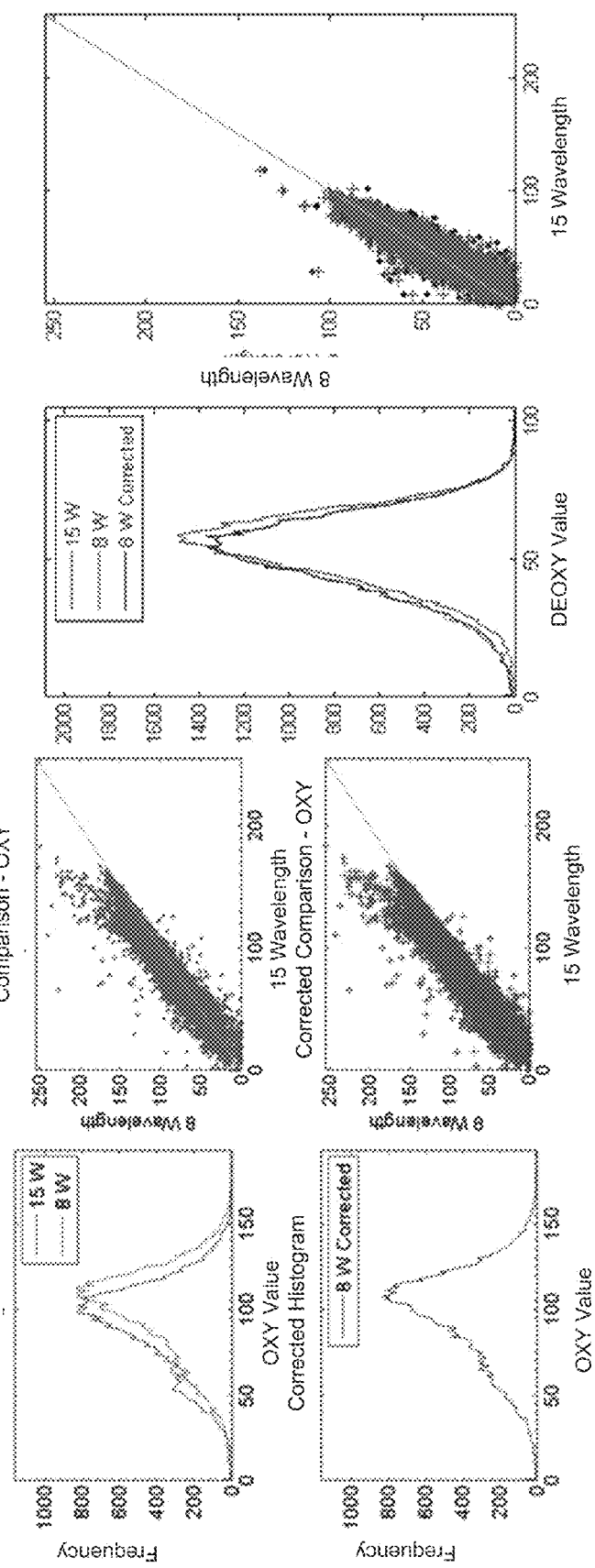
FIGS. 15A, 15B, 15C, and 15D illustrate statistics generated from the three OXY and DEOXY maps generated using all fifteen wavelengths or only the eight wavelengths of exemplary subset 5778, from the second hyperspectral data set, according to some implementations.

Statistics for the corrected and uncorrected OXY and DEOXY pixel values determined using eight wavelengths were then plotted against those determined using all fifteen wavelengths. FIGS. 15A and 15C are histograms showing the pixel value distribution of the three OXY and DEOXY maps, respectively. FIGS. 15B and 15D are scatter plots of the uncorrected and corrected pixel values determined using eight wavelengths plotted against pixel values determined using all fifteen wavelengths. As shown in the histograms, the uncorrected and corrected maps generated using eight wavelengths have higher OXY values and lower DEOXY values than the wavelength maps generated using all fifteen wavelengths. The scatter plots and mean statistics indicate that the maps generated using eight wavelengths over-predict OXY and slightly under-predict DEOXY values, as compared to maps generated using all fifteen wavelengths.

Figure 16A:
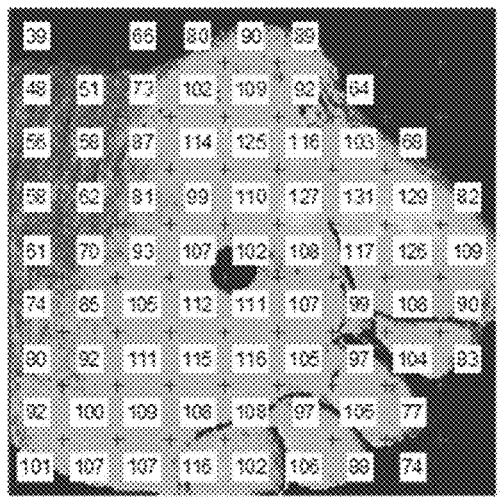
FIGS. 16A, 16B, 16C and 16D illustrate qualitative analysis of the OXY and DEOXY maps generated from the second hyperspectral data set, using fifteen and eight wavelengths, according to some implementations.
Figure 16B:
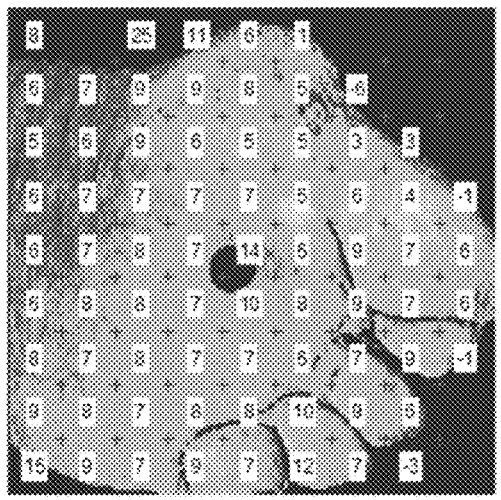
Figure 16C:
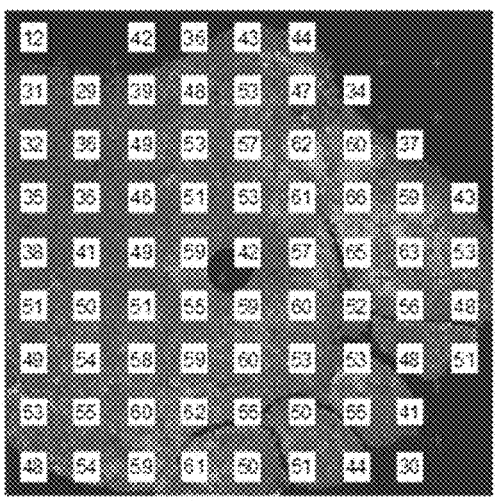
Figure 16D:
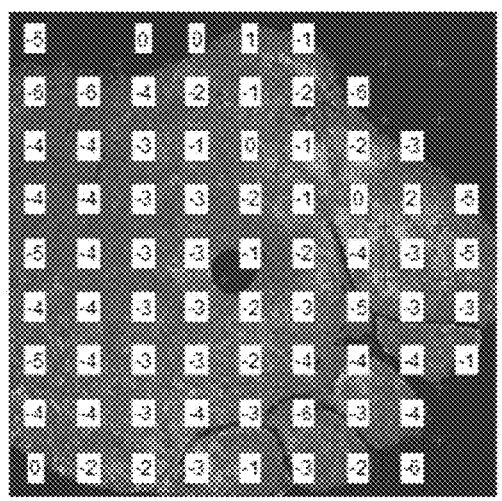

Qualitative analysis of the OXY and DEOXY maps generated with fifteen and eight wavelengths was then performed by averaging square segments of the maps. FIGS. 16A and 16C show mean pixel values for approximately 40-pixel squares overlaid on the OXY and DEOXY maps generated using all fifteen wavelengths. The cross indicates the bottom right of each square. The difference between the averaged values in the maps generated using fifteen wavelengths and the corrected maps generated using eight wavelengths was then determined. FIGS. 16B and 16D show the difference between the averaged values overlaid on the OXY and DEOXY maps generated using the corrected eight wavelengths. The number of positive errors in the OXY error map indicates over-prediction of OXY values. The net number of negative errors in the DEOXY error map indicates under-prediction of DEOXY values.

Figure 17A:
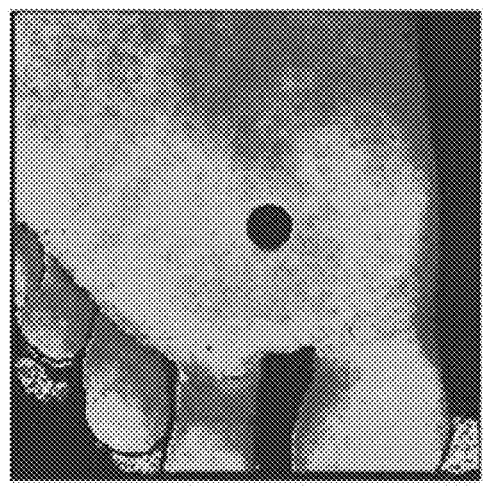
FIGS. 17A, 17B, 17C, 17D, and 17E show OXY and DEOXY maps, generated from a third hyperspectral data set, using all fifteen wavelengths (FIG. 17A—OXY.
Figure 17B:
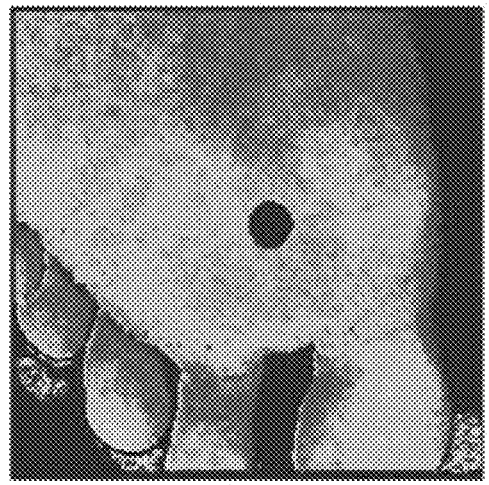
Figure 17C:
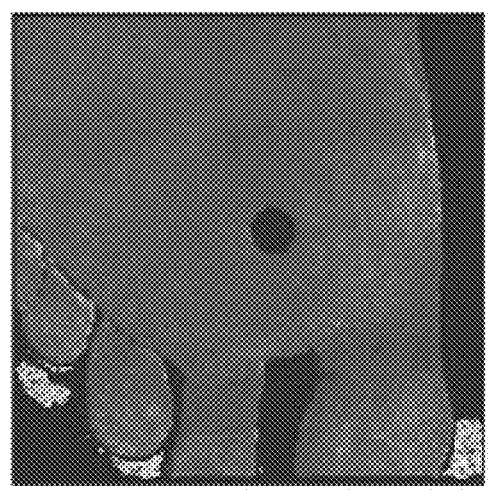
Figure 17D:
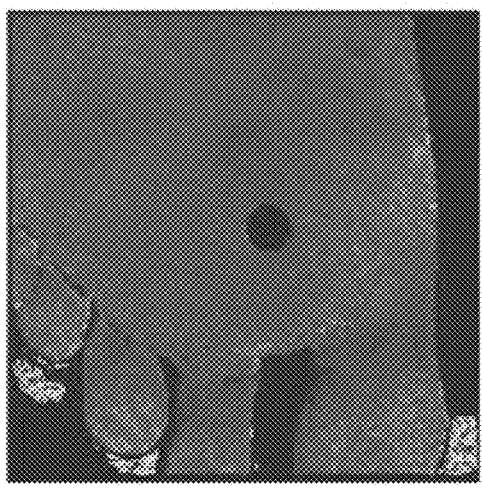
Figure 17E:
Figures 18A, 18B, 18C, 18D:
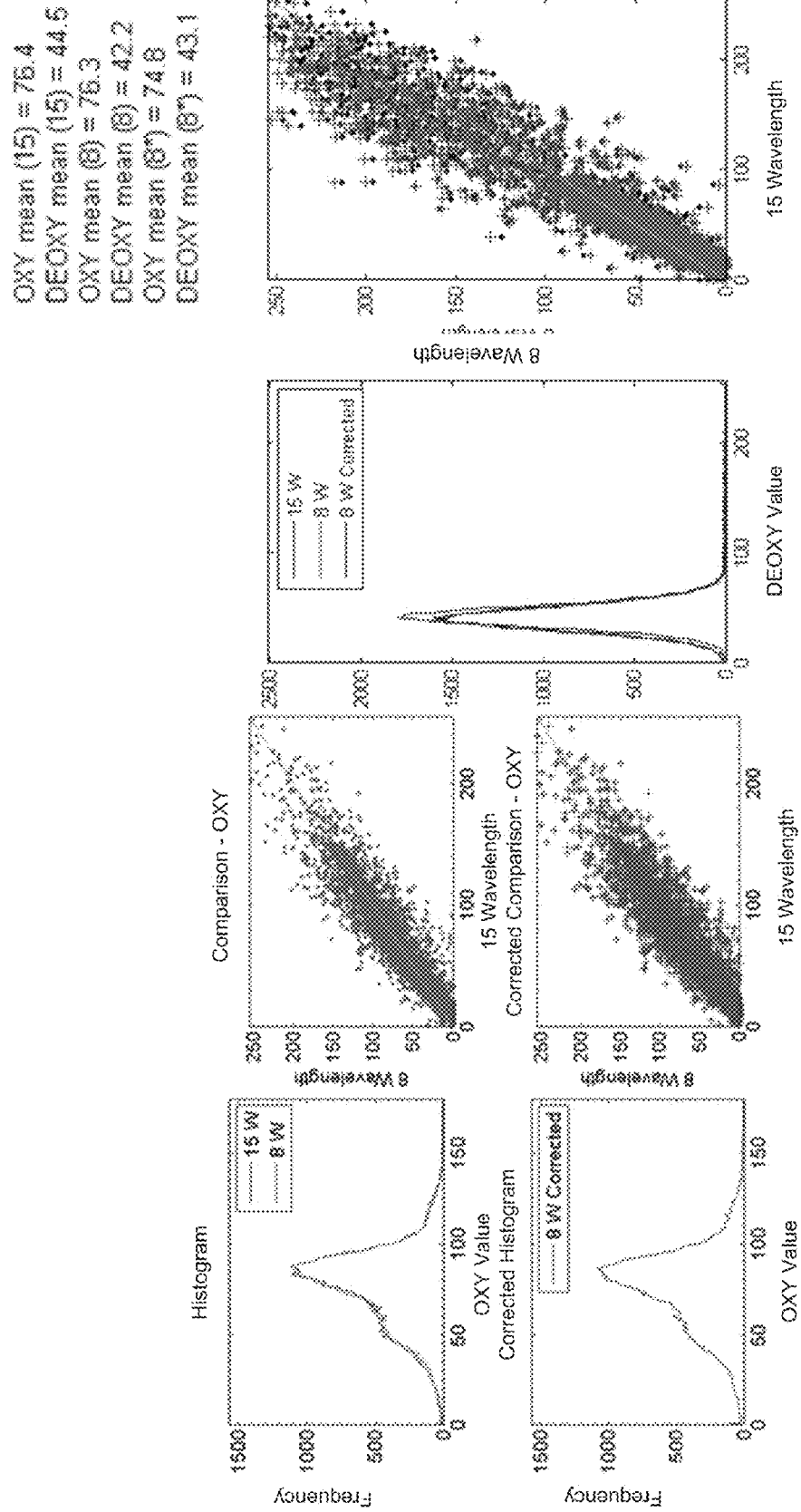
FIGS. 18A, 18B, 18C, and 18D illustrate statistics generated from the three OXY and DEOXY maps generated using all fifteen wavelengths or only the eight wavelengths of exemplary subset 5778, from the third hyperspectral data set, according to some implementations.

As shown in FIGS. 17A-17E, there were minimal visual differences between the processed OXY and DEOXY maps generated using all fifteen wavelengths (FIG. 17A—OXY; FIG. 17C—DEOXY) and those generated using only eight wavelengths (FIG. 17B—OXY; FIG. 17D—DEOXY) for the first data set. The OXY and DEOXY maps generated using only eight wavelengths were corrected using the linear correction factors for subset number 2. FIG. 17E shows a native image of the tissue.

Figure 19A:
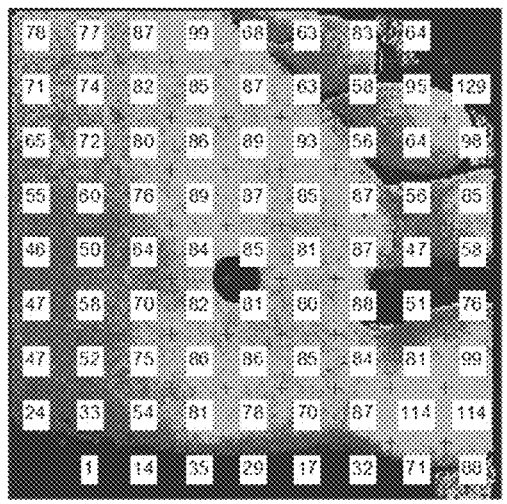
FIGS. 19A, 19B, 19C, and 19D illustrate qualitative analysis of the OXY and DEOXY maps generated from the third hyperspectral data set, using fifteen and eight wavelengths, according to some implementations.
Figure 19B:
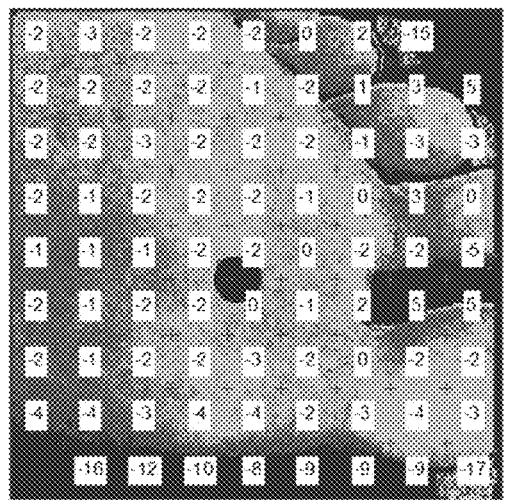
Figure 19C:
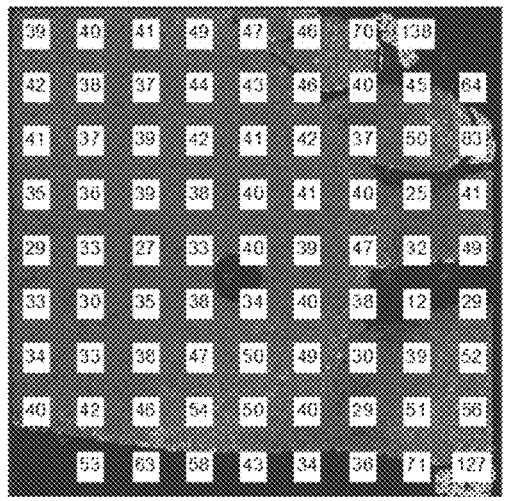
Figure 19D:
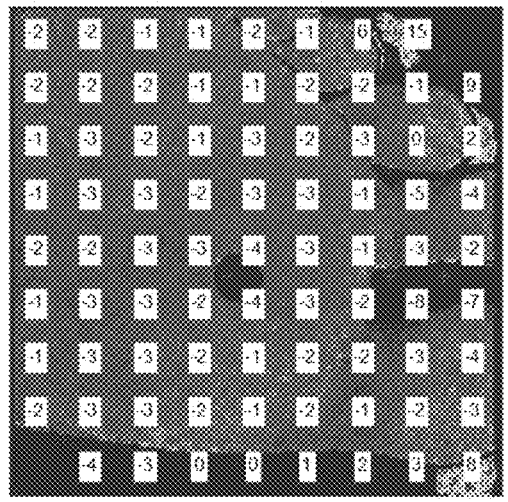

However, the data generated from the second data set indicate unusual and high variance artifacts from the processing which affects the scatter plot by producing large OXY and DEOXY data points with large variance. However, as shown in histograms of FIGS. 17A and 17C, the artifacts are relatively constant between the maps processed using fifteen and eight wavelengths. Consistent with this, the difference in mean OXY and DEOXY between the map generated using eight and fifteen wavelengths is minimal. FIGS. 19B and 19D show the difference between the averaged values overlaid on the OXY and DEOXY maps generated using the corrected eight wavelengths.

Example 5—Evaluation of Optimal Subset #3

To evaluate whether subset #3 (where the wavelength at 640 nm is replaced with a wavelength at 660) is also a suitable substitute for the full complement of fifteen wavelengths, simulations were run using the dataset containing 169 hypercubes, as described in Example 2. For each hyperspectral image (e.g., each dataset), oxyhemoglobin and deoxyhemoglobin concentrations were calculated at all points using all fifteen wavelengths originally collected. Concurrently, the same analysis was performed using only the eight wavelengths in candidate subset #3 (520 nm, 540 nm, 560 nm, 580 nm, 590 nm, 610 nm, 620 nm, and 660 nm).

The resulting OXY and DEOXY maps generated using the eight wavelength set was then compared to the baseline oxyhemoglobin and deoxyhemoglobin values determined using all fifteen wavelengths. The fifteen and eight wavelength processed maps were split into averaged segments, compared, and their correlation evaluated. As reported in Table 1, use of wavelength subset #3 provided OXY and DEOXY values that correlated with the values generated using all fifteen wavelengths, as well as did the valued generated using wavelength subset #2 ($R^2$=0.994 and 0.995, respectively). Individual OXY and DEOXY values generated from the data set using wavelength subset #3 are plotted against the same values generated using all fifteen wavelengths in FIGS. 20A and 20B, respectively.

The effect of down-selecting the 8 wavelengths in subset #3 was also evaluated against published clinical studies using the same set of fifteen wavelengths, described above. The clinical study by Nouvong et al. (Diabetes Care, 32(11): 2056-61 (2009) developed an ulcer healing index by imaging peri-wound tissue at all fifteen wavelengths and then analyzing the ability to predict ulcer healing outcomes based on the measured oximetry. Nouvong et al. reported a sensitivity, specificity, and positive predictive value of 80%, 74%, and 90%, respectively, using data from all fifteen wavelengths collected.

Figure 20A:
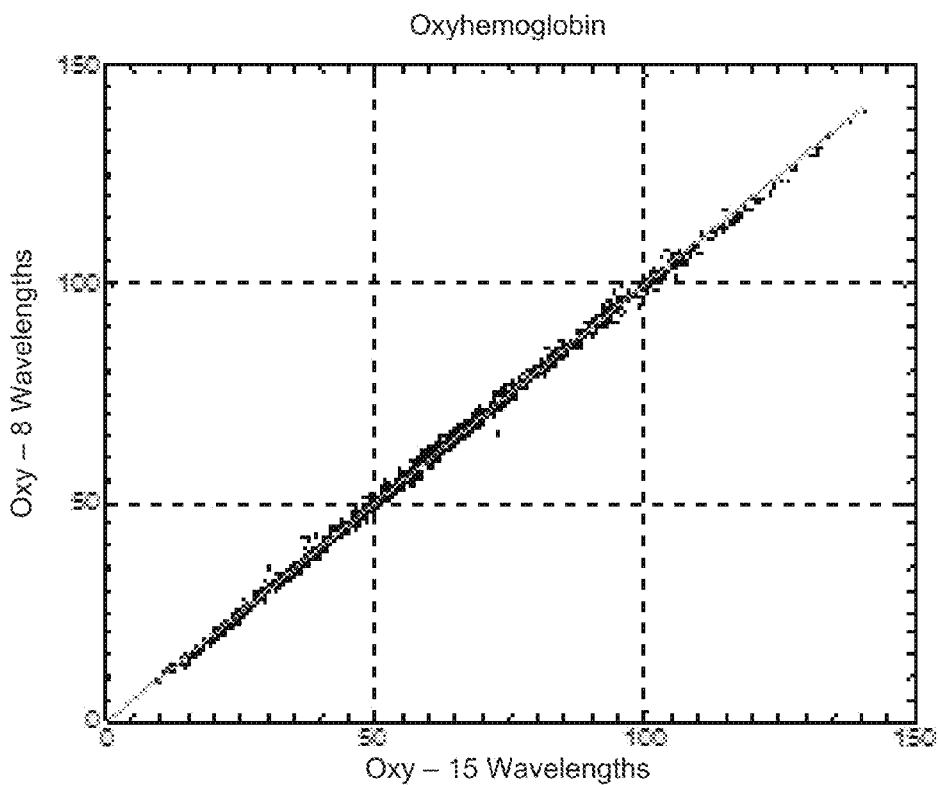
FIGS. 20A and 20B illustrate OXY or DEOXY scatter plots for (a) OXY and (b) DEOXY values generated using all fifteen wavelengths vs. the eight wavelengths of optimal subset #3, respectively.
Figure 20B:
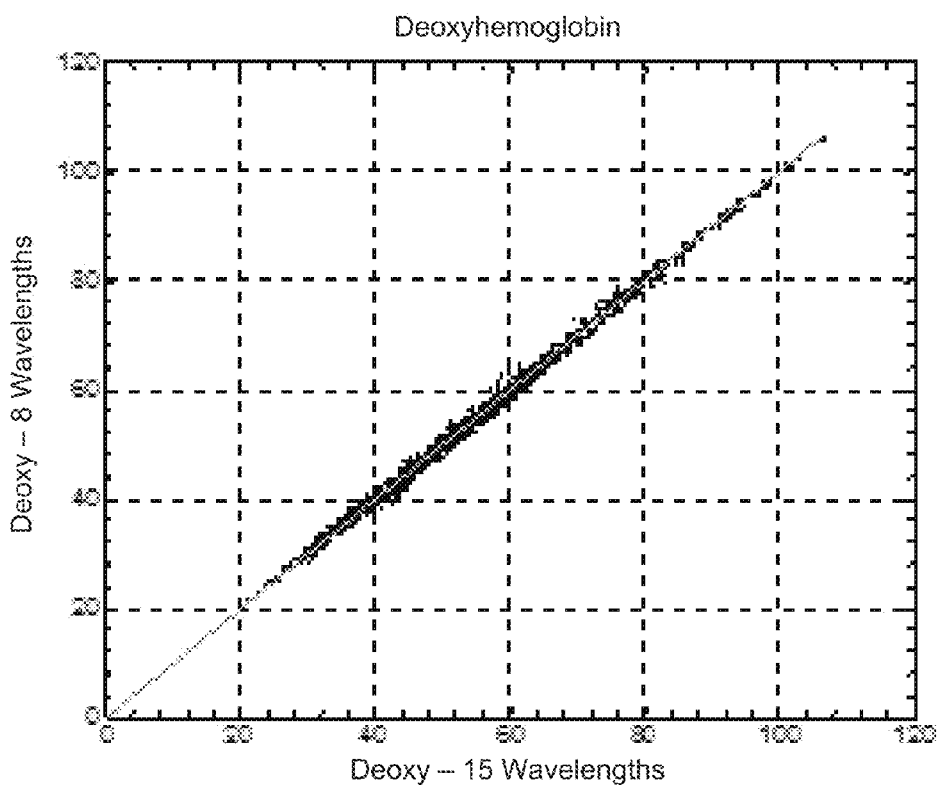

We simulated the published study, in-silico, using the reported data from only the eight wavelengths of subset #3, using an additive noise model based on the correlation data reported in FIGS. 20A and 20B. Addition of the noise to the final averaged values is a worst case assumption, since noise is typically random (positive and negative) and cancels out over a large sample.

Figure 21A:
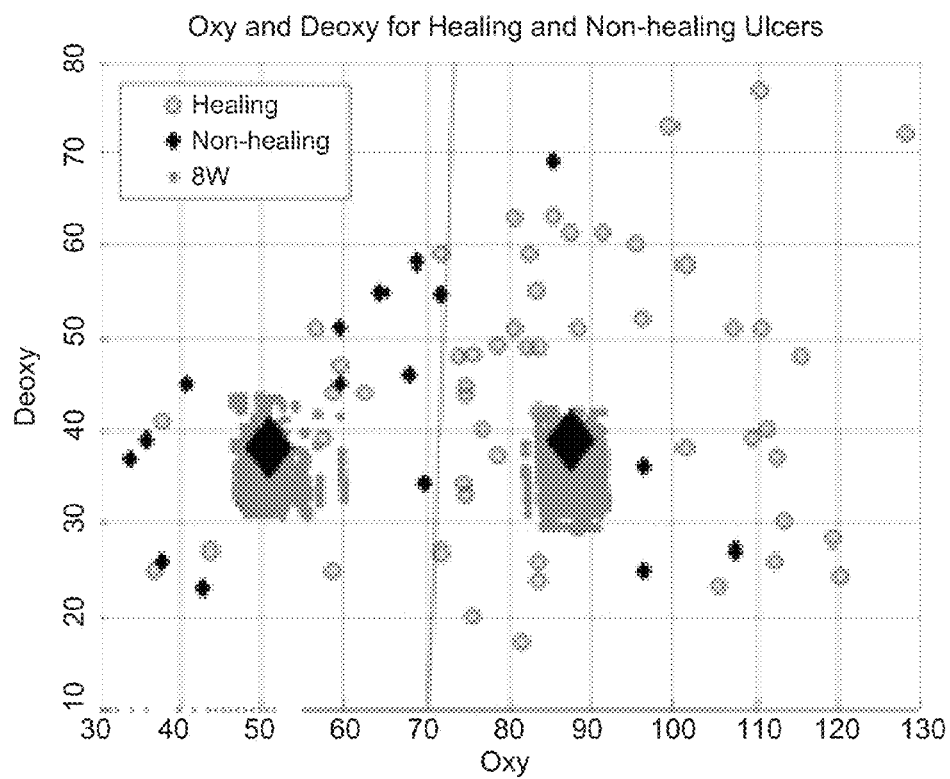
FIGS. 21A and 21B illustrate the results of a simulation of the clinical trial performed by Nouvong et al. (2009) using data from only the eight wavelengths of optimal subset #3.
Figure 21B:
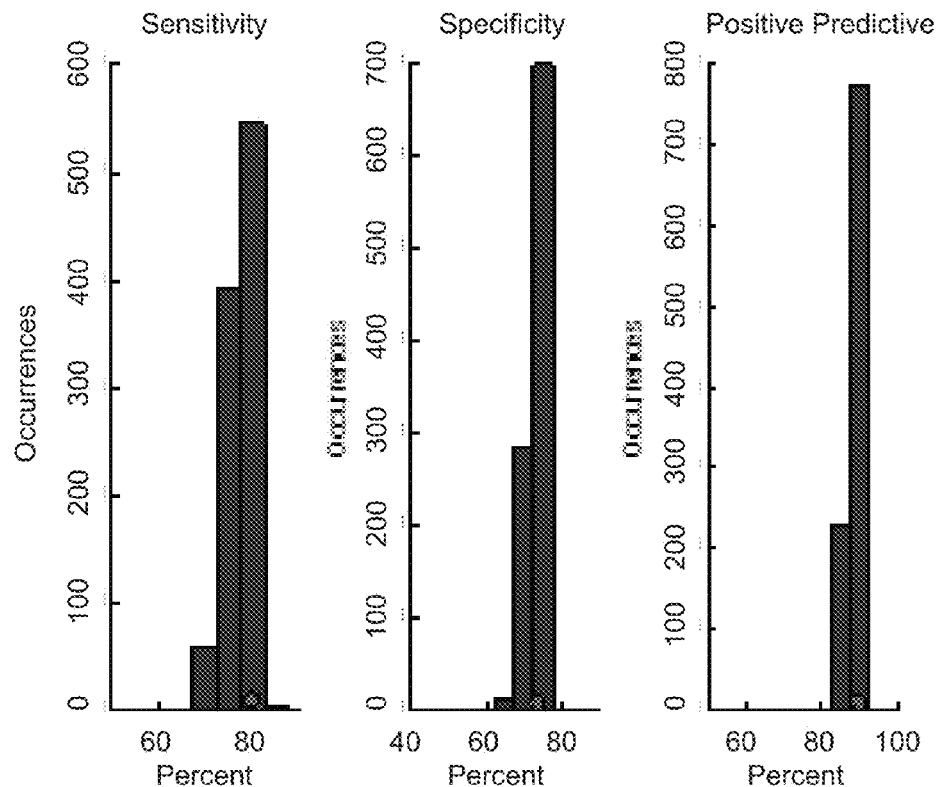

The in-silico simulation was performed several hundred times. Each time, the sensitivity, specificity, and positive predictive value was recalculated and compared it to the reported. The results of the simulation are shown in FIG. 21A, where the cloud of green points show individual instances of the Monte Carlo analysis. The distribution of sensitivity, specificity, and positive predictive values from all of the simulations are represented in FIG. 21B. Average results for the in-silico simulations are presented in Table 2, below. Even under these most aggressive noise conditions, our simulations show that essentially the same clinical results can be achieved using only the eight wavelengths of subset #3, under the absolute worst-case noise conditions.

TABLE 2

Sensitivity, specificity and positive predictive value reported by Nouvon et al., and simulated by the Monte Carlo analysis described above.

| | Sensitivity | Specificity | Positive Predictive Value |
|---|---|---|---|
| Nouvong, et al. | 80% | 74% | 90% |
| Simulated 8 Wavelength | 77.8% | 73.7% | 89.4% |

The terminology used herein is for the purpose of describing particular embodiments only and is not intended to be limiting of the claims. As used in the description of the embodiments and the appended claims, the singular forms "a," "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

It will also be understood that, although the terms "first," "second," etc. may be used herein to describe various elements, these elements should not be limited by these terms. These terms are only used to distinguish one element from another. For example, a first wavelength could be termed a second wavelength, and, similarly, a second wavelength could be termed a first wavelength, which changing the meaning of the description, so long as all occurrences of the "first wavelength" are renamed consistently and all occurrences of the "second wavelength" are renamed consistently. The first wavelength and the second wavelength are both wavelengths, but they are not the same wavelength.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method for determining tissue oxygenation comprising:
    at a system comprising a processor and memory, the memory including instructions for:
    obtaining a data set comprising a plurality of images of a tissue of interest, each respective image in the plurality of images resolved at a different spectral band, in a predetermined set of eight to twelve spectral bands, and comprising an array of pixel values;
    registering, using the processor, the plurality of images on a pixel-by-pixel basis, to form a plurality of registered images of the tissue; and
    performing spectral analysis at a plurality of points in a two-dimensional area of the plurality of registered images of the tissue, the spectral analysis including determining approximate values of oxyhemoglobin levels and deoxyhemoglobin levels at each respective point in the plurality of points,
    wherein the predetermined set of eight to twelve spectral bands includes spectral bands having central wavelengths of:
    520±3 nm, 540±3 nm, 560±3 nm, 580±3 nm, 590±3 nm, 610±3 nm, 620±3 nm, and 660±3 nm,
    wherein the spectral bands having central wavelengths of 520±3 nm, 540±3 nm, 560±3 nm, 580±3 nm, 590±3 nm, 610±3 nm, and 620±3 nm have a full width at half maximum of less than 15 nm, and
    wherein the spectral band having the central wavelength of 660±3 nm has a full width at half maximum of less than 20 nm.

2. The method of claim 1, wherein obtaining the data set comprises:
    at the system:
    capturing the plurality of images of the tissue of interest.

3. The method of claim 2, wherein all of the plurality of images are captured concurrently.

4. The method of claim 2, wherein a first subset of the plurality of images is captured concurrently at a first time point and a second subset of the plurality of images is captured concurrently at a second time point, other than the first time point.

5. The method of claim 2, wherein the system is an imaging system and the spectral analysis is performed at the imaging system.

6. The method of claim 1, wherein performing the spectral analysis comprises:
resolving absorption signals at each respective point in the plurality of points;
accounting for a melanin contribution and loss of signal from diffuse scattering at each respective point in the plurality of points, thereby forming a plurality of corrected absorption signals; and
determining approximate values of oxyhemoglobin levels and deoxyhemoglobin levels from the corrected absorption signals at each respective point in the plurality of points.

7. The method of claim 6, wherein the contribution provided by melanin and the losses provided by diffuse scattering to the plurality of tissue oxygenation measurements are collectively modeled as a second order polynomial.

8. The method of claim 1, wherein the predetermined set of eight to twelve spectral bands consists of a set of eight spectral bands, wherein the set of eight spectral bands have central wavelengths of:
520±3 nm, 540±3 nm, 560±3 nm, 580±3 nm, 590±3 nm, 610±3 nm, 620±3 nm, and 660±3 nm.

9. The method of claim 1, wherein the predetermined set of eight to twelve spectral bands consists of a set of eight spectral bands, wherein the set of eight spectral bands have central wavelengths of:
520±2 nm, 540±2 nm, 560±2 nm, 580±2 nm, 590±2 nm, 610±2 nm, 620±2 nm, and 660±2 nm.

10. The method of claim 1, wherein the predetermined set of eight to twelve spectral bands consists of a set of eight spectral bands, wherein the set of eight spectral bands have central wavelengths of:
520±1 nm, 540±1 nm, 560±1 nm, 580±1 nm, 590±1 nm, 610±1 nm, 620±1 nm, and 660±1 nm.

11. The method of claim 1, wherein the predetermined set of eight to twelve spectral bands consists of a set of eight spectral bands, where the set of eight spectral bands have central wavelengths of:
520 nm, 540 nm, 560 nm, 580 nm, 590 nm, 610 nm, 620 nm, and 660 nm.

* * * * *